US010405795B1

(12) United States Patent
Osorio et al.

(10) Patent No.: US 10,405,795 B1
(45) Date of Patent: *Sep. 10, 2019

(54) METHODS OF CLASSIFYING PERIORBITAL DYSCHROMIA AND SYSTEMS THEREFOR

(71) Applicant: The Procter & Gamble Company, Cincinnati, OH (US)

(72) Inventors: Karen Marie Osorio, Cincinnati, OH (US); Karen Kay Kalla, Cincinnati, OH (US); Wenzhu Zhao, Mason, OH (US); Bradley Bryan Jarrold, Union Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1112 days.

This patent is subject to a terminal disclaimer.

(21) Appl. No.: 14/215,785

(22) Filed: Mar. 17, 2014

Related U.S. Application Data

(60) Provisional application No. 61/798,208, filed on Mar. 15, 2013, provisional application No. 61/798,278, filed on Mar. 15, 2013, provisional application No. 61/798,340, filed on Mar. 15, 2013.

(51) Int. Cl.
A61B 5/00 (2006.01)
A61B 5/103 (2006.01)
A61B 10/02 (2006.01)

(52) U.S. Cl.
CPC ............ A61B 5/444 (2013.01); A61B 5/0064 (2013.01); A61B 5/0075 (2013.01); A61B 5/0077 (2013.01); A61B 5/0082 (2013.01); A61B 10/02 (2013.01)

(58) Field of Classification Search
None
See application file for complete search history.

(56) References Cited

U.S. PATENT DOCUMENTS

| 5,415,861 | A | 5/1995 | Duffy et al. |
| 5,547,673 | A | 8/1996 | Bombardelli |
| 5,914,116 | A | 6/1999 | Suares et al. |
| 6,641,848 | B1 | 11/2003 | Bonte et al. |
| 7,436,987 | B2 | 10/2008 | Takano et al. |
| 7,815,948 | B2 | 10/2010 | Paufique |
| 7,977,290 | B1 | 7/2011 | Deane |
| 8,535,738 | B2 | 9/2013 | Collins et al. |
| 2003/0149347 | A1 | 8/2003 | Kauffmann et al. |
| 2006/0193818 | A1 | 8/2006 | Southall et al. |
| 2007/0184012 | A1 | 8/2007 | Perrier et al. |
| 2008/0234194 | A1 | 9/2008 | Brem et al. |
| 2008/0279902 | A1 | 11/2008 | Luria et al. |
| 2009/0017080 | A1 | 1/2009 | Tanner et al. |
| 2010/0047361 | A1 | 2/2010 | Perrier et al. |
| 2010/0247471 | A1 | 9/2010 | Li et al. |
| 2011/0123703 | A1* | 5/2011 | Mohammadi ......... A61B 5/442 427/2.12 |
| 2011/0230566 | A1 | 9/2011 | Tamargo et al. |
| 2012/0283112 | A1 | 11/2012 | Binder et al. |
| 2013/0189381 | A1 | 7/2013 | Dal Farra et al. |
| 2013/0259816 | A1 | 10/2013 | Hakozaki et al. |
| 2013/0261006 | A1 | 10/2013 | Hakozaki et al. |
| 2013/0261007 | A1 | 10/2013 | Hakozaki et al. |
| 2013/0261024 | A1 | 10/2013 | Hakozaki et al. |
| 2013/0309217 | A1 | 11/2013 | Schmidt |
| 2017/0296456 | A1 | 10/2017 | Osorio |
| 2017/0296457 | A1 | 10/2017 | Osorio |
| 2017/0296458 | A1 | 10/2017 | Osorio |
| 2017/0296459 | A1 | 10/2017 | Osorio |
| 2017/0296460 | A1 | 10/2017 | Osorio |
| 2017/0296461 | A1 | 10/2017 | Osorio |

FOREIGN PATENT DOCUMENTS

| CN | 101152138 | 12/2010 |
| EP | 1698325 A1 | 9/2006 |
| FR | 2811226 | 1/2002 |
| FR | 2925331 | 4/2010 |
| KR | 2013058107 | 6/2013 |
| KR | 2013125969 | 11/2013 |
| WO | WO200166079 A1 | 9/2001 |
| WO | WO2004080380 | 10/2004 |
| WO | WO 2011103449 | 8/2011 |

OTHER PUBLICATIONS

Demirli et al. RBX Technology Overview. Nov. 3, 2006. Canfield Scientific, Inc. 5 pages.*
Jebara, Tony. 3D Face Data for Normalization. Jun. 23, 2000. world wide web address: c.s. columbia.edu/~jebara/htmlpapers/UTHESIS/node47.html, pp. 1-4. (Year: 2000).*
Subramanian et al. "Gene set enrichment analysis: a knowledge-based approach for interpreting genome-wide expression profiles," Proc.Natl.Acad Sci U.S.A, 102, 15545-15550] (2005).
All Office Actions, U.S. Appl. No. 14/215,323.
All Office Actions, U.S. Appl. No. 14/217,303.
All Office Actions, U.S. Appl. No. 15/098,785.
All Office Actions, U.S. Appl. No. 15/098,804.
All Office Actions, U.S. Appl. No. 15/099,035.
All Office Actions, U.S. Appl. No. 15/099,065.
All Office Actions, U.S. Appl. No. 15/099,087.
All Office Actions, U.S. Appl. No. 15/099,120.

(Continued)

Primary Examiner — Channing S Mahatan
(74) Attorney, Agent, or Firm — John G. Powell

(57) ABSTRACT

A method and system for classifying different types of periorbital dyschromia is disclosed. The method includes providing at least one of a predetermined imaging characteristic and a biological characteristic for each of three different types of periorbital dyschromia, and then measuring the appropriate characteristic on a person exhibiting periorbital dyschromia. The type of periorbital dyschromia exhibited by a person can then be determined by comparing the measured value to the predetermined value and selecting the corresponding type of periorbital dyschromia.

3 Claims, 17 Drawing Sheets

(56) References Cited

OTHER PUBLICATIONS

Demirli et al., RBX Technology Overview, Nov. 2006, 5 pages.
Induchem, Unisooth EG-28, May 5, 2011, 17 pages.
International Search Report and Written Opinion of the International Searching Authority, PCT/US2017/027288, dated Sep. 8, 2017, 12 pages.
International Search Report and Written Opinion of the International Searching Authority, PCT/US2017/027289, dated Sep. 12, 2017, 15 pages.
International Search Report and Written Opinion of the International Searching Authority, PCT/US2017/027290, dated Sep. 8, 2017, 12 pages.
International Search Report and Written Opinion of the International Searching Authority, PCT/US2017/027292, dated Sep. 8, 2017, 11 pages.
International Search Report and Written Opinion of the International Searching Authority, PCT/US2017/027293, dated Sep. 25, 2017, 13 pages.
International Search Report and Written Opinion of the International Searching Authority, PCT/US2017/027294, dated Sep. 25, 2017, 13 pages.
Mintel GNPD Record ID: 1126479, Dark Circle Eye Treatment, Aug. 2008.
Mintel GNPD Record ID: 1295582, Eye Express Radiance Ice Cubes, Mar. 2010.
Mintel GNPD Record ID: 1365520, Sea Buckhorn Age Defying Eye Cream, Jul. 2010.
Mintel GNPD Record ID: 600664, Eye Anti-Aging Moisturizing Treatment, Oct. 2006.
Mintel GNPD Record ID: 806021, Anti-Age Care Eye Contour, Nov. 2007.
Ranu et al., Periorbital Hyperpigmentation in Asians: An Epidemiologic Study and a Proposed Classification, American Society for Dermatologic Surgery, Inc., Sep. 2011, pp. 1297-1303.
Verschoore et al., Determination of Melanin and Haemoglobin in the Skin of Idiopathic Cutaneous Hyperchromia of the Orbital region (ICHOR): A Study of Indian Patients, Journal of Cutaneous and Aesthetic Surgery, Jul.-Sep. 2012; 5(3): 176-182.

\* cited by examiner

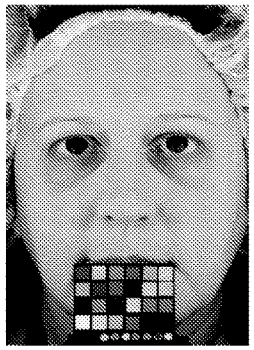  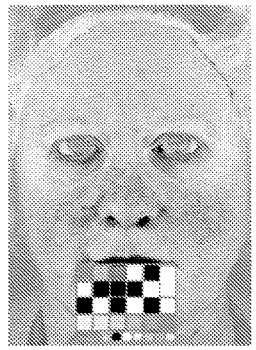  
FIG. 5A　　FIG. 5B　　FIG. 5C　　FIG. 5D　　FIG. 5E
 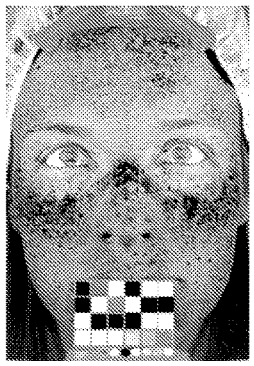 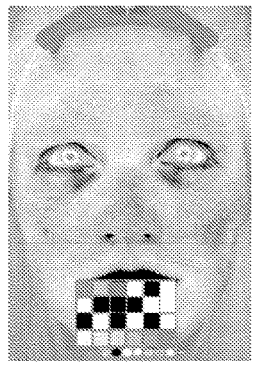  
FIG. 6A　　FIG. 6B　　FIG. 6C　　FIG. 6D　　FIG. 6E
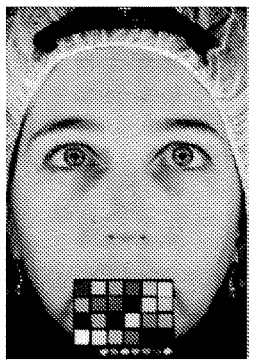    
FIG. 7A　　FIG. 7B　　FIG. 7C　　FIG. 7D　　FIG. 7E

METHODS OF CLASSIFYING PERIORBITAL DYSCHROMIA AND SYSTEMS THEREFOR

FIELD OF THE INVENTION

The present application is directed, generally, to methods and systems for classifying periorbital dyschromia on a person. More specifically, the present application discloses methods and systems for classifying different types of periorbital dyschromia based on visual characteristics, histology, the presence, absence and/or abundance of biomarkers and genetic indicators.

BACKGROUND OF THE INVENTION

A person's eyes are a prominent and noticeable facial feature. Thus, any desirable or undesirable aesthetic features associated with the eyes may influence an individual's perception of herself or himself or the impression that the individual makes on others. Undesirable aesthetic features may include lines, wrinkles and discoloration of the skin. For example, some people may find periorbital dyschromia, sometimes referred to as dark circles or under-eye dark circles, to be aesthetically undesirable and/or they may associate the appearance of periorbital dyschromia with fatigue and/or age. It should come as no surprise then that throughout history a variety of ways to accentuate and/or beautify the eyes have been devised. A common approach to improve the appearance of periorbital dyschromia is to use a cosmetic composition such as a concealer or the like to hide the discoloration. Using make up to hide a perceived flaw may provide a temporary cosmetic benefit, but most conventional make up products require daily application and, in some instances, may even require reapplication throughout the day. Thus, a more permanent solution is desired to reduce and/or eliminate some of the undesirable aesthetic features commonly found around the eye.

As mentioned above, a particularly undesirable aesthetic eye feature is periorbital dyschromia. In an effort to find a solution to the problem of periorbital dyschromia, researchers have previously tried to identify its underlying causes. One theory suggests that periorbital dyschromia occurrence is based on the difference between the thickness of the skin in the periorbital region (i.e., the skin around the eye) and the thickness of the skin in other areas of the face such as the cheeks. It is known that the skin surrounding the eyes is typically thinner than other facial skin (e.g., on the order of 0.33 to 0.36 ram or 3 to 5 times thinner than the rest of the skin of the face). As a result, some conventional theories posit that the skin around the eyes may be easily dehydrated and particularly vulnerable to adverse impact of external factors such as heat, stress, tobacco, UV rays, and excessive facial expressions. According to these theories, the skin tissues around the eye area may undergo multiple variations throughout the day, such as vascularization, hydration and turgescence, which contributes to swelling/puffiness and/or the appearance of dark circles under the eyes. While the thinness of the skin in the periorbital region may play a role in the occurrence of periorbital dyschromia, it is not a suitable characteristic for distinguishing different types of periorbital dyschromia. This is because most people generally have thinner skin in the periorbital region compared to other areas of the face, yet not all people have the same type of periorbital dyschromia or, in sonic instances, any periorbital dyschromia at all. Thus, there remains a need to find suitable characteristics for distinguishing different types of dark circles.

Another theory attributes the occurrence of periorbital dyschromia to hyperpigmentation, or the overproduction of melanin in the skin under the eye. But recent studies have revealed that the cause of under-eye dark circles is more often the result of a combination of factors such as deep vascular congestion/superficial vascularity, hyperpigmentation, skin translucency, and structural shadowing, alone or in combination. The belief that a variety of factors are responsible for causing periorbital dyschromia has led to attempts to classify periorbital dyschromia into discrete types according to the different underlying factor(s) believed to be responsible for the discoloration. But these attempts have failed to provide a commercially viable method of classifying periorbital dyschromia or a system that is suitable for developing and marketing cosmetic products that target periorbital dyschromia. In some instances, there were too many classes of periorbital dyschromia, which requires a manufacturer to develop more cosmetic products or line ups and/or market a more complex treatment method. In some instances, the system used to classify the types of periorbital dyschromia may be too complex to allow consumer to self-diagnose, for example, at home or in a commercial environment such as a retail store.

Another theory suggests that chromophores such as melanin and hemoglobin present in the undereye region contribute to the occurrence of periorbital dyschromia. Melanin is a naturally produced pigment in the skin, and hemoglobin is the iron-containing oxygen-transport metalloprotein in the red blood cells of all humans. It is commonly believed that melanin and hemoglobin are primarily responsible for the skin tone of a person. Thus, some recent attempts to classify dark circles have included analyzing relatively small areas of skin on the lower eyelid with a device that correlates certain wavelengths of reflected light into measurements of melanin and/or hemoglobin present in the skin. While this approach may be suitable for providing an indication of the melanin and/or hemoglobin content of the particular area of skin analyzed, it has several drawbacks. For example, the amount of melanin and/or hemoglobin present in the skin or in the blood vessels in under-eye skin can vary based on a wide variety of environment and/or biological influences, which current analytical approaches do not consider. Additionally, current approaches to classifying dark circles based on melanin and hemoglobin levels may not take into account one or more of a variety of other factors believed to contribute to periorbital dyschromia, which are important to include in a robust classification method and/or system suitable for use in commerce. Previous attempts to analyze periorbital dyschromia based on melanin and hemoglobin measurements also focused on the skin of the lower eyelid. Since it is not uncommon for periorbital dyschromia to occur in the periorbital region above the eye and in portions of the undereye region, but not the entire undereye region, it is important to holistically analyze periorbital dyschromia in the periorbital region.

It is currently recognized that periorbital dyschromia is a multifactorial pathogenesis that is not well elucidated. Past attempts to classify periorbital dyschromia may have shown that there are different types of periorbital dychronia, but they still have failed to provide a suitable method or system of classifying the different types. Further, there is a need for products, product line ups and/or treatment regimens that are particularly suited for treating different types of periorbital dyschromia. For example, some researchers may have recognized that there are different types of periorbital dyschromia, but they still propose treating different types of periorbital dyschromia with the same composition or material.

Other researchers have suggested that a "one size fits all" approach to treating periorbital dyschromia may not be suitable, due to the numerous and not well understood differences in the underlying causes of periorbital dyschromia, but they do not proffer a suitable alternative. Thus, there remains a need for a suitable method and system of classifying periorbital dyschromia, and, in particular, one that is more suitable for commercial use. Otherwise, manufacturers may find it too difficult and/or unpredictable to design and market products and treatment regimens for the diverse array of consumers who typically use their products. Similarly, in some instances, it may be desirable for consumers to self-diagnose, and thus it would be desirable for the method and system to be user friendly, for example, in a commercial setting such as a retail store.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A, 6A and 7A are images of a test subject captured with a digital camera.

FIGS. 5B, 6B and 7B are Brown channel images of a test subject.

FIGS. 5C, 6C and 7C are Red channel images of a test subject.

FIGS. 5D, 6D and 7D illustrate the location of the periorbital dyschromia seen in FIGS. 5B, 6B and 7B, respectively.

FIGS. 5E, 6E and 7E illustrate the location of the periorbital dyschromia seen in FIGS. 5C, 6C and 7C, respectively.

SUMMARY OF THE INVENTION

Figure 1:
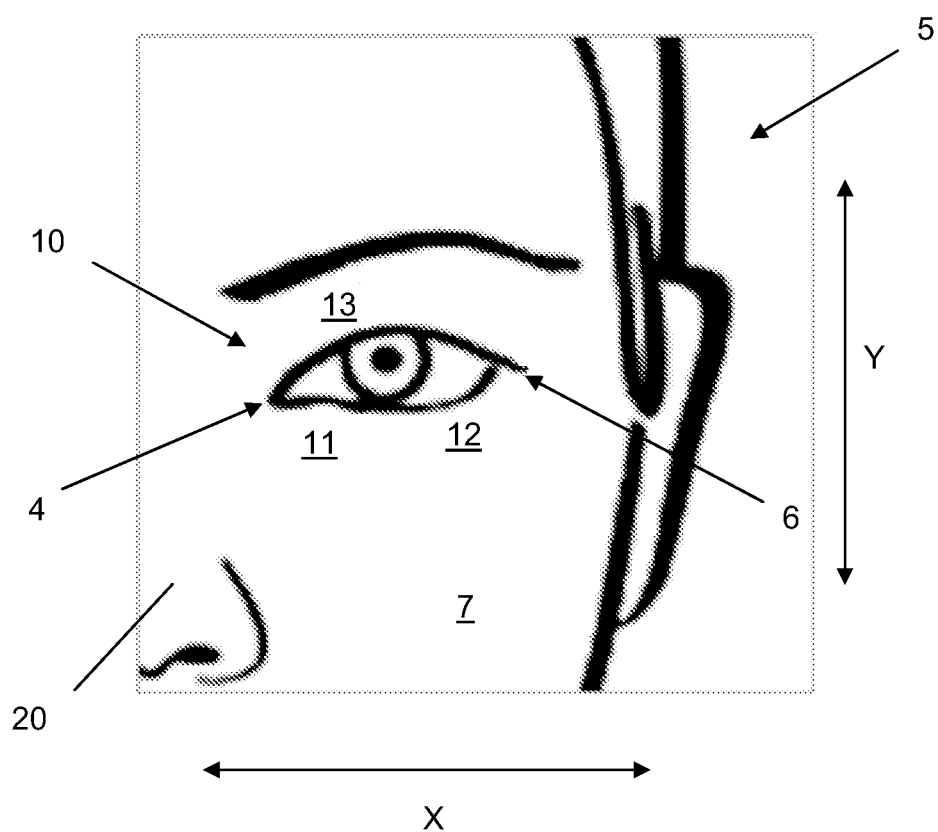
FIG. 1 is an illustration of various portions of a human face.

In order to provide a solution to the aforementioned problems, disclosed herein is a method of classifying periorbital dyschromia comprising providing a first predetermined imaging value for a first type of periorbital dyschromia, a second predetermined imaging value for a second type of periorbital dyschromia, and a third predetermined imaging value for a third type of periorbital dyschromia. The method includes indentifying skin in a periorbital region of a person comprising periorbital dyschromia and measuring an imaging value of at least a portion of the identified skin. The measured imaging value is compared to the predetermined imaging values, and the person is classified as having the first type of periorbital dyschromia when the measured image value corresponds to the first predetermined imaging value, as having the second type of periorbital dyschromia when the measured imaging value corresponds to the second predetermined imaging value, or as having the third type of periorbital dyschromia when the measured imaging value corresponds to the third predetermined imaging value.

DETAILED DESCRIPTION OF THE INVENTION

All percentages are by weight of the personal-care composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

Definitions

"Connectivity map" and "C-map" refer broadly to devices, systems, articles of manufacture, and methodologies for identifying relationships between cellular phenotypes or cosmetic conditions, gene expression, and perturbagens, such as cosmetic actives. A description of connectivity mapping and methods of using connectivity mapping to identify genes and/or compositions of interest can be found in U.S. Publication No. 2012/0283112 titled "Systems and Methods For Identifying Cosmetic Agents For Skin Care Compositions" filed by Binder, et al., on Feb. 22, 2012 and U.S. Publication Nos. 2013/0259816, 2013/0261006, 2013/0261024 and 2013/0261007 all filed by Hakozaki, et al., on Mar. 27, 2013.

"Cosmetic" means providing a desired visual effect on an area of the human body. The visual cosmetic effect may be temporary, semi-permanent or permanent. Some non-limiting examples of "cosmetic products" include products that leave color on the face, such as foundation, mascara, concealers, eye liners, brow colors, eye shadows, blushers, lip sticks, lip balms, face powders, solid emulsion compact, and the like.

"Cosmetic agent" means any substance, as well any component thereof, intended to be rubbed, poured, sprinkled, sprayed, introduced into, or otherwise applied to a mammalian body or any part thereof. Cosmetic agents may include substances that are Generally Recognized as Safe (GRAS) by the US Food and Drug Administration, food additives, and materials used in non-cosmetic consumer products including over-the-counter medications. In some embodiments, cosmetic agents may be incorporated in a cosmetic composition comprising a dermatologically acceptable carrier suitable for topical application to skin. A cosmetic agent includes, but is not limited to, (i) chemicals, compounds, small or large molecules, extracts, formulations, or combinations thereof that are known to induce or cause at least one effect (positive or negative) on skin tissue; (ii) chemicals, compounds, small molecules, extracts, formulations, or combinations thereof that are known to induce or cause at least one effect (positive or negative) on skin tissue and are discovered, using the provided methods and systems, to induce or cause at least one previously unknown effect (positive or negative) on the skin tissue; and (iii) chemicals, compounds, small molecules, extracts, formulations, or combinations thereof that are not known have an effect on skin tissue and are discovered, using the provided methods and systems, to induce or cause an effect on skin tissue.

Some examples of cosmetic agents or cosmetically actionable materials can be found in: the PubChem database associated with the National Institutes of Health, USA; the Ingredient Database of the Personal Care Products Council; and the 2010 International Cosmetic Ingredient Dictionary and Handbook, 13$^{th}$ Edition, published by The Personal Care Products Council; the EU Cosmetic Ingredients and Substances list; the Japan Cosmetic Ingredients List; the Personal Care Products Council, the SkinDeep database; the FDA Approved Excipients List; the FDA OTC List; the Japan Quasi Drug List; the US FDA Everything Added to Food database; EU Food Additive list; Japan Existing Food Additives, Flavor GRAS list; US FDA Select Committee on GRAS Substances; US Household Products Database; the Global New Products Database (GNPD) Personal Care, Health Care, Food/Drink/Pet and Household database; and from suppliers of cosmetic ingredients and botanicals.

Other non-limiting examples of cosmetic agents include botanicals (which may be derived from one or more of a root, stem bark, leaf, seed or fruit of a plant). Some botanicals may be extracted from a plant biomass (e.g., root, stem, bark, leaf, etc.) using one more solvents. Botanicals may comprise a complex mixture of compounds and lack a distinct active ingredient. Another category of cosmetic agents are vitamin compounds and derivatives and combinations thereof, such as a vitamin B3 compound, a vitamin B5 compound, a vitamin B6 compound, a vitamin B9 compound, a vitamin A compound, a vitamin C compound, a vitamin E compound, and derivatives and combinations thereof (e.g., retinol, retinyl esters, niacinamide, folic acid, panthenol, ascorbic acid, tocopherol, and tocopherol acetate). Other non-limiting examples of cosmetic agents include sugar amines, phytosterols, hexamidine, hydroxy acids, ceramides, amino acids, and polyols.

"Data architecture" refers generally to one or more digital data structures comprising an organized collection of data. In some embodiments, the digital data structures can be stored as a digital file (e.g., a spreadsheet file, a text file, a word processing file, a database file, etc.) on a computer readable medium. In some embodiments, the data architecture is provided in the form of a database that may be managed by a database management system (DBMS) that is be used to access, organize, and select data (e.g., instances and gene expression signatures) stored in a database.

"Disposed" refers to an element being located in a particular place or position relative to another element.

"Effective amount" means an amount of a compound or composition sufficient to significantly induce a positive or desired benefit, (e.g., a positive skin or feel benefit, reverse the expression of a gene, group of genes and/or gene signature), including independently or in combinations the benefits disclosed herein, but low enough to avoid serious side effects, i.e., to provide a reasonable benefit to risk ratio, within the scope of sound judgment of the skilled artisan.

"Gene expression signature" refers to a rationally derived list, or plurality of lists, of genes representative of a skin tissue condition or a skin agent. In specific contexts, the skin agent may be a benchmark skin agent or a potential skin agent. Thus, the gene expression signature may serve as a proxy for a phenotype of interest for skin tissue. A gene expression signature may comprise genes whose expression, relative to a normal or control state, is increased (up-regulated), whose expression is decreased (down-regulated), and combinations thereof. Generally, a gene expression signature for a modified cellular phenotype may be described as a set of genes differentially expressed in the modified cellular phenotype over the unmodified cellular phenotype. A gene expression signature can be derived from various sources of data, including but not limited to, from in vitro testing, in vivo testing and combinations thereof. In some embodiments, a gene expression signature may comprise a first list representative of a plurality of up-regulated genes of the condition of interest and a second list representative of a plurality of down-regulated genes of the condition of interest.

"Gene expression profiling" refers to the measurement of the expression of multiple genes in a biological sample using any suitable profiling technology. For example, the mRNA expression of thousands of genes may be determined using microarray techniques. Other emerging technologies that may be used include RNA-Seq or whole transcriptome sequencing using NextGen sequencing techniques. Gene expression profiling may be used to generate a gene expression signature.

"Joined" means configurations whereby an element is directly secured to another element by affixing the element directly to the other element, and configurations whereby an element is indirectly secured to another element by affixing the element to intermediate member(s) that in turn are affixed to the other element.

"Keratinous tissue," means keratin-containing tissue layers disposed as the outermost protective covering of mammals which includes, but is not limited to, skin, hair, and nails.'

"Lateral" means a direction that is generally perpendicular to an imaginary centerline that bisects the human body into right and left mirror images. Directions that are within forty-five degrees of being perpendicular to the imaginary centerline are considered lateral.

"Longitudinal" means a direction that is generally parallel to an imaginary centerline that Bisects the human body into right and left mirror images. Directions that are within forty-five degrees of being parallel to the imaginary centerline are considered longitudinal.

"Microarray" refers broadly to any ordered array of nucleic acids, oligonucleotides, proteins, small molecules, large molecules, and/or combinations thereof on a substrate that enables gene expression profiling of a biological sample. Non-limiting examples of microarrays are available from Affymetrix, Inc.; Agilent Technologies, Inc.; Illumina, Inc.; GE Healthcare, Inc.; Applied Biosystems, Inc.; Beckman Coulter, Inc.; etc.

"Periorbital" means around the orbit of the eye. The periorbital region of a person is the area of the face generally disposed around the eye socket and typically lies between the bottom of the brow and the top of the cheek in the longitudinal direction and between the bridge of the nose and the temple in the lateral direction.

"Periorbital dyschromia" is a condition that occurs when the tone of skin in the periorbital region of person is noticeably different from the tone of skin in a nearby portion of the face, such as the cheek, nose, forehead, temple and/or another portion of the periorbital region. Perioribital dyschromia is bilateral, (i.e., it occurs in the periorbital region of both sides of the face). Periorbital dyschromia may appear as a result of hyperpigmented and/or hypopigmented skin disposed in the periorbital region. Periorbital dyschromia may be identified and/or classified according to one or more of the indicators described in more detail below. Periorbital dyschromia herein is classified into one of three types (i.e., Type I, Type II or Type III). The three types of periorbital dyschromia are described and defined in more detail below, and can be readily determined in accordance with the methods herein.

"Personal care composition" means a cosmetic composition or a skin care composition suitable. Is it to be appreciated that a personal care composition may provide both a cosmetic benefit and a skin health benefit, "Reverse," when referring to the gene expression of a gene, means that the expression of the gene is changed such that it is opposite of the expression indicated in a gene signature in a significant way (e.g., p-value <0.1, p-value <0.05, p-value <0.01, p-value <0.001, or p-value <0.0001 as determined by a statistical test like ANOVA or to a t-test). For example, if a gene expression signature indicates that a particular gene is up-regulated, then reversing the expression of the gene can mean that the gene is down-regulated relative to the indicated gene expression signature with a p-value of less than 0.05 as determined by a statistical test like ANOVA or t-test. When referring to gene expression signatures, the term "reversing" depends on the method used to determine the change in gene expression signature. For example, when using connectivity mapping, a connectivity score is generated to represent an amount of differential expression relative to a known gene expression signature, e.g., stored in a data architecture, and the connectivity score can be used as a measure of the amount of reversal in a gene expression signature in a significant way (e.g., p-value <0.1, p-value <0.05, p-value <0.01, p-value <0.001, or p-value <0.0001.

"Skin" means the outermost protective covering of mammals that is composed of cells such as keratinocytes, fibroblasts and melanocytes. Skin includes an outer epidermal layer and an underlying dermal layer. Skin may also include hair and nails as well as other types of cells commonly associated with skin, such as, for example, myocytes, Merkel cells, Langerhans cells, macrophages, stem cells, sebocytes, nerve cells and adipocytes.

"Skin care" means regulating and/or improving skin condition. Some nonlimiting examples of skin care benefits include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin texture or smoothness, improving skin exfoliation or desquamation, plumping the skin, improving skin barrier properties, improve skin tone, reducing the appearance of redness or skin blotches, and/or improving the brightness, radiancy, or translucency of skin. Some nonlimiting examples of "skin care products" include skin creams, moisturizers, lotions, and body washes.

"Skin-care active" means a compound or combination of compounds that, when applied to skin, provide an acute and/or chronic benefit to skin or a type of cell commonly found therein. Skin-care actives may regulate and/or improve skin or its associated cells (e.g., improve skin elasticity; improve skin hydration; improve skin condition; and improve cell metabolism).

"Skin-care composition" means a composition that regulates and/or improves skin condition.

"Skin tone" refers to the perceived color or pigmentation of skin, especially with regard to the evenness of the coloration or pigmentation. "Skin tone" may also include other characteristics of skin that contribute to a consumer perception of overall tone. For example, pore size and distribution, and skin texture may also be considered attributes of overall skin tone.

"Software" and "software application" mean one or more computer readable and/or executable instructions that cause a computing device or other electronic device to perform functions, actions, and/or behave in a desired manner. The instructions may be embodied in one or more various forms like routines, algorithms, modules, libraries, methods, and/or programs. Software may be implemented in a variety of executable and/or loadable forms and can be located in one computer component and/or distributed between two or more communicating, co-operating, and/or parallel processing computer components and thus can be loaded and/or executed in serial, parallel, and other manners. Software can be stored on one or more computer readable medium and may implement, in whole or part, the methods and functionalities of the present invention.

"Topical application" means to apply or spread the compositions of the present invention onto the surface of the keratinous tissue.

Before now, the underlying causes of periorbital dyschromia were not particularly well elucidated. However, it has unexpectedly been found that there are common themes associated with periorbital dyschromia that can lend themselves to differentiation based on a variety of relatively straightforward evaluation techniques. Previous attempts to classify periorbital dyschromia did not appreciate that periorbital dyschromia can be grouped into distinct categories based on the visual evaluation, imaging, biomarker, histology, and/or genetic analysis techniques disclosed herein. Based on these newly discovered distinctions, it is believed that the methods and systems described herein, individually and/or collectively, may enable the development and/or marketing of improved cosmetic products and/or treatment regimens particularly suited for treating different types of periorbital dyschromia.

Visual Evaluation

Periorbital dyschromia may be classified into three different types as well as a "No Dyschromia" condition using visual evaluation techniques. In particular, the location and/or tone(s) of a dyschromic portion of periorbital skin may be analyzed visually to determine whether periorbital dyschromia is present and, if present, which type is present. For example, a No Dyschromia condition may be visually characterized by the lack of an uneven or discontinuous skin tone in the periorbital region. Visual evaluation may be done by an expert grader (i.e., someone trained to visually classify periorbital dyschromia), for example, as described in more detail in the Methods section below, or the visual classification may be done by a non-expert (e.g., a consumer who self-diagnoses) based on, for example, a set of instructions or a visual cue.

FIG. 1 illustrates the periorbital region 10 of a human face 5 divided into three zones. Zone 1 11 is disposed generally under the eye in the longitudinal direction (represented by the arrow Y) and extends under the eye in the lateral direction (represented by the arrow X) from the inner canthus 4 (i.e., the corner of the eye proximate the nose 20) to an area under the eye that is less than the complete distance to the outer canthus 6 (i.e., the corner of the eye spaced furthest from the nose). For example, as illustrated in FIG. 1, Zone 1 11 may extend from the inner canthus 4 to about the middle of the undereye portion of the periorbital region 10. But it is to be appreciated that, in some individuals, Zone 1 may extend more than halfway or less than halfway across the under-eye region, but typically not more than 90% of the distance from the inner canthus 4 to the outer canthus 6. Zone 2 12 extends from the distal edge of Zone 1 11 (i.e., the portion of Zone 1 furthest from the nose 20 in the lateral direction) to the outer canthus 6 of the eye. Zone 3 is disposed above the eye and extends laterally from the inner canthus 4 to the outer canthus 6. Zone 3 13 also extends generally in the longitudinal direction Y from the upper eyelid to the bottom of the eyebrow. In some embodiments, it may be desirable to use a target portion of skin disposed on the cheek 7 as a reference or control when evaluating the location and/or tones of periorbital dyschromia.

"Type I" periorbital dyschromia may be visually characterized by continuous discoloration of both the upper and lower eyelid skin. The dyschromic periorbital skin associated with Type I periorbital dyschromia typically includes substantially uniform brown, yellow and/or orange tones, which may resemble the color of tanned skin or an age spot. Additionally or alternatively, Type I periorbital dyschromia may be visually characterized by being generally present in Zones 1, 2 and 3 of the periorbital region of a person.

"Type II" may be visually characterized by continuous discoloration of the lower eyelid skin. The discolored periorbital skin associated with Type II periorbital dyschromia typically includes substantially uniform purple, pink and/or bluish tones, which may resemble bruised skin. Additionally or alternatively, Type II periorbital dyschromia may be visually characterized by being generally present in Zone 1 of the periorbital region and generally absent from Zone 2 and Zone 3.

"Type III periorbital dyschromia" typically includes a combination of characteristics of Types I and II, such as color and location in the periorbital region. In some instances, Type III periorbital dyschromia may be characterized by discontinuous discoloration of the undereye portion of the periorbital region, which is different from the more uniform discoloration associated with Types I and II. The patches of discolored periorbital skin associated with Type III periorbital dyschromia are generally present in Zone 1 and Zone 2 and may also be present in the inner portion of Zone 3 (i.e., the portion of Zone 3 that is closest to the nose).

Figure 2A:
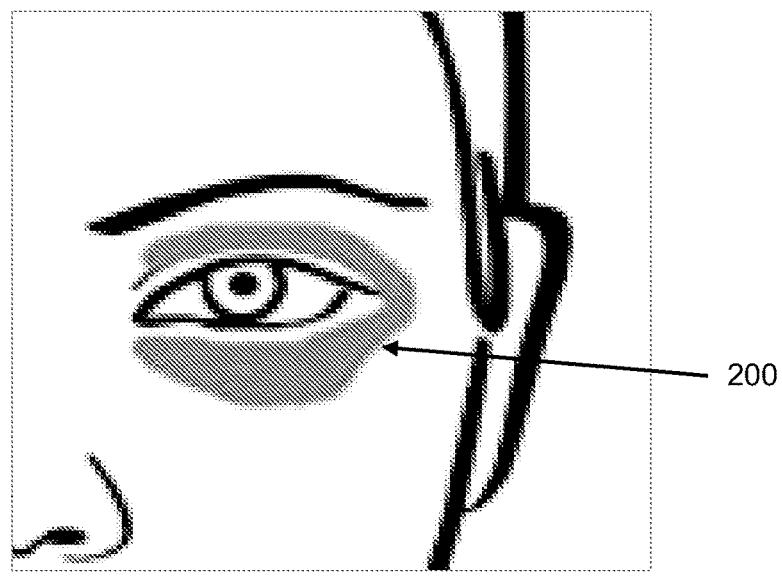
FIGS. 2A and 2B illustrate examples of the portion of the periorbital region affected by Type I periorbital dyschromia.
Figure 2B:
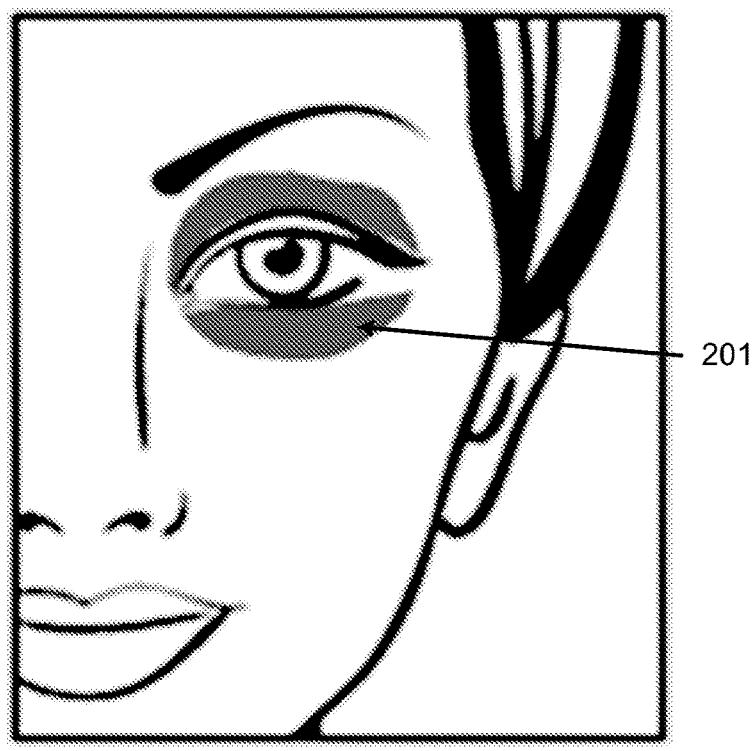
Figure 3A:
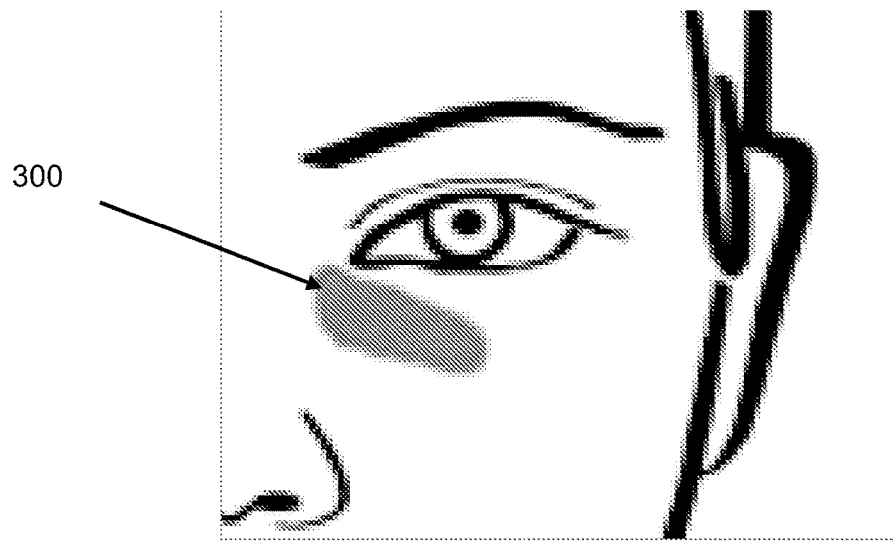
FIGS. 3A and 3B illustrate examples of portion of the periorbital region affected by Type II periorbital dyschromia.
Figure 3B:
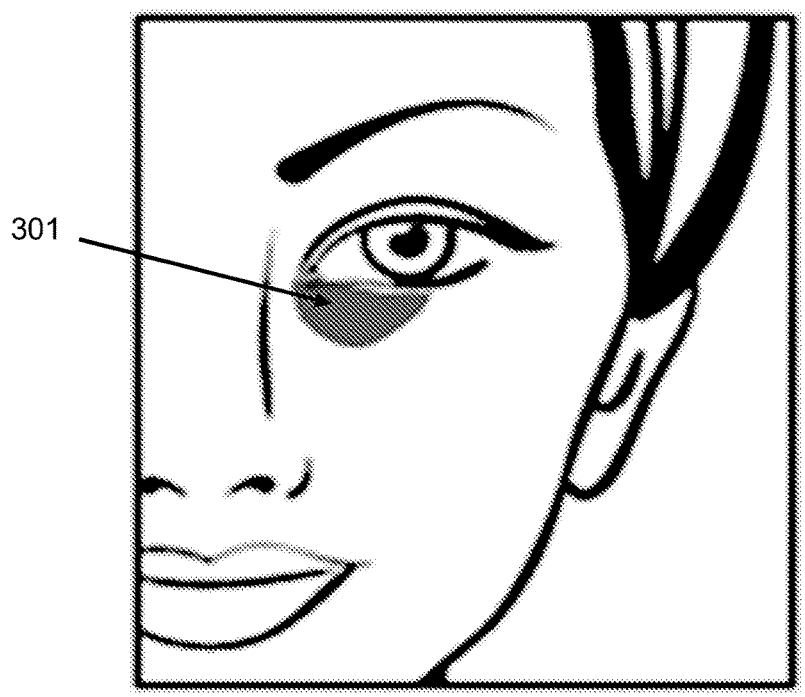
Figure 4A:
FIGS. 4A and 4B illustrate examples of portion of the periorbital region affected by Type III periorbital dyschromia.
Figure 4B:
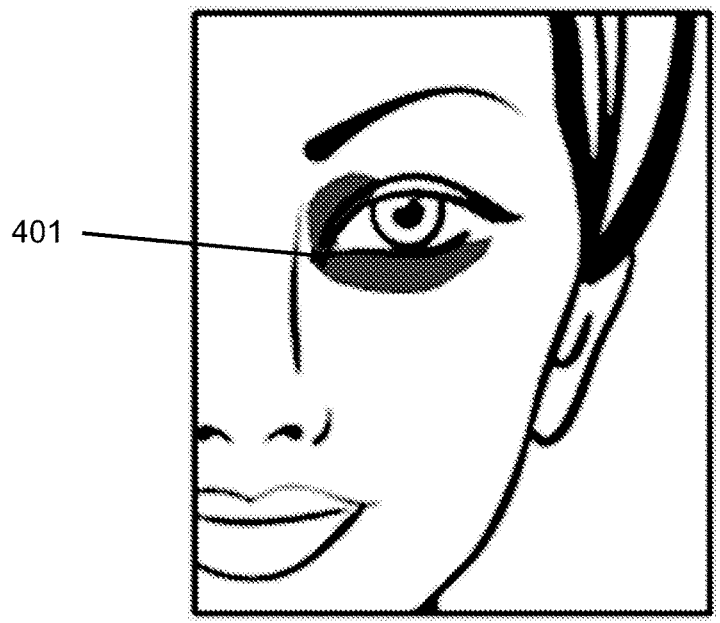

FIGS. 2A and 2B illustrate examples of Type I periorbital dyschromia, which is represented by the shaded portions 200 and 201, respectively, of the periorbital region. FIGS. 3A and 3B illustrate examples of Type II periorbital dyschromia (i.e., the shaded portions 300 and 301, respectively, of the periorbital region). FIGS. 4A and 4B illustrate examples of Type III periorbital dyschromia (i.e., the shaded portions 400 and 401, respectively, of the periorbital region).

Imaging Classification—RGB

Type I, Type II and Type III periorbital dyschromia may be distinguished from one another using known imaging technique such as RGB and/or RBX® color imaging and/or gray scale imaging. An image of the region of interest ("ROI") (e.g., periorbital region of a person) is captured by an image capture device, and at least a portion of the image is analyzed (e.g., by a computer) and assigned an imaging value based on the analysis. This determined imaging value may then be compared to a predetermined imaging value, which can be a single value or a range of values (e.g., one or more of the RGB values disclosed herein). The predetermined imaging value defines a particular type of periorbital dyschromia, and the comparison enables a user to identify which type of periorbital dyschromia, if any, is exhibited by the person. For example, RGB color imaging uses an additive color model wherein red, green, and blue light are added together in various ways to reproduce a broad array of colors. The RGB color model is particularly suited for sensing, representing, and displaying images in electronic systems such as televisions and computers. RGB is a device-dependent color model, which means that different devices may detect or reproduce a given RGB value differently, since the color elements (such as phosphors or dyes) and their response to the individual R, G, and B levels may vary from manufacturer to manufacturer, or even in the same device over time. Thus, it can be important to use color correction to ensure that an RGB value defines the same color across devices or in the same device over time. Color correction can be readily accomplished by one skilled in the art using commercially available software and techniques.

Classifying periorbital dyschromia according to the imaging classification methods and systems described herein depends on, among other things, the skin tone of an individual. For example, people who are Fitzpatrick I, II and III skin types according to the commonly known Fitzpatrick Scale, may have different color values associated with the different types of periorbital dyschromia as compared to people who are Fitzpatrick skin type IV, V or VI. In some of the examples and descriptions below, the different types of periorbital dyschromia are in relation to people who are Fitzpatrick skin type I, II and/or III (e.g., the imaging values and ratios). However, it is believed, without being limited by theory, that the classification methods and systems herein can be reapplied to people with Fitzpatrick IV, V and VI skin types in the substantially the same manner. In some instances, it may be desirable to normalize the imaging values of one or more zones in the periorbital region to a reference or control value such as an imaging value associated with the cheek. The normalized value may then be used to determine whether periorbital dyschromia is present and, if so, which type.

Type I periorbital dyschromia may be characterized by generally having lower RGB values relative to Types II and III as well as a different ratio of B value to G value ("B/G"). Type II periorbital dyschromia may be characterized by generally having higher RGB values compared to Types I and III. Type III periorbital dyschromia may include characteristics of both Type I and Type II. Tables 1, 2 and 3 below show ranges of color corrected RGB values, B/G ratios, L*a*b* values, chroma values and hue values that may be used to characterize Type I, Type II and Type III periorbital dyschromia, respectively, exhibited by a person having a Fitzpatrick skin type of I, II or III. The values provided in Tables 1, 2 and 3 correspond to a particular portion of the periorbital region referred to as a "mask." Masks, and in particular Mask A, Mask B and Mask C are described in more detail below in the Imaging Method, which provides a suitable method of determining imaging values.

TABLE 1

Type I

| Imaging Value | Mask A | Mask B | Mask C |
| --- | --- | --- | --- |
| R | 118-166 | 135-187 | 128-178 |
| G | 83-119 | 94-136 | 89-129 |
| B | 76-108 | 81-112 | 79-112 |
| B/G | 0.75-0.92 | 0.73-0.86 | 0.74-0.89 |
| L | 48-54 | 43-61 | 41-59 |
| A | 13-18 | 9-17 | 12-18 |
| b | 9-23 | 14-25 | 12-23 |
| Hue (h) | 35-53 | 42-60 | 39-56 |
| Chroma (C) | 16-28 | 17-28 | 17-28 |

TABLE 2

Type II

| Imaging Value | Mask A | Mask B | Mask C |
| --- | --- | --- | --- |
| R | 148-176 | 165-201 | 159-186 |
| G | 102-135 | 128-160 | 115-148 |
| B | 96-128 | 108-145 | 103-136 |
| B/G | 0.86-0.98 | 0.82-0.93 | 0.84-0.94 |
| L | 48-60 | 57-69 | 52-64 |
| a | 11-20 | 9-19 | 10-19 |
| b | 7-16 | 10-20 | 9-17 |
| Hue (h) | 24-54 | 33-61 | 32-57 |
| Chroma (C) | 15-23 | 15-22 | 15-22 |

TABLE 3

Type III

| Imaging Value | Mask A | Mask B | Mask C |
| --- | --- | --- | --- |
| R | 142-172 | 160-188 | 153-177 |
| G | 97-129 | 110-148 | 105-137 |
| B | 88-114 | 92-129 | 90-119 |
| B/G | 0.81-0.95 | 0.79-0.89 | 0.80-0.92 |
| L | 46-57 | 51-64 | 49-60 |
| a | 11-20 | 10-17 | 11-18 |
| b | 9-19 | 13-21 | 11-19 |
| Hue (h) | 29-54 | 42-62 | 36-57 |
| Chroma (C) | 17-24 | 18-24 | 18-24 |

Imaging Classification—RBX

Attempts have been made in the past to classify periorbital dyschromia based on melanin and/or hemoglobin content, which are believed to be the chromophores primarily responsible for skin tone. For example, some previous attempts used conventional instruments (e.g., Mexameter MX-18) to measure the amount of melanin and hemoglobin in the skin. The measured values are then compared to the different types of periorbital dyschromia observed in test subjects to identify any correlations that might be used in classifying the different types of periorbital dyschromia. However, these past attempts concluded that measuring melanin and hemoglobin in this manner does not provide a useful tool for differentiating periorbital dyschromia.

In contrast with previous findings, it has been found that certain imaging technology such as RBX® brand imaging technology, available from Canfield Scientific, Inc., New Jersey, may provide a suitable distinction between Type I, Type II and Type III periorbital dyschromia, based on differences in the Red Channel and Brown channel images, which can correspond to the melanin and hemoglobin present in the skin. This is an unexpected finding, since previous studies have concluded that using imaging systems to measure colorants or chomophores in the skin does not provide a suitable means for classifying periorbital dyschromia.

RBX® brand imaging technology is based on the premise that skin color is characterized by a limited number of colorants, or chromophores, within the layers of skin. In normal, healthy skin, melanin particles, which are primarily responsible for the overall skin color, are small and uniformly distributed resulting in a smooth, even skin tone. Hemoglobin occurs within the vascular structure at the papillary dermis, a sub-layer of skin, in oxygenated and deoxygenated forms and is responsible for red colorations of skin tone. However, it may not be desirable to quantify skin pigmentation by only measuring the total attenuation of broadband light because, apart from melanin, hemoglobin in skin also absorbs visible light in a wavelength dependent manner. Therefore, methods are required to measure light absorbance in more than one spectral band. RBX® brand imaging technology transforms a conventional RGB image (e.g., captured by a conventional digital camera) into a color space where the Red and Brown channels represent hemoglobin and melanin distribution, respectively.

In some instances, Type I periorbital dyschromia may be characterized by relatively high Brown and Red channel contrast in the periorbital region as compared to other portions of the face (e.g., cheek, chin, nose or forehead). FIGS. 5A to 5E illustrate an example of Type I periorbital dyschromia observed in an RBX® image. FIG. 5A is a full color image of a test subject captured with a digital camera. As can be seen in FIG. 5A, periorbital dyschromia appears in Zones I, II and III of the periorbital region of the test subject. FIG. 5B shows the Brown Channel image that corresponds to the digital image of FIG. 5A. FIG. 5C shows the Red Channel image that corresponds to the digital image from FIG. 5A. FIG. 5D provides an illustration of the location of the periorbital dyschromia provided in FIG. 5B (i.e., in the Brown channel), and FIG. 5E provides an illustration of the location of the periorbital dyschromia provided in FIG. 5C (i.e., the Red Channel). As can be seen in FIG. 5C, and as illustrated in FIG. 5E, periorbital dyschromia is present in Zones 1 and 2 and in a portion of Zone 3. However, the periorbital dyschromia appearing in Zone 3 of FIG. 5C is not present in as large an area as the periorbital dyschromia in Zone 3 of FIG. 5B. This may suggest that melanin and hemoglobin both influence the appearance of Type I periorbital dyschromia, but melanin is the more abundant chromophore. FIG. 5E provides an illustration of the periorbital dyschromia that appears in FIG. 5C (i.e., in the Red Channel).

Type II periorbital dyschromia may be characterized by relatively low Brown Channel intensity values in the periorbital skin relative to the surrounding areas of face (e.g., cheek and forehead) and high Red Channel contrast in the periorbital region as compared to other portions of the face. FIGS. 6A to 6E illustrate an example of Type II periorbital dyschromia observed in an RBX®. FIG. 6A is an image of a subject captured with a digital camera. As can be seen in FIG. 6A, periorbital dyschromia appears in Zone 1, but appears to be substantially absent from Zones 2 and 3. FIG. 6B shows the Brown channel image that corresponds to the digital image of FIG. 6A. FIG. 6C shows the Red Channel image that corresponds to the digital image of FIG. 6A. FIG. 6D provides an illustration of the location of the periorbital dyschromia provided in FIG. 6B (i.e., in the Brown channel), and FIG. 6E provides an illustration of the location of the periorbital dyschromia provided in FIG. 6C (i.e., the Red Channel). As can be seen in FIG. 6C, and as illustrated in FIG. 6E, periorbital dyschromia is visible in Zone 1, but appears to be substantially absent from Zones 2 and 3. This may suggest that melanin does not play as significant a role as hemoglobin in Type II periorbital dyschromia.

Type III periorbital dyschromia may be characterized by discontinuous patches of Brown Channel and Red channel intensity in the periorbital region. FIGS. 7A to 7E illustrate an example of Type III periorbital dyschromia observed in an RBX® image. FIG. 7A is an image of a test subject captured with a digital camera. As can be seen in FIG. 7A, periorbital dyschromia appears in Zones 1 and 3, but appears to be substantially absent from Zone 2. FIG. 7B shows the Brown channel image that corresponds to the digital image from FIG. 7A. FIG. 7C shows the Red channel image that corresponds to the digital image from FIG. 7A. FIG. 7D provides an illustration of the location of the periorbital dyschromia provided in FIG. 7B (i.e., in the Brown channel), and FIG. 7E provides an illustration of the location of the periorbital dyschromia provided in FIG. 7C (i.e., the Red Channel). As can be seen in FIG. 7B, and as illustrated in FIG. 7D, periorbital dyschromia appears in Zones 1 and 3 of the periorbital region of the test subject. And as can be seen in FIG. 7C, and as illustrated in FIG. 7E, periorbital dyschromia appears in Zone 1, but appears to be substantially absent from Zones 2 and 3.

Histology

Type I, Type II and Type III periorbital dyschromia may be distinguished from one another using histological evaluation techniques that include, for example, sectioning and staining, followed by examination under a microscope (e.g., light or electron). In particular, it has been found that the abundance and/or location of certain cellular structures (e.g., melanin) within skin biopsy samples obtained from a discolored area of periorbital skin may be used to distinguish Type I, Type II and Type III periorbital dyschromia from one another. Skin tissue samples for use herein may be obtained, sectioned and/or stained according to any suitable method in the art. The Biopsy Method described in more detail below is an example of a suitable method of sample collection, sectioning and staining. Examples of conventional stains suitable for use herein include hematoxylin and eosin stain ("H&E stain") and Fontana-Masson stain. H&E stain is a known for use in histology and involves the application of hemalum, which is a complex formed from aluminum ions and oxidized haematoxylin, to a tissue sample. The application of hemalum colors the nuclei of the cells in the sample dark blue or purple. The nuclear staining is followed by counterstaining with an aqueous or alcoholic solution of eosin Y, which colors eosinophilic structures such as cytoplasm in various shades of red, pink and orange. Fontana-Masson stain uses ammoniacal silver nitrate to detect cellular structures in a tissue sample that are capable of reducing the silver nitrate to metallic silver, which stains the structure black.

Figure 8:
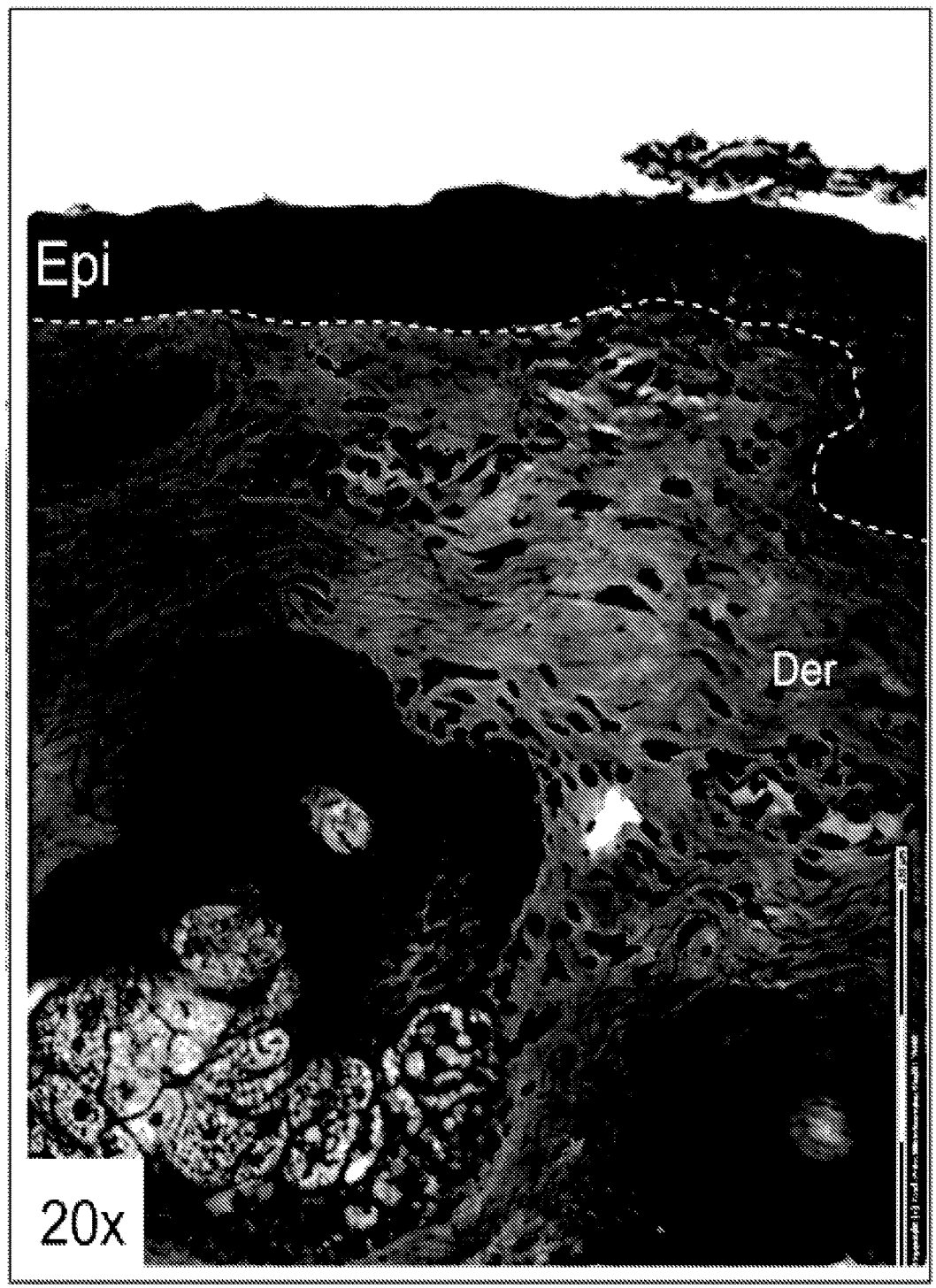
FIG. 8 is a 20× micrograph of a skin tissue sample from a subject exhibiting No Dyschromia.

FIGS. 8 to 11 are micrograph images at 20× magnification of H&E-stained biopsy samples from skin disposed in the periorbital region of human test subjects. The samples were collected, sectioned and stained according to the Biopsy Method described in more detail below. Each test subject was classified as exhibiting Type I, Type II, Type III or No Dyschromia by an expert grader. The skin tissue sample shown in FIG. 8 is from a test subject classified as exhibiting No Dyschromia, and thus may serve as a suitable control. The dark (i.e., purple) bodies shown in FIG. 8 are nuclei of the various cells commonly disposed in the dermis and epidermis of an individual. The lighter (i.e., red/pink) stained areas between the nuclei corresponds to cytoplasm, connective tissue and glycoproteins.

Figure 9:
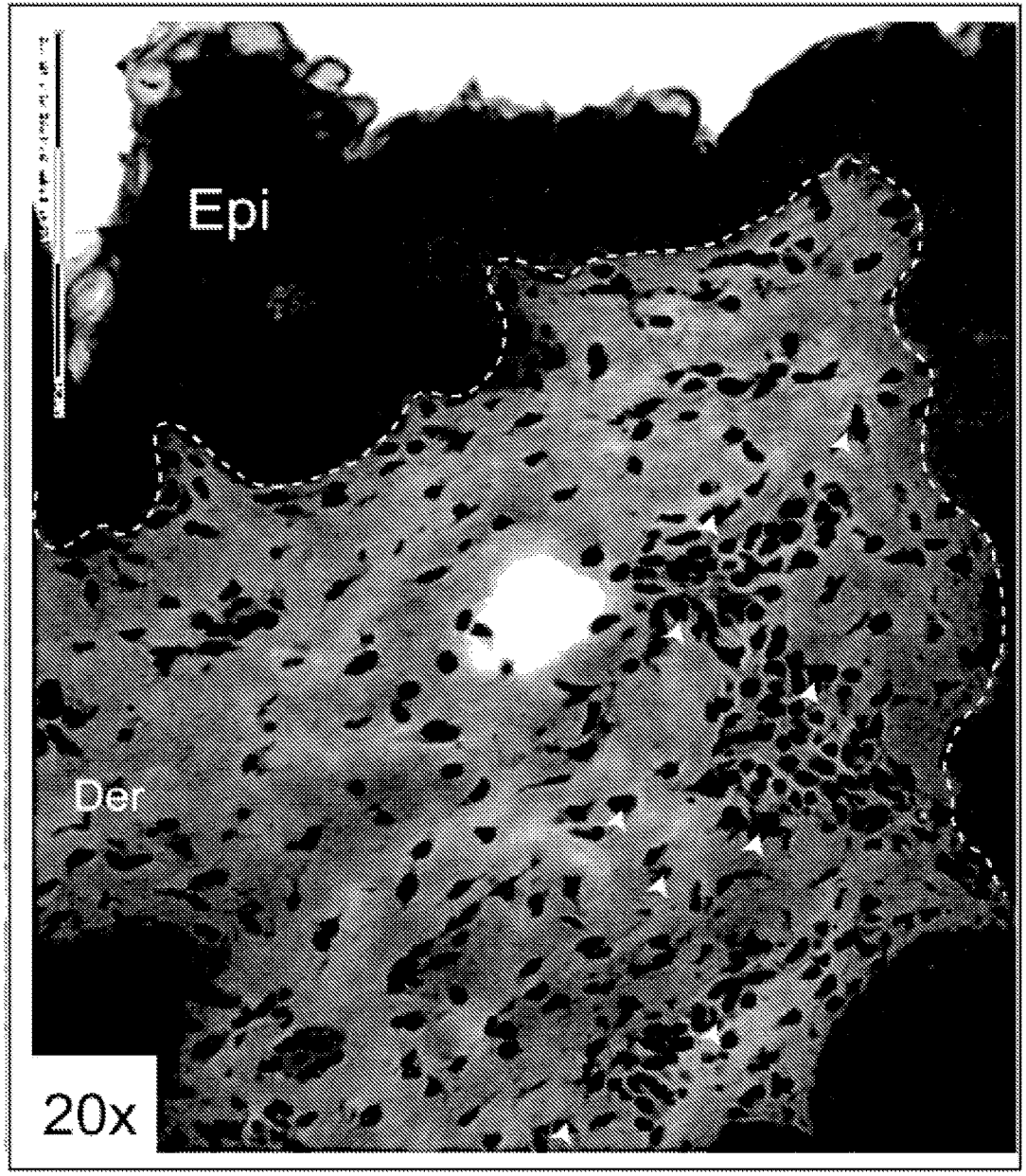
FIG. 9 is a 20× micrograph of a skin tissue sample from a subject exhibiting Type I periorbital dyschromia.

The skin tissue sample shown in FIG. 9 is from a test subject classified as exhibiting Type I periorbital dyschromia. The white arrowheads shown in FIG. 9 point to deposits, which are brown in color when seen in a color micrograph, disposed around the nuclei of some of the cells in the sample. When the tissue samples are stained with Fontana-Masson stain, the deposits appear black ("Fontana-Masson positive deposits"), which indicates that they may be melanin. This is surprising because melanin is generally not associated with the dermis and is more commonly found in the epidermis. As can be seen in FIG. 9, the Fontana-Masson positive deposits are generally disposed around the nuclei of cells that appear to be clustered together underneath the epidermal-dermal junction. The clustered cells are believed to be fibroblasts, which account for the majority of cells typically found in a healthy dermis. Healthy fibroblasts generally appear as elongated, flat cells, but the clustered cells in FIG. 9 are round when viewed under a light microscope, which indicates that they may not be healthy fibroblasts. Thus, it is believed, without being limited by theory, that the presence of these melanin deposits in the dermis may be related to an underlying biological cause of Type I periorbital dyschromia. In particular, the round clustered appearance of the fibroblasts may be associated with an inflammation response. In view of this discovery, it may be desirable to provide a method and system of classifying periorbital dyschromia based, at least in part, on dermal melanin content. It may also be desirable to configure products and regimens suited for treating Type I periorbital dyschromia to address the presence of melanin in the dermis and/or the factors that may influence the presence of melanin in the dermis.

In addition to the discovery of unexpected amounts of Fontana-Masson positive deposits in the dermis, there also appeared to be an overabundance of melanin in the epidermis of periorbital skin tissue samples taken from Type I individuals. Thus, it may be desirable to tailor products for treating Type I periorbital dyschromia to include a cosmetic active that addresses the presence of excess melanin in the epidermis.

Figure 10:
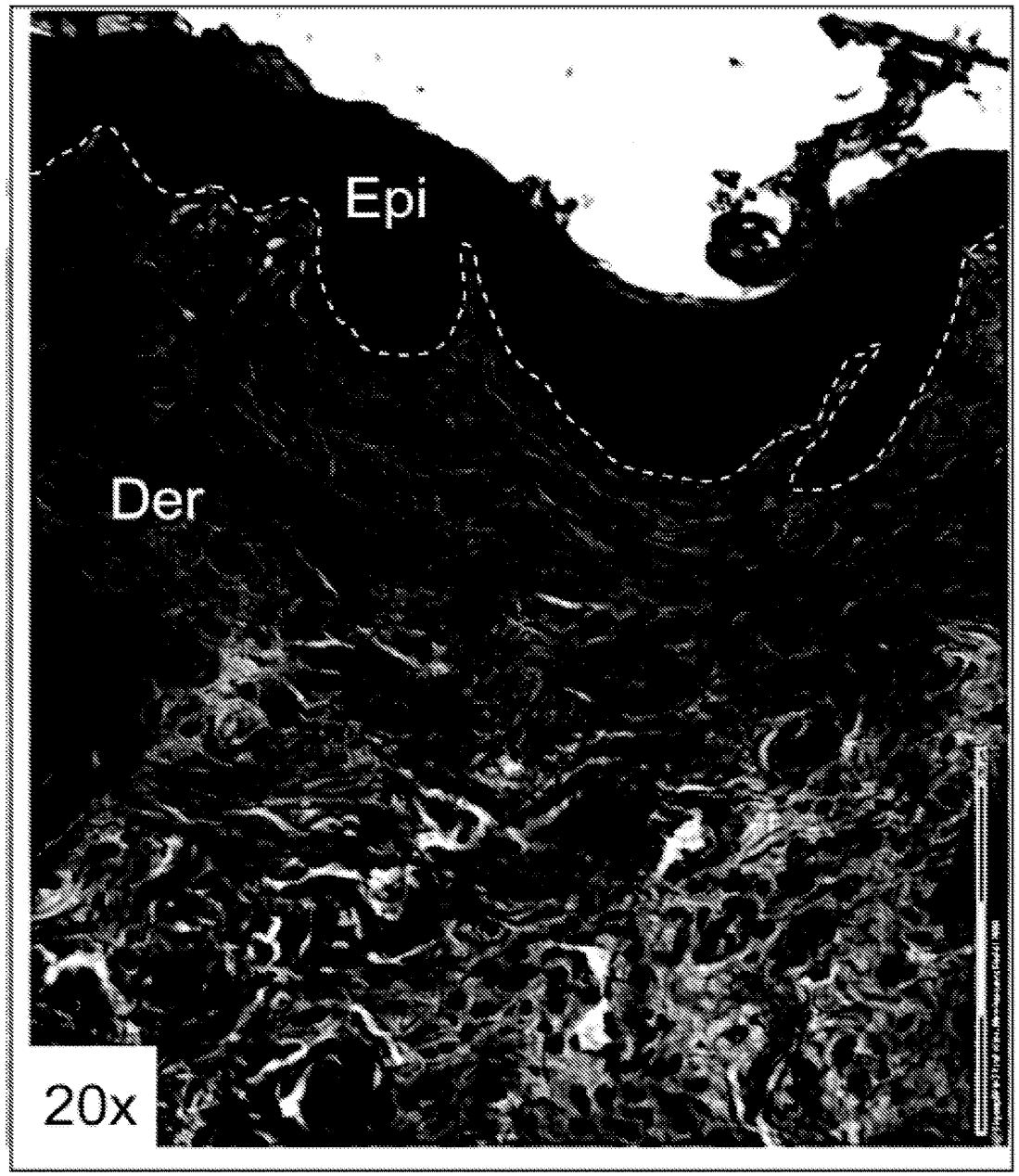
FIG. 10 is a 20× micrograph of a skin tissue sample from a subject exhibiting Type II periorbital dyschromia.

The skin tissue sample shown in FIG. 10 is a sample from a test subject classified as exhibiting Type II periorbital dyschromia. The Fontana-Masson positive deposits that can be seen in the dermis of the Type I sample of FIG. 9 are absent from the dermis of the Type II sample in FIG. 10. Thus, the underlying biological causes of Type I and Type II periorbital dyschromia may be different from one another, which is important since products and treatments suitable for one type of periorbital dyschromia may not suitable for another type. In particular, products and treatments for Type II periorbital dyschromia may not need to address the presence of melanin in the dermis.

Examination of the skin tissue samples taken from Type II individuals also showed a lack of melanin in the epidermis. Thus, it is also important to recognize that periorbital dyschromia may be influenced not only by hyperpigmentation (i.e., too much pigmentation), as suggested by some researchers, but surprisingly appears to be influenced by hypopigmentation (i.e., not enough pigmentation) as well.

Figure 11:
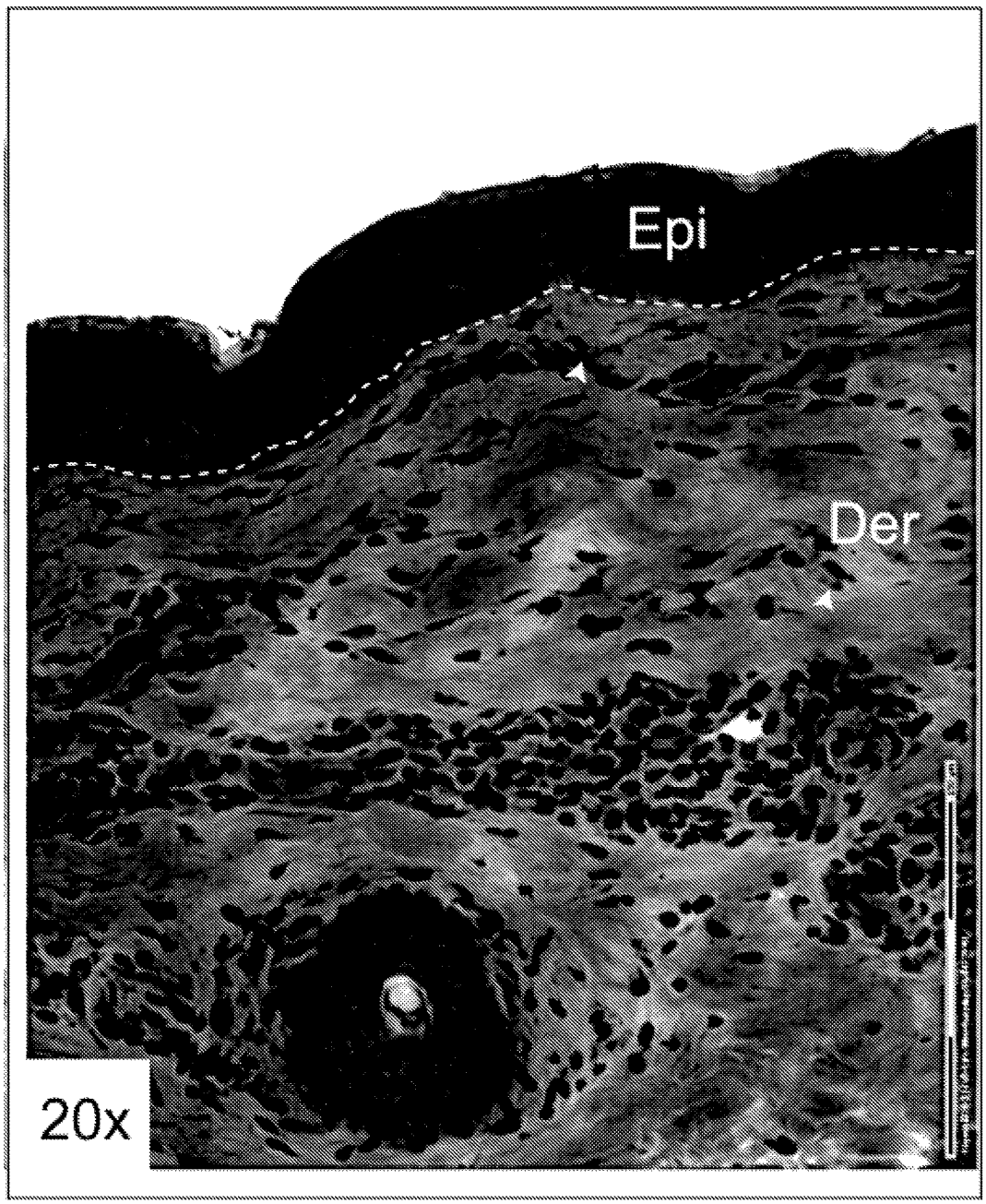
FIG. 11 is a 20× micrograph of a skin tissue sample from a subject exhibiting Type III periorbital dyschromia.

The skin tissue sample shown in FIG. 11 is a sample obtained from a test subject classified as exhibiting Type III periorbital dyschromia. As indicated by the white arrowheads in FIG. 11, there are Fontana-Masson positive deposits present around the nuclei of some cells in the dermis, but not as many as seen in the Type I sample shown in FIG. 9. It is believed, without being limited by theory, that Type III periorbital dyschromia may occur as a result of one or more factors from Type I and Type II periorbital dyschromia acting to produce periorbital dyschromia that exhibits at least some of the characteristics of both of these types. For example, the unexpected presence of melanin in the dermis may indicate that Type III periorbital dyschromia shares a common underlying cause with Type I, but less severe as evidenced by a lower amount of dermal melanin relative to Type I. Thus, products and treatments suitable for treating Type III periorbital dyschromia may need to address the underlying causes of Type I and/or Type II periorbital dyschromia, but perhaps not to the same extent. For example, a product suitable for treating Type I periorbital dyschromia that includes an active for addressing the presence of melanin in the dermis may not need to include as much of the active.

Biomarker

Figure 13:
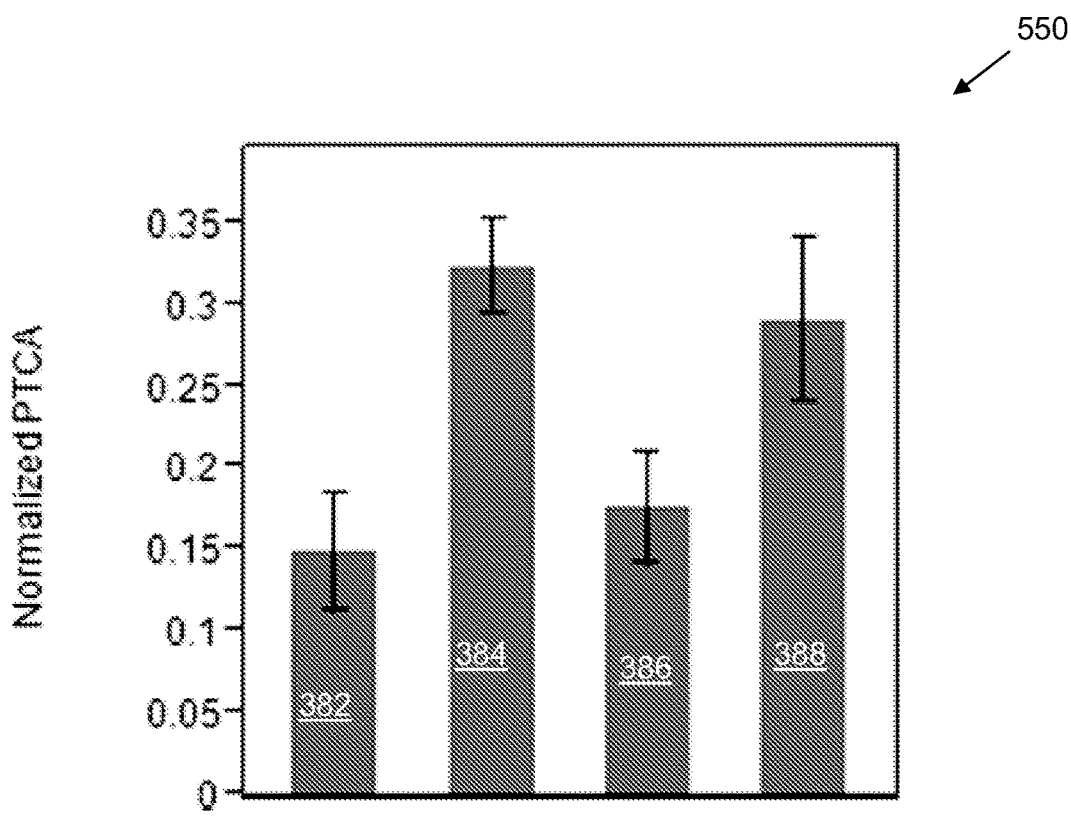
FIG. 13 illustrates the normalized PTCA amount measured for each type of periorbital dyschromia and a No Dyschromia condition.

Type I, Type II and Type III periorbital dyschromia may be distinguished from one another by collecting and analyzing the biomarkers present in periorbital skin. In particular, it has been found that the presence, absence and/or abundance of certain molecules in the epidermis of periorbital skin can be useful in distinguishing Type I, Type II and Type III periorbital dyschromia from one another. An example of such a molecule is pyrrole-2,3,5-tricarboxylic acid ("PTCA"), which is formed as a result oxidative degradation of eumelanin. It has been found that Type I and Type III periorbital dyschromia have higher PTCA levels than Type II, and that Type I may exhibit higher PTCA levels than Type III. FIG. 13 illustrates the comparison between PTCA levels of samples obtained from a subject classified as No Dyschromia 382, a subject who classified as Type I periorbital dyschromia 384, 2) a subject classified as Type II periorbital dyschromia 386, and 3) a test subject classified as Type III periorbital dyschromia 388. As illustrated in the chart 550 of FIG. 13, the PTCA levels of the Type I 384 and Type III 388 subjects was higher than the No Dyschromia 382 and the Type II subject 386 by a statistically significant amount. In contrast, the PTCA level of the Type II subject 386 was not higher than the No Dyschromia 382 by a statistically significant amount. PTCA levels herein are determined according to the Tape Stripping method described in more detail below.

Gene Expression

Type I, Type II and Type III periorbital dyschromia may be distinguished from one another by analyzing the expression of certain genes, individually or collectively, in the dermis and/or epidermis of periorbital skin. The gene expression signature of a periorbital skin sample may be obtained by any suitable means known in the art. For example, genetic material may be obtained from a tissue sample provide by a donor (e.g., full thickness skin biopsy that exhibits a condition of interest) and subsequently processed using any suitable technology such as, for example, microarray analysis or NextGen sequencing to provide a gene expression signature. The gene expression signatures of Type I, Type II and Type III periorbital dyschromia can then be compared to one another and/or a control to identify the differences in gene expression. Example 4 below provides an example of gene expression signatures associated with each of Type I, Type II and Type III periorbital dyschromia.

It may be desirable to distinguish the different types of periorbital dyschromia based on biological themes that correspond to the expression of certain genes, combinations of genes and/or gene families. That is, a technique sometimes referred to as theme analysis may be used to identify biological or phenotypic themes associated with the gene expression data that correspond to the different types of periorbital dyschromia. Theme analysis is a statistical analysis-based method for detecting biological patterns in gene expression data. The method uses an ontology of controlled vocabulary terms developed by the Gene Ontology ("GO") Consortium [Ashburner, M. et al. (2000) Gene ontology: tool for the unification of biology. The Gene Ontology Consortium. Nat Genet, 25, 25-29] that describe the biological processes, molecular functions and cellular components associated with gene products. Analysis involves statistical comparison of a regulated list of genes and a larger reference list of all the expressed genes, to determine if genes annotated to specific GO terms are significantly enriched in the regulated list. This analysis may reveal biological patterns when multiple genes associated with a given GO term occur on the regulated list at a frequency greater than expected by chance. Such analysis may be performed using Theme Extractor proprietary software and an algorithm that calculates a p-value of each ontology term. Data may be analyzed for statistical significance, for example, by the Fisher's Exact Test. Conventional approaches and statistical methods such as, for example, Gene Set Enrichment Analysis described by Subramanian, A., et al., in "Gene set enrichment analysis: a knowledge-based approach for interpreting genome-wide expression profiles," Proc. Natl. Acad Sci U.S.A, 102, 15545-155501 (2005) are suitable for conducting theme analysis herein.

Methods and Systems for Classifying Periorbital Discoloration

In some instances, the method herein includes indentifying a target portion of skin in the periorbital region of a person, evaluating the target skin portion based on the relevant characteristics described herein and classifying the person as having Type I, Type II or Type III periorbital dyschromia, if one or more characteristics associated with the relevant type of periorbital dyschromia are met. In some instances, the method may include classifying the type of periorbital dyschromia based solely on one of the foregoing distinguishing characteristics (i.e., visual characteristics such as RGB and/or RBX values, biomarkers, histology or gene expression). In some instances, the method includes classifying periorbital dyschromia based on a combination of two or more of the foregoing characteristics (e.g., visual and gene expression characteristics, visual and biomarker characteristics, or visual and histology characteristics).

Systems suitable for classifying periorbital discoloration herein may include an image capture device, an image analysis device, a means for communicating a type of periorbital dyschromia to a user of the system and, optionally, a set of instructions for using the system. The type of periorbital dyschromia may be selected from Type I, Type II and Type III as described herein. A user may also be classified as having No Dyschromia with the present system. The system may include a camera or similar device capable of capturing digital images of sufficient quality (e.g., greater than 8 megapixels per inch) for analysis by the image analysis device. The image capture device may be configured to store and/or transfer raw digital images and JPG digital image files. In some instances, the image analysis device may be a computer in electronic communication with the image capture device. The image analysis device should be capable of receiving and analyzing a raw digital image and/or a JPG image and converting the RGB color values of each pixel in the image to a more suitable color scale such as L*a*b* and, optionally, color and/or hue values (e.g., C* and h* values). Suitable image processing software (e.g., stored directly on the image analysis device or available for use or on the internal may be used by the image analysis device to process and/or analyze various aspects of the image. In some instances, it may be desirable to normalize the pixel colors of the image analysis system to reduce variation between images captured by different devices (e.g., using known color correction techniques and/or software). An exemplary method of normalizing an image analysis device is described in more detail below. Of course, it is to be appreciated that other suitable normalization techniques known in the art may be used.

The image analysis system may be configured to classify each pixel (or a predetermined number of pixels) into one of three groups (e.g., Type I, Type II and No Dyschromia) based on the color of the pixel. The image analysis system may then calculate the percent total number of pixels in each classification and determine which type of periorbital dyschromia is present or whether any periorbital dyschromia is present, based on the percentage of pixel types from each group. After determining the type of periorbital dyschromia present, if any, the system communicates the results of the analysis to the user, for example, visually via a monitor or television, audibly via a speaker or by any other suitable communication means known in the art.

In some embodiments, it may be desirable to place the system in a commercial environment such as a retail store to enable consumers to self-diagnose. In this way, a consumer would know which type of periorbital discoloration they might have and can select the appropriate cosmetic product to treat it.

Test Methods

Visual Classification Method

This method provides a suitable means to visually evaluate and classify periorbital dyschromia using expert graders. The visual evaluation can be done in-person as well as from images (e.g., cross-polarized images).

In-Person Grading

Prior to visual evaluation, the subjects are asked to wash their face and remove any make-up, especially eye make-up. The hair of the subject is covered with a hairnet and the head and shoulders of the subject are covered with black cloth. The subjects are asked to sit between two sets of lights that illuminate each side of their face without casting shadows or causing shine in the area of the eye. The expert grader assesses the subjects from a distance of approximately 60 cm, during which time subjects are asked to relax and refrain from making any facial expressions. The expert grader evaluates area, contrast and color of the periorbital region of the subject when classifying.

Image Grading

When visually evaluating and classify periorbital dyschromia from images, it may be desirable to capture an image of the region of interest of the test subject. To capture an image, prepare the subject by covering the hair of the subject with a hairnet and covering the head and shoulders of the subject with a black cloth. All jewelry that can be seen in an image is removed. The subject is seated on the adjustable stool and rotated towards the chin rest. The operator adjusts the stool such that the subject's chin rests comfortably on the chin rest. Front view images are captured using the Cross Polarized lighting modality. The images are evaluated in a dark room using professional color calibrated LCD monitors such as LACIE brand monitors. Graders are positioned approximately 60 cm from the monitor. Attributes such as area, intensity, contrast, color and continuity are evaluated for each subject.

Imaging Method

This method provides a suitable means for capturing a reproducible and analyzable image. Any suitable image capture device along with imaging software and other associated ancillary equipment (e.g., computer and lights) may be used. A particularly suitable imaging system is the Visia-CR® brand imaging system, available from Canfield Scientific, New Jersey. The Visia® brand imaging system incorporates a Canon® brand EOS-1Ds Mk III SLR camera, which includes a CMOS sensor and provides 21.1 Mega pixel resolution (14-bit A/D converter).

Images may be collected under different lighting modalities using standard light, UV, cross-polarization, parallel-polarization or a combination of these. For example, the values and ranges described herein are reported using a (D65/2) light source. One skilled in the art will appreciate that these values can be reported at a wide range of different illuminations (D50, D75, Illuminant A, F2, F7, F11, TL84, etc. or 2 or 10 degree observer) according to well known conversion methods, and when such conversions occur, the color values will typically change accordingly. In other words, even though the actual limits and/or ranges may change based on the conditions under which the image is captured, similar relationships among the values and ranges will still be seen. For example, if the camera has lower spectral sensitivity in the red channel than the camera described herein, the R channel response may be lower and the corresponding L*a*b*C*h* ("LabCh") color values will be different, which in this case may result in lower a* values, higher b* values, and/or higher hues. Accordingly different camera sensitivities, lightings and relevant exposures are contemplated by the method herein, and the actual limits and/or ranges disclosed herein may vary according to the particular circumstances in which the image is captured without departing from the scope of the systems and/or methods described herein.

In preparation for image capture, test subjects are required to wash their faces and wait for at least 15 minutes to let their face dry. The hair of the subject is covered with a hairnet and the head and shoulders of the subject are covered with a black cloth. All jewelry that can be seen in an image area of interest is removed. The subject is positioned such that the subject's chin is resting comfortably on the chin rest of the imaging system, and a front image of the face (as opposed to a left-side or right-side image) can be suitably captured by the image capture device. After the subject is positioned, one or more images are captured (e.g., between 1 and 24, 2 and 20 or even between 3 and 15) with the subject's eyes open. It can be important to ensure that the subject's eyes are open when the image is captured, otherwise the closed upper eyelid may cause an inaccurate pigmentation reading. The captured image(s) are processed by converting the raw image to a .jpg file format.

Figure 14:
FIG. 14 illustrates an example of a masked region corresponding to Zone 1.
Figure 15:
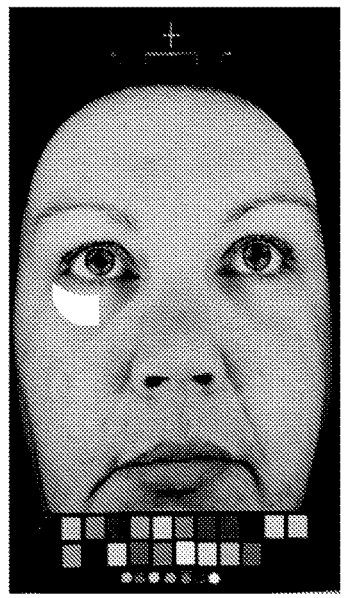
FIG. 15 illustrates an example of a masked region corresponding to Zone 2.
Figure 16:
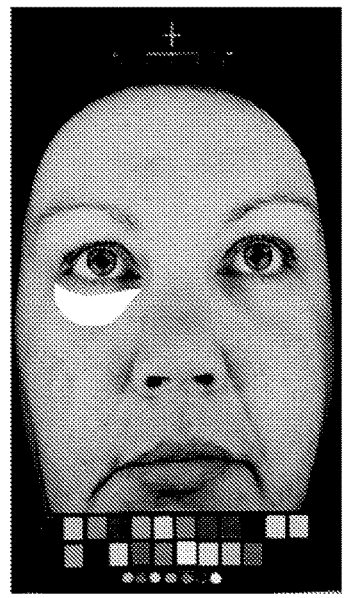
FIG. 16 illustrates an example of a masked region corresponding to Zone 4.
Figure 17:
FIG. 17 illustrates an example of a masked region corresponding to the cheek.
Figure 18:
FIG. 18 illustrates an example of a masked region corresponding to the cheek.

Next, the .jpg format image is analyzed by a computer with suitable image analysis software. In some instances, it may be desirable to analyze only a portion of the image (e.g., Zone 1, 2 and/or 3 of the periorbital region). The portion of the image to be analyzed may be "masked," for example, as shown in FIGS. 14 to 18, using image editing software such as Photoshop® or ImageJ®. The masked region can then be isolated and analyzed as a separate image. FIG. 14 illustrates an example of a masked region corresponding to Zone 1, which is referred to herein as "Mask A." FIG. 15 illustrates an example of a masked region corresponding to Zone 2, which is referred to herein as "Mask B." FIG. 16 illustrates an example of a masked region corresponding to Zones 1 and 2, which is referred to herein as "Mask C." FIGS. 17 and 18 both illustrate an example of a masked region corresponding to the cheek. It is to be appreciated that the image need not necessarily be masked for suitable analysis, and in some instances the entire image may be analyzed. In some instances, it may be desirable to reduce the size of the image, mask and/or region of interest by several pixels (e.g., between 5 and 15 pixels) around the outer edge of the image where some shadowing may occur.

In some instances, it may be desirable to convert some or all of the RGB values in the image or a portion thereof to LabCh values. The LabCh values can be calculated using a suitable RGB conversion tool at D65 Illuminant and 2 degree observer (i.e., D65/2). This conversion can be performed by software installed on the computer or a suitable conversion tool may be found online. The conversion from RGB values to LabCh values can be performed on the entire image, a portion thereof or on one or more individual pixels. The resulting LabCh values may be averaged to provide average values for the image, mask or region of interest.

Figure 20:
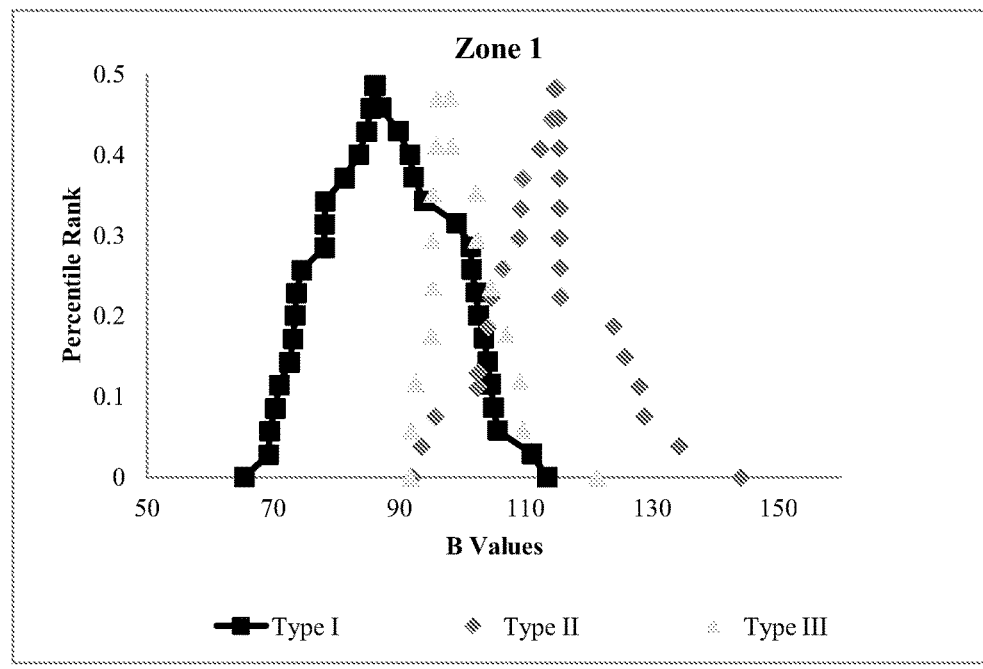
FIG. 20 is a comparison of the B values for different types of periorbital dyschromia in Zone 1.
Figure 21:
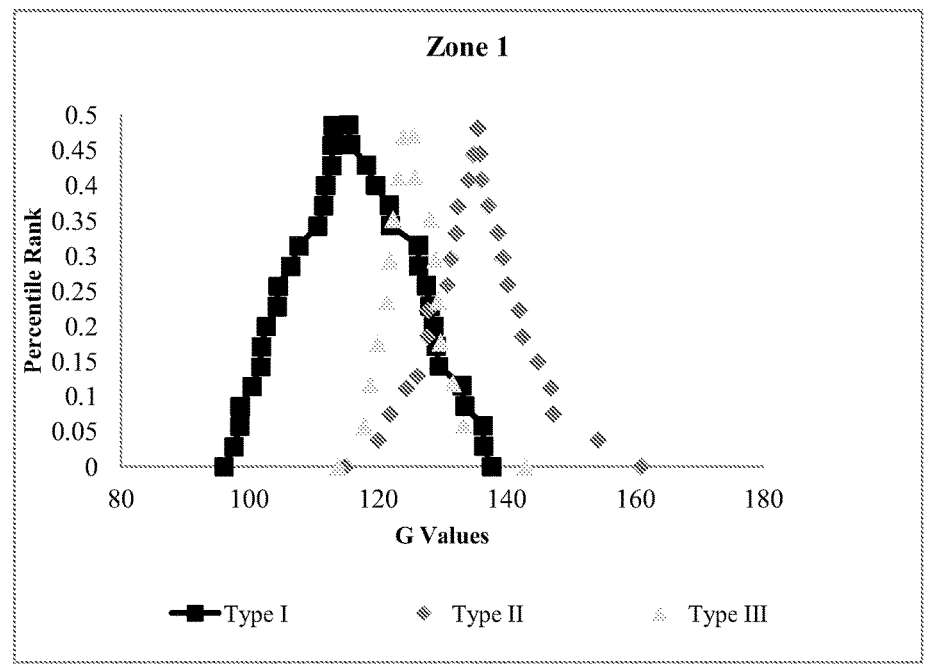
FIG. 21 is a comparison of the G values for different types of periorbital dyschromia in Zone 1.

In some instances, the pixels may be analyzed individually and each pixel classified as corresponding to a particular type of periorbital dyschromia based on one or more of the LabCh values. When analyzed individually, the pixels may be analyzed according to their distribution across the different types of periorbital dyschromia. An example of classifying periorbital dyschromia based on individual pixel distributions is described below in Example 2. Since color may be perceived as being relative, depending on, for example, which instruments and/or imaging system is used, it can be important to color correct the masked region for each subject using a suitable color correction technique (e.g., according to International Color Consortium standards and practices), which helps make the color determination by the system less instrument specific. In some instances, it may be desirable to normalize the color in a region of interest (e.g., a masked region) to the basal skin tone of a nearby region (e.g., cheek). For example, the basal skin tone of the cheek may be obtained by masking a region of interest in the cheek (e.g., as illustrated in FIG. 20 or 21) and converting the RGB values in the masked region to L*a*b*C*h* values as described above. The resulting basal skin tone values for the cheek may then be subtracted from the corresponding values in the region of interest to provide normalized values. Color normalization may be performed on the entire region of interest (e.g., an average value for the ROI) or on a pixel by pixel basis for some or all of the pixels in the ROI, which may be 200,000 or more pixels. The following formula provides an illustration of color normalization.

$$DL1 = Lpixel1 - Lcheekave$$

$$DC1 = Cpixel1 - Ccheekave$$

$$Dh1 = hpixel1 - hcheek\ ave$$

Where DL, DC and Dh are the normalized L*, C*, and h* values, respectively, of a pixel in the mask region; Lpixel, Cpixel and hpixel are the respective L*, C* and h* values of the pixels as determined from the image analysis; and Lcheekave, Ccheekave and hcheekave are the respective average L*, C* and h* values determined for the cheek.

Biopsy Method.

The biopsy method provides a suitable means for collecting, processing, storing and staining skin tissue samples. The biopsy also provides a suitable means for analyzing the skin samples for histological features associated with the different types of periorbital dyschromia. It is to be appreciated that certain portions of the method may refer to particular tools, equipment, or materials and the use thereof, but, unless indicated otherwise, one of ordinary skill in the art will recognize that equivalent tools, equipments and/or materials and the uses thereof may also be employed without departing from the scope of this method.

Sample Collection.

Skin tissue samples herein may be collected by means of a biopsy, which involves the physical removal of skin tissue from a subject. Biopsy samples collected for use herein may be removed according to any safe and aseptic biopsy method known in the art. For example, the biopsy samples may be collected from a living subject by a physician using conventional, aseptic techniques, and then flash frozen in liquid nitrogen and stored at −80° C. Eyelid biopsy sample collection involves the removal of skin tissue (down to the fatty layer) with, for example, a small elliptical surgical snip (e.g., Westcott™ brand scissors or equivalent). In at least some subjects, the elliptical shape of the incision allows for improved healing in the eyelid areas. Biopsy samples from other areas of skin on the body (e.g., cheek, forehead, arm or leg) may be obtained using, for example, a 2 mm sterile punch biopsy instrument. The size of the resulting punch biopsy sample is typically 2.0 mm in diameter and between 0.25 mm to 1.5 cm thick. In some instances, it may be desirable to suture the biopsy site.

Sample Storage

Biopsy samples should be frozen as soon as possible to minimize sample degradation Thus, it may be desirable to embed the biopsy samples in optimum cutting temperature ("OCT") tissue freezing medium (e.g., Tissue-tek® brand OCT tissue freezing medium available from Sakura Finetek, Calif.) within 5 minutes of biopsy collection and store the samples in a suitable freezer at a temperature of −80° C. or less.

Sample Sectioning.

Frozen biopsy samples may be sectioned using a Microm HM500 brand cryostat or equivalent. The cryostat should include a microtome capable of producing multiple slices of sectioned tissue sample ranging from 5 to 300 μm in thickness. For example, 14 μm thick sectioned tissue samples are suitable for use herein. Sectioned tissue samples may be placed on slides or other support medium suitable for further analysis (e.g., viewing under a light microscope).

Sample Staining.

Hematoxylin and Eosin stain are commonly used in pathology to get an overall assessment of the tissue and determine if structural abnormalities are present. Commercially available kits such as the Shandon Rapid Chrome Frozen Section Kit available from Thermo Scientific may be used according to the manufacturer's protocol for H&E staining of the sectioned tissue samples. Other staining techniques suitable for identifying histological features in a skin tissue sample (e.g., commercially available Fontana-Masson staining kits) may also be used herein in accordance with a manufacturer's protocol and/or another suitable method known in the art.

Tape Stripping Method

This method provides a suitable means of obtaining PTCA and/or other biomarkers from biological samples collected from test subjects. It has been discovered that biological material collected in this way may be correlated to a type of periorbital dyschromia (i.e., Type I, Type II, Type III or No Dyschromia). Samples may be collected by contacting a suitable adhesive-containing substrate ("tape strip") with a target skin surface such that biological material on and/or in the targeted skin portion adheres to the adhesive. Examples of suitable tape strips for use herein include D-Squame® brand polyacrylate ester adhesive tape (available from CuDerm; Dallas Tex.), Durapor, Sebutape™, and Tegaderm™ brand tape, duct tape (e.g., 333 Duct Tape, Nashua tape products), Scotch® brand tape (3M Scotch 810, St. Paul, Minn.), Diamond™ brand tape (The Sellotape Company; Eindhoven, the Netherlands), Sentega™ (polypropylene tape, Sentega Eiketten BV, Utrecht, The Netherlands).

The tape strips are digested with a suitable quantity and concentration of hydrogen peroxide to obtain PTCA from eumelanin. PTCA and its stable-isotope-labeled internal standard, PTCA-$^{18}$O, are then isolated from the digest by a liquid-liquid extraction procedure. The extracted analyte is subjected to reverse-phase, high-performance liquid chromatographic ("HPLC") analysis on a Waters Atlantis dC18 (3 μm 2.1×100 mm) or equivalent. Detection and quantitation of the PTCA is by tandem mass spectrometry (MS/MS) operating under multiple reaction monitoring conditions, as described in more detail below. Calibration standards are used to quantitate extracted Quality Control samples and unknown Study Specimens. The nominal range of quantitation is 0.15 to 100 ng of PTCA per sample. The concentration of PTCA is determined in the tape strip extract and then converted into total mass/tape strip by multiplying by the extraction volume. The squame scan total protein content found on the tape strips and extracts is determined and the final results are reported as total mass of analyte (ng or μg) per total weight of protein (μg) per sample. Specimen concentrations are determined by back-calculation using a weighted (1/x2) quadratic regression of a calibration curve generated from spiked matrix standards.

Sample Collection

A suitably sized tape strip (e.g., 14 mm diameter (circular) D-Squame® brand polyacrylate ester adhesive tape) is placed on a clean area of the target skin surface (e.g., periorbital region and/or cheek) and adequate pressure is applied to obtain the sample but not cause discomfort to the subject. The tape strip sample is then stored in a suitable storage container (e.g., storage tray or tube) until subjected to the digestion process.

PTCA Analysis

The tape strip sample is carefully removed from the storage container using tweezers. The tape strip sample is curled such that the adhesive-side faces inward and the non-adhesive side faces outward to reduce the possibility of contaminating the skin sample contained on the adhesive side of the tape. The curled tape strip sample is placed as deeply as possible into a 2 mL-polypropylene analysis tube in preparation for extraction of the biological material. The tape strip sample may be transferred to the analysis tube on the day of extraction or samples may be placed on storage plates and transferred to the 2 mL analysis tubes prior to extraction.

The tape strip sample is transferred from the 2 mL analysis tube to a 4 mL cryogenic Nalgene tube. A matrix blank is also prepared. The blank acts as a control and undergoes the sample process as the samples, but does not include a tape strip sample. 0.900 mL of 2 M ammonium hydroxide and 0.900 mL of 6% hydrogen peroxide are added to each of the Nalgene tubes, capped and vortexed. The tubes are placed on a rocker to incubate for three hours at 200 Mot/minute. The tubes are removed from the rocker and carefully uncapped to release any pressure that may build up during incubation. The liquid contents of each 4 mL Nalgene tube are transferred to separate 15 mL conical tubes. The tape strip is discarded and not transferred to the 15 mL conical tube. 32 μL of 10% sodium bisulfite is added to each 15 mL conical tube, capped and vortexed. Add 50 μL internal standard solution, cap and vortex. Internal standard solution is prepared as follows:

- Using the appropriate Internal Standard Reference Standard (i.e., stable, isotope-labeled PTCA $^{18}$O) weigh approximately 5 mg of Internal Standard into a glass scintillation vial and record the weight to at least the nearest 0.01 mg. Add of the exact amount of 10 mM ammonium acetate solution to give exactly a 1.00 mg/mL solution of the compound according to the following equation:

$$\text{Volume(mL)} = \frac{\text{Mass of material(mg)}}{1.0 \text{ mg/mL}} \times \text{Purity} \times SCF$$

Where:
Purity=Decimal % purity assigned to the Analytical Reference Standard; and
SCF=salt correction factor.
- Cap with a polytetraflouroethylene-lined cap and mix thoroughly and sonicate to dissolve the compound. Store the resulting solutions at −70 C.

2.00 mL of methyl-tert-butyl ether, 1.00 mL of 37% HCL, and 1.00 mL of saturated ammonium sulfate are added to each tube. The tubes are capped and vortexed. Centrifuge the samples at 3,000 RPM for 15 minutes and then transfer 1.00 mL of the organic layer of each tube to separate liquid chromatography vials. Dry the vials down under nitrogen as is known in the art. Reconstitute the vials with 0.250 mL of ammonium acetate, cap and vortex. Analyze the samples by high-performance liquid chromatography (HPLC)/mass spectrometry (MS)/mass spectrometry (MS).

EXAMPLES

Example 1

This example illustrates how different types of periorbital dyschromia can be distinguished using the Visual Classification Method. The Munsell Book of Color, Matte Collection (Munsell Color, Inc.) nomenclature is used to describe the color appearance of the different types of periorbital dyschromia or the lack thereof. The basal skin tone in this example refers to overall tone of the skin on the cheek.

1. No Dyschromia: occurs when there is no discoloration present in the periorbital region, discoloration is present but the intensity is very low ("non-severe"), or the discoloration does not extend beyond the inner corner of the eye (e.g., into Zone 1).

2. Type 1 Periorbital Dyschromia: occurs when Zone 1, Zone 2 and Zone 3 of the periorbital skin region are affected with a "tanned-like" skin tone. The tanned-like appearance found on Type I periorbital dyschromia may result from a darkening of the periorbital skin and an increase of the chroma relative to the basal skin tone. In this scenario, the hue in the periorbital skin is similar to basal skin hue. The Munsell Book of Color, Matte Collection (Munsell Color, Inc.) nomenclature can be used to describe this visual classification. For example, a Caucasian female (i.e., Fitzpatrick skin type I to III) who has basal skin tone of 10R 7/4 according to the Munsell Color nomenclature (H V/C— which corresponds to "hue", "value" (i.e., darkness) and "chroma" respectively), will be classified as Type 1 when the periorbital skin V value is 6 or lower and C value is 5 or higher (e.g., 10R 6/5 10R6/6, 10R 5/5, 10R 5/6). In another example, a Caucasian female with basal skin tone 10R 7/4 will be classified as Type I when the periorbital skin value 2.5YR 5/5 or 2.5YR 5/6.

3. Type II Periorbital Dyschromia: occurs when Zone 1 of the periorbital skin is affected with a "bruised-liked" tone relative to the basal skin. Bruised appearance of the periorbital skin can be a result of a darkening of the skin accompanied by a decrease in chroma relative to the basal skin tone. In this case, the periorbital skin hue may be similar to basal skin hue. For example, using the Munsell Matte Color collection, a Caucasian female with a basal skin tone of 10R 7/4 may manifest a bruised appearance characteristic of Type II periorbital dyschromia when the V value for Zone I and/or II drops to 6 or below and the chroma value drops to 4 or below (e.g., 10R 6/3, 10R6/2, 10R 5/3, 10R 5/2). The bruised appearance characteristic of Type II periorbital dyschromia can also result when the periorbital skin gets darker, chroma decreases and red hues are present. A Caucasian female with a basal skin tone of 10R 7/4 will manifest bruised appearance of Type II periorbital dyschromia when the periorbital skin hue is 7.5R, V is less than 7 and Chroma is less than 4 (e.g., 7.5R 6/2, 7.5R 5/2 7.5R 6/3, or 7.5R5/3).

4. Type III Periorbital Dyschromia: may occur when elements of both Type I and Type II periorbital dyschromia are present. Type III is typically observed in Zone I and Zone 2 of the periorbital region, and may a display "bruised-like" and "tanned-like" appearance. The "bruised-like" and "tanned-like" appearances may be observed in the same or different periorbital Zones simultaneously. For example, a Caucasian female may exhibit Type III periorbital dyschromia when Zone I displays a bruised appearance and Zone II displays tanned appearance. Type III periorbital dyschromia can also occur when bruised and tanned appearance occur simultaneously in Zone I and Type III can also occur when Zone 1 and/or Zone 2 of the periorbital region are affected with "bruised-like" and "tanned like" appearance and Zone 3 is effected by either "bruised-like" or "tanned-like" appearance. Type III can also occur when there is a darkening in the periorbital skin when compared to basal skin such as the cheek with no change in chroma value. For a Caucasian female with basal skin tone 10R 7/4, Type III periorbital dyschromia may occur from a darkening in the skin with no change in chroma, can be represented, for example, by 10R 6/4, 7.5R 6/4.

Example 2

This example illustrates the distinctions between Type I, Type II and Type III periorbital dyschromia using imaging methods. Using the methods described herein, images were obtained from test subjects identified as having Type I, Type II, or Type III periorbital dyschromia, and the RGB values and B/G ratios from each of zones 1, 2 and 4 were determined for each subject. Zone 4 refers to the combination of Zones 1 and 2. The zones were masked as described in the imaging analysis method above. Zone 4 was masked as illustrated in FIG. 16. Side-by-side plots of the various RGB values and B/G ratios are illustrated in FIGS. 19 to 30. The percentile shown on the y-axis of the charts in FIGS. 19 to 30 represents the percentile ranking of each individual in the distribution. The data point at the $50^{th}$ percentile represents the median of the data set (i.e., the individual who was in the middle of the rank ordered population). The X-axis shows the average imaging value for the region analyzed. As can be seen in FIGS. 19-30, those individuals who fall generally in the middle of the population distribution (e.g., between the $25^{th}$ and $75^{th}$ percentile; the $33^{rd}$ and $67^{th}$ percentile; or the $40^{th}$ and $60^{th}$ percentile) exhibit color imaging values that can be used to distinguish the different types of periorbital dyschromia from one another.

Figure 19:
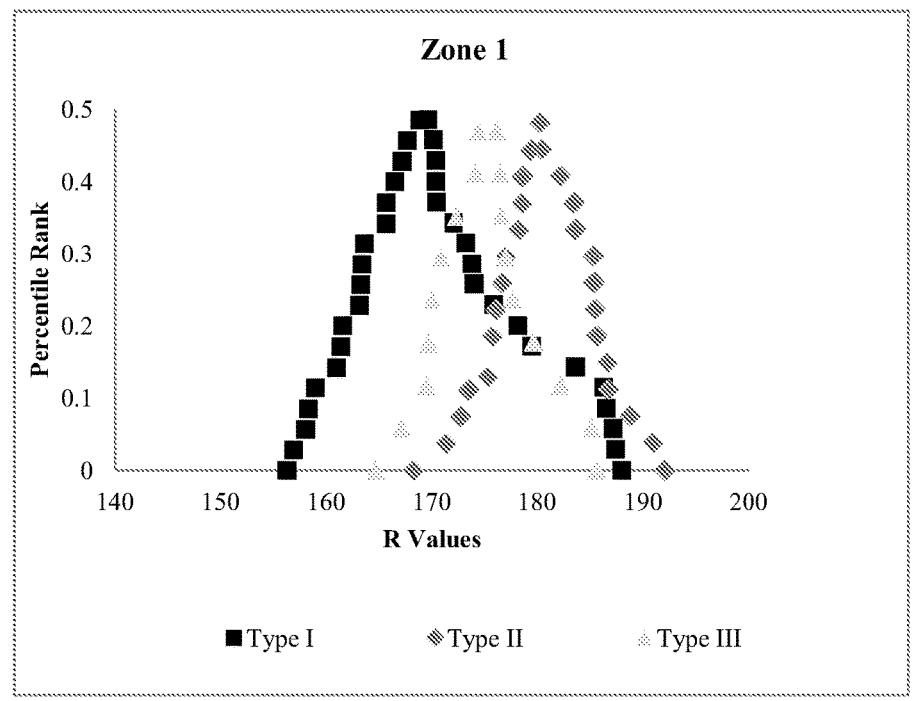
FIG. 19 shows a comparison of the R values for different types of periorbital dyschromia in Zone 1.
Figure 22:
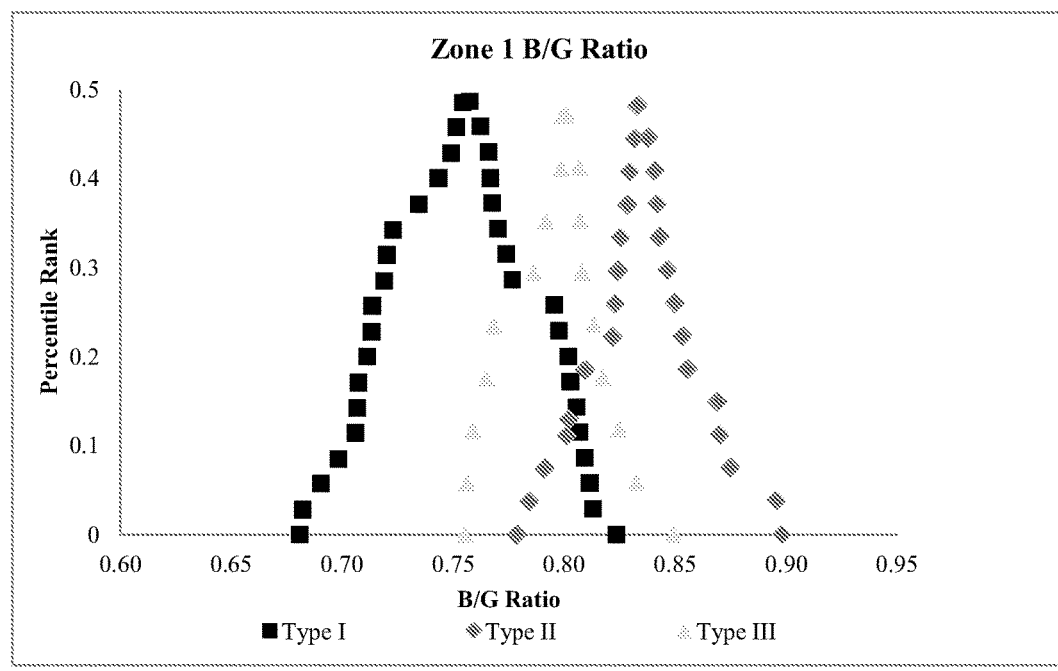
FIG. 22 is a comparison of the B/G ratios for different types of periorbital dyschromia in Zone 1.
Figure 23:
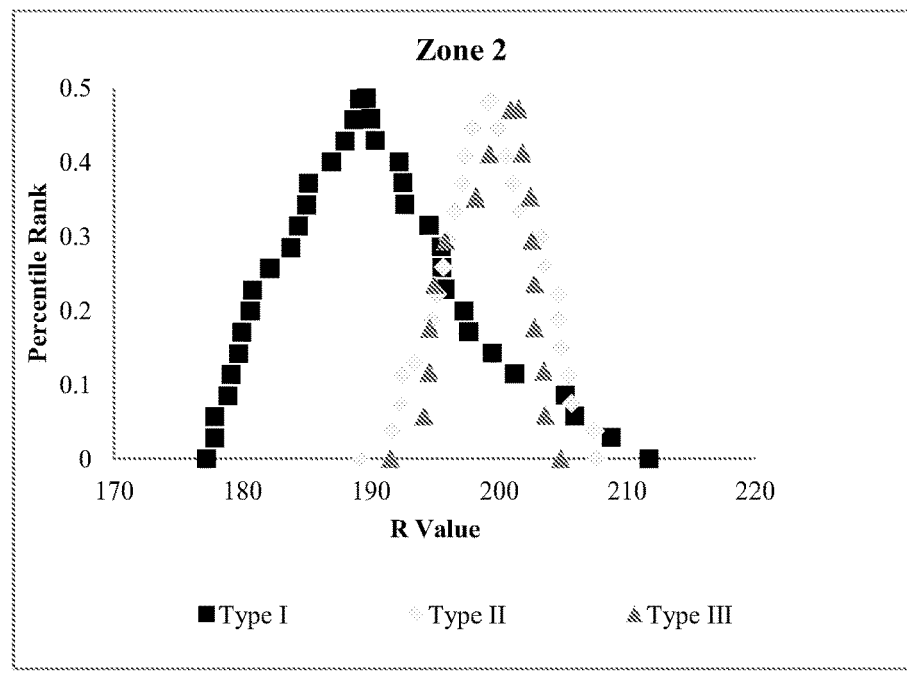
FIG. 23 is a comparison of the R values for different types of periorbital dyschromia in Zone 2.
Figure 24:
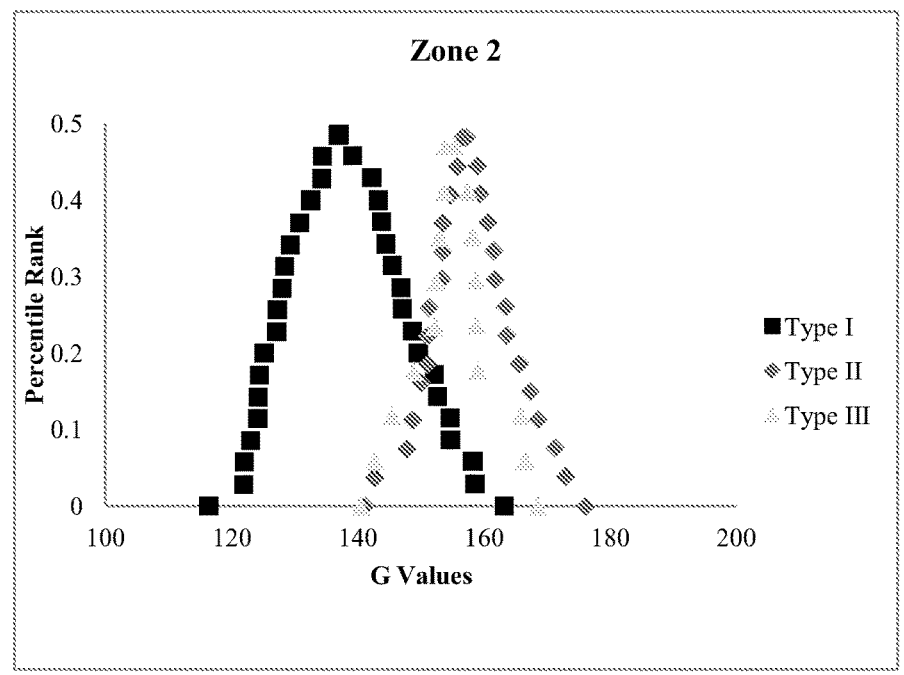
FIG. 24 is a comparison of the G values for different types of periorbital dyschromia in Zone 2
Figure 25:
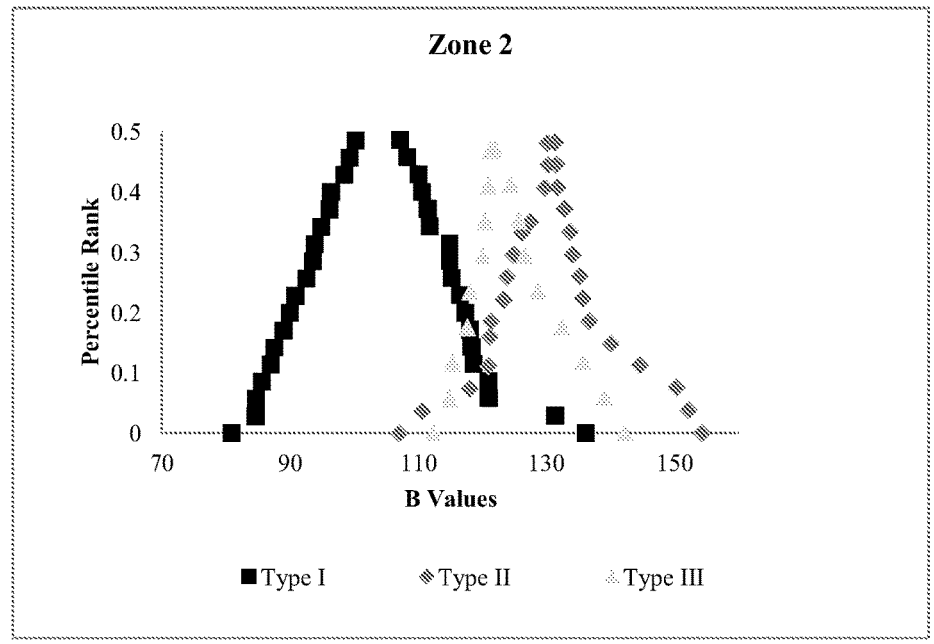
FIG. 25 is a comparison of the B values for different types of periorbital dyschromia in Zone 2.
Figure 26:
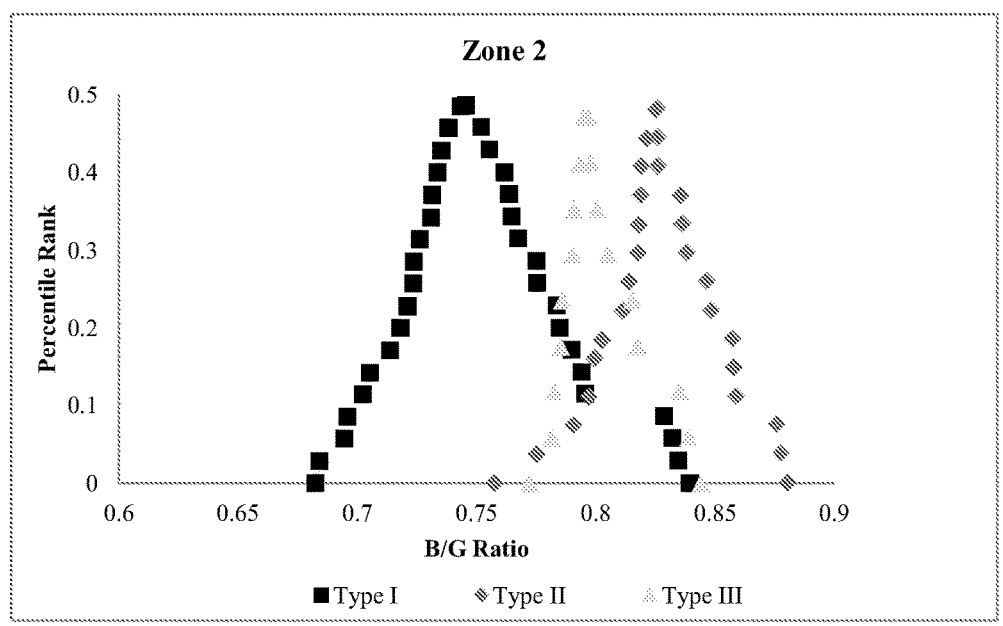
FIG. 26 is a comparison of the B/G ratios for different types of periorbital dyschromia in Zone 2.
Figure 27:
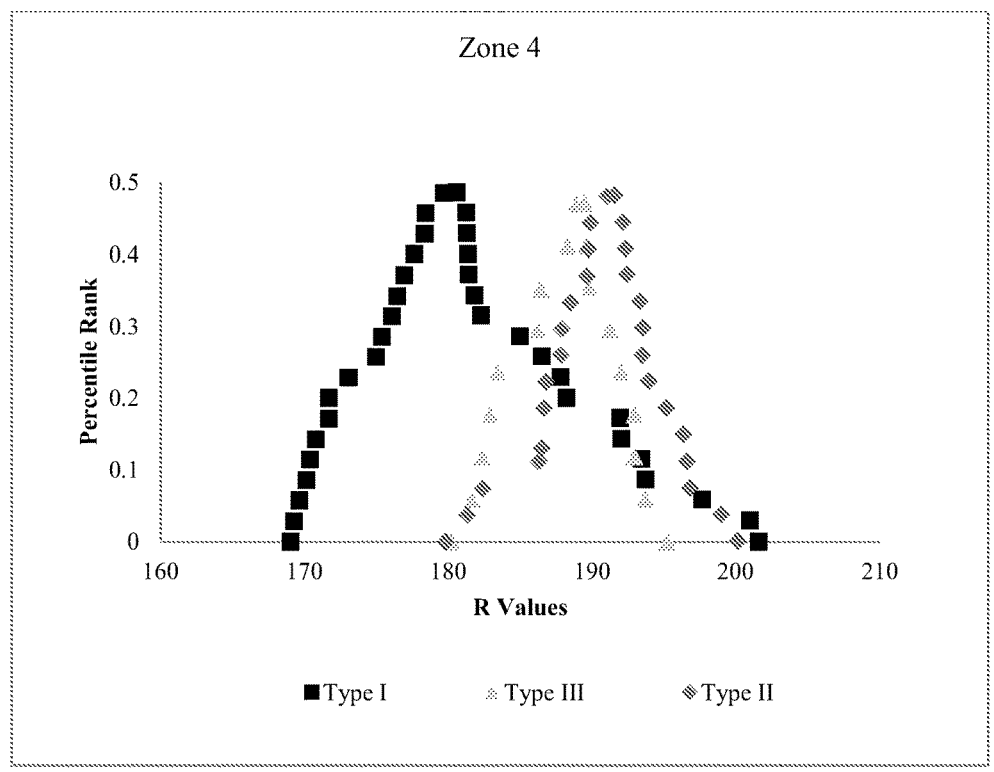
FIG. 27 is a comparison of the R values for different types of periorbital dyschromia in Zone 4 (i.e., Zones 1 and 2, in combination).
Figure 28:
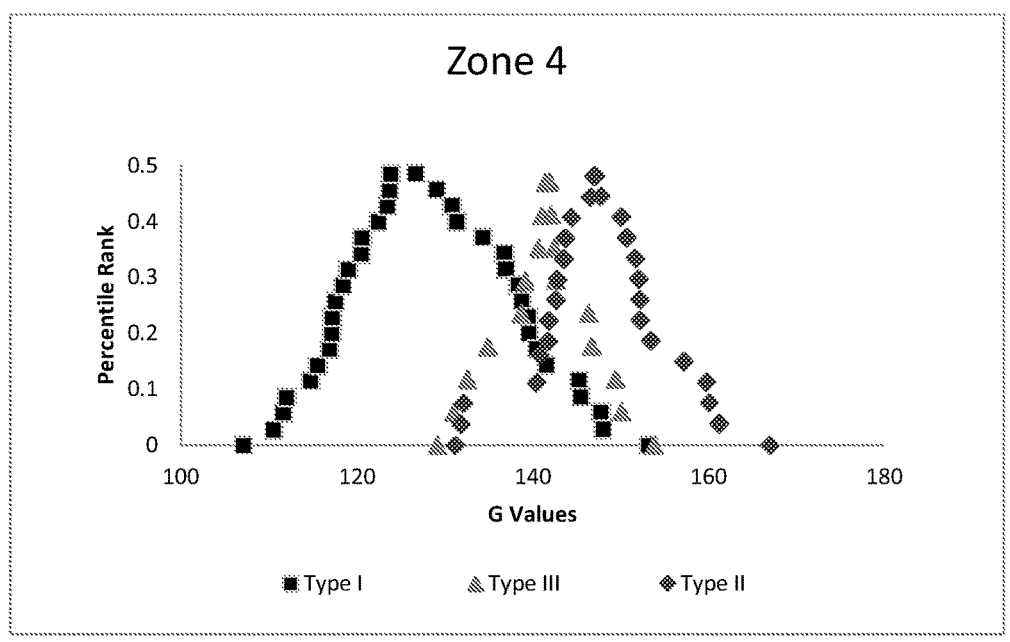
FIG. 28 is a comparison of the G values for different types of periorbital dyschromia in Zone 4 (i.e., Zones 1 and 2, in combination).
Figure 29:
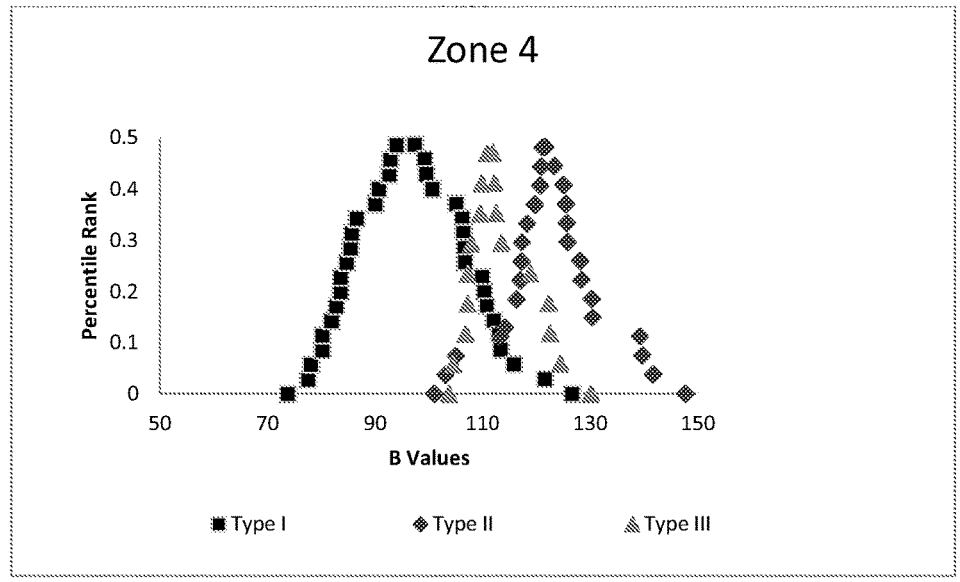
FIG. 29 is a comparison of the B values for different types of periorbital dyschromia in Zone 4 (i.e., Zones 1 and 2, in combination).
Figure 30:
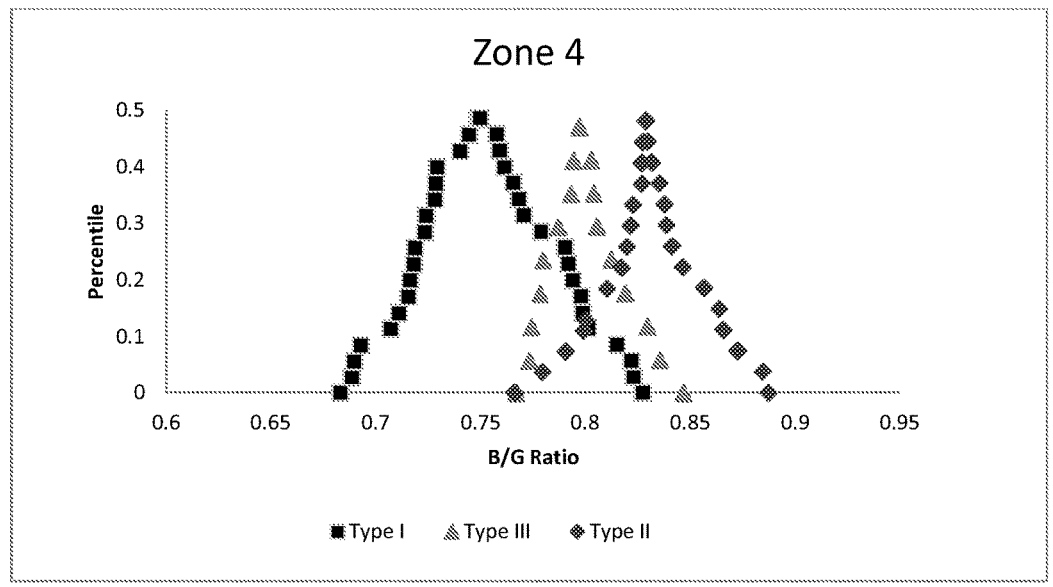
FIG. 30 is a comparison of the B/G ratios for different types of periorbital dyschromia in Zone 4 (i.e., Zones 1 and 2, in combination).

FIGS. 19-30 are side-by-side comparisons of graphical plots representing imaging values corresponding to Type I, Type II and Type III test subjects. FIG. 19 shows a side-by-side comparison of Zone 1 R values. FIG. 20 shows a side-by-side comparison of the Zone 1 B values. FIG. 21 shows a side-by-side comparison of the Zone 1 G values. FIG. 22 shows a side-by-side comparison of the Zone 1 B/G ratios. FIG. 23 shows a side-by-side comparison of the Zone 2 R values. FIG. 24 shows a side-by-side comparison of the Zone 2 G values. FIG. 25 shows a side-by-side comparison of the Zone 2 B values. FIG. 26 shows a side-by-side comparison of the Zone 2 B/G ratios. FIG. 27 shows a side-by-side comparison of the R values from Zone 4. FIG. 28 shows a side-by-side comparison of the B values from Zone 4. FIG. 29 shows a side-by-side comparison of the plots of the G values from Zone 4. FIG. 30 shows a side-by-side comparison of the plots of the B/G ratios from Zone 4.

Because skin is complex, there can be many different colors in a particular region of interest. Different people may appear to have some or all of the same colors present in particular area of skin, but the colors may be present at different percentages. And it is the distribution and/or preponderance of the different colors in the region of interest that drives how periorbital dyschromia is perceived. Thus, the images described in this Example were also analyzed on a pixel by pixel basis to determine if differences between different types of periorbital dyschromia could be observed. The RGB values for each pixel were converted to LabCh values as described in the imaging method above, and the L, C and h values were normalized to the cheek basal skin tone. The DL, Dc and Dh values of each pixel are classified as follows:

DL>−5: the pixel is not meaningfully darker than the nearby cheek skin (or it could even be lighter), these pixels were classified as No Dyschromia DL<−5 and DC>2: the pixel is both darker and more chromatic than the nearby skin. These pixels are classified as Type I.

DL<−5 and DC<2: the pixel is darker, but without a meaningful increase in chroma. These pixels are classified as Type II periorbital dyschromia.

After each pixel was classified, the distribution of the pixels in the masked region was determined by counting the number of pixels classified as each type of periorbital dyschromia (i.e., No Dyschromia, Type I and Type II) and dividing by the total number pixels in each mask to obtain percentages, (e.g., % Type I=# pixels classified as Type I divided by Total # pixels) Table 1 illustrates how the different types of periorbital dyschromia may be classified based on the observations from the pixel by pixel analysis of the images.

TABLE 4

| Pixel Distribution | Subject Classified as: |
|---|---|
| >36.4% classified as Type I | Type I |
| <9.6% classified as Type I; AND >21.2% classified as Type II | Type II |
| >9.6% but less than 36.4% classified as Type I; AND >20% classified as Type II. | Type III |
| <9.6% classified as Type I AND <21.2% classified as Type II. | No Dyschromia |

Example 3

This example further illustrates how imaging values can be used to distinguish Type I, Type II and Type III periorbital dyschromia. Using the methods described herein, images were obtained from test subjects identified as having Type I, Type II, or Type III periorbital dyschromia, and the color corrected imaging values for each of Mask A, Mask B and Mask C were determined for each image. Table 5 shows the resulting values.

TABLE 5

| Type I | | | |
|---|---|---|---|
| Imaging Value | Mask A | Mask B | Mask C |
| R | 153 | 167 | 161 |
| G | 108 | 123 | 116 |

TABLE 5-continued

| Type I | | | |
|---|---|---|---|
| Imaging Value | Mask A | Mask B | Mask C |
| B | 95 | 101 | 98 |
| B/G | 0.87 | 0.82 | 0.84 |
| L | 50 | 55 | 53 |
| a* | 16 | 14 | 15 |
| b* | 15 | 19 | 17 |
| Hue (h) | 43 | 53 | 49 |
| Chroma (C) | 22 | 23 | 23 |

TABLE 6

| Type II | | | |
|---|---|---|---|
| Imaging Value | Mask A | Mask B | Mask C |
| R | 161 | 176 | 169 |
| G | 119 | 135 | 128 |
| B | 108 | 116 | 112 |
| B/G | 0.91 | 0.86 | 0.88 |
| L | 54 | 60 | 57 |
| a* | 15 | 13 | 14 |
| b* | 12 | 17 | 15 |
| Hue (h) | 39 | 52 | 46 |
| Chroma (C) | 20 | 21 | 20 |

TABLE 7

| Type III | | | |
|---|---|---|---|
| Imaging Value | Mask A | Mask B | Mask C |
| R | 157 | 176 | 167 |
| G | 113 | 133 | 124 |
| B | 101 | 111 | 107 |
| B/G | 0.89 | 0.84 | 0.86 |
| L | 52 | 59 | 56 |
| a* | 16 | 13 | 14 |
| b* | 14 | 18 | 16 |
| Hue (h) | 41 | 54 | 48 |
| Chroma (C) | 21 | 23 | 22 |

This example illustrates the histological differences between No Dyschromia, Type I, Type II and Type III periorbital dyschromia. Biopsy samples were collected from upper eyelid, lower eyelid and the area of the face near the temple of fifty-five test subjects. The biopsy samples were collected, stored, sectioned and stained with H&E stain according to the Biopsy method above. An analysis of the sectioned and stained samples revealed the presence of deposits disposed around the nuclei of cells clustered together in the dermal region of the tissue sample. The deposits appeared brown in a color micrograph, and it is believed that the deposits are melanin. The samples were stained with Fontana-Masson stain and turned black (i.e., "Fontana-Masson positive deposits"), which indicates that the deposits may be melanin.

Figure 12:
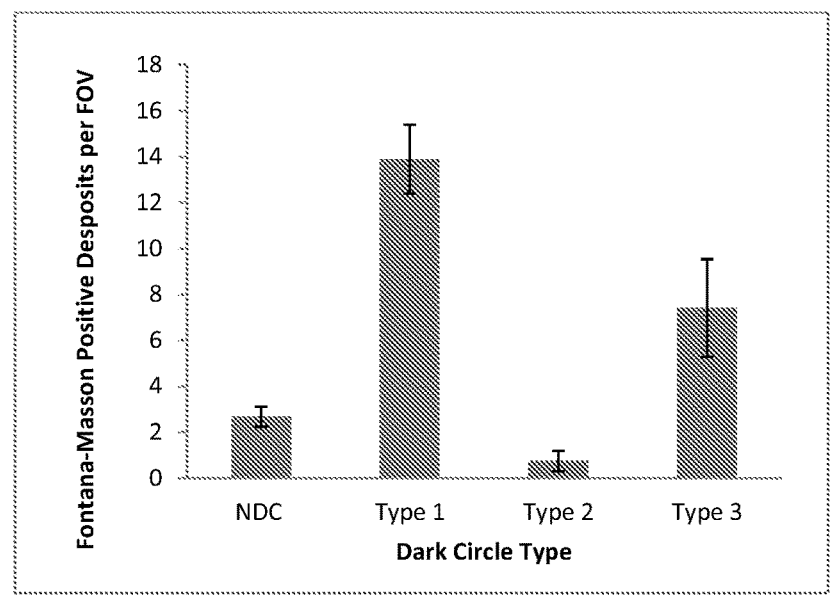
FIG. 12 illustrates the Fontana-Masson positive bodies observed per field of view for each type of periorbital dyschromia and a No Dyschromia condition.

Thirty biopsy samples representative of the four different classifications were selected at random for further analysis (6 non-dyschromia samples, 9 Type I sample, 9 Type II samples, and 6 Type III samples). The thirty samples were analyzed at 20× magnification under an Olympus® Model BX51TRF brand light microscope. For the analysis, a minimum of two tissue sections and 8 fields of view ("FOV"), which is defined as the area of tissue that can be observed under 20× magnification, are analyzed per subject. The analysis revealed that Type I and Type III periorbital dyschromia exhibited higher amounts of the Fontana-Masson positive deposits on the dermis than Type II and those subjects identified as not having severe periorbital dyschromia. The average number of Fontana-Masson positive deposits per field of view is provided in Table 2 below. FIG. 12 graphically depicts the results illustrated in Table 2.

TABLE 8

|  | No Dyschromia | Type I | Type II | Type III |
|---|---|---|---|---|
| Subject 1 | 2.88 | 15.00 | 0.87 | 13.6 |
| Subject 2 | 4.67 | 11.50 | 0.10 | 4.19 |
| Subject 3 | 1.69 | 22.45 | 0.00 | 2.35 |
| Subject 4 | 1.94 | 12.96 | 4.00 | 3.81 |
| Subject 5 | 2.58 | 11.50 | 0.38 | 6.33 |
| Subject 6 | 2.33 | 6.95 | 0.56 | 14.25 |
| Subject 7 |  | 10.58 | 0.07 |  |
| Subject 8 |  | 12.33 | 0.00 |  |
| Subject 9 |  | 21.78 | 0.50 |  |
| Average | 2.68 | 13.89 | 0.75 | 7.42 |
| STD DEV | 0.43 | 1.49 | 0.45 | 2.12 |

As can be seen in Table 8 and FIG. 12, the Fontana-Masson positive deposits distinguish the different types of periorbital dyschromia from each other and from the control. The chart in FIG. 12 illustrates this distinction based on the difference in the average number of Fontana-Masson positive deposits observed per FOV under 20× magnification.

Example 4

This example illustrates the differences in gene expression between No Dyschromia, Type I, Type II and Type III periorbital dyschromia. In this example, gene expression profiles and phenotype themes were determined from biopsy samples of female test subjects aged 18 to 45 who were classified as exhibiting Type I, Type II or Type III periorbital dyschromia by an expert grader. Thirteen subjects were classified as Type I periorbital dyschromia, fourteen subjects were classified as Type II periorbital dyschromia, seven subjects were classified as Type III periorbital dyschromia, and 8 test subjects were classified as No Dyschromia. The biopsy samples were collected, stored and sectioned according to the Biopsy method described above. The epidermis and dermis layers of the section biopsy samples were separated with a PALM Microbeam IV™ brand Laser-capture Micro dissection ("LCM") system (available from Carl Zeiss MicroImaging GmbH, Germany) in accordance with the manufacturer's instructions.

After separating the epidermal and dermal layers of the sectioned biopsy samples, each layer was subjected to RNA extraction. In this example, RNA was extracted from each of the epidermis and dermis layers by utilizing the Arcturs picopure kit according to the manufacturer's instructions. RNA quantification and quality assurance was performed using Agilence 2100 bioanalyzer. Of course it is to be appreciated that any suitable means of extracting RNA from a tissue sample known in the art may be used. The extracted RNA was then run on a GeneTitan U129 brand microarray to identify how certain genes were expressed in each sample. A statistical analysis of the microarray data was performed to derive the gene expression signatures. A general description of the statistical analysis is provided below. It is to be appreciated that while the statistical analysis below provides a suitable means of generating a gene signature from the microarray data, other statistical methods known in the art may also be suitable for use herein.

Filtering based on Present Calls

Filtering creates a list of potential genes for inclusion in the gene expression signature. For example, as a first filter step, at least 50% of the samples in one treatment group must have a "Present call" for each probe set. Present calls are derived from processing the raw microarray data and provide evidence that the gene transcript complementary to a probe set is actually expressed in the biological sample. The probes that are absent from all samples are likely to be just noisy measurements. It is important to filter out probe sets that do not contribute meaningful data to the signature. For all gene expression signatures in this example, the data was filtered for probe sets with at least 10% Present calls provided by the Affymetrix MAS 5 software.

Filtering According to a Statistical Measure

As a second filtering step, it may be desirable to use a suitable statistical measure such as, for example, p-values from a t-test, ANOVA, correlation coefficient, or other suitable model-based analysis. Limiting the gene signature list to genes that meet some reasonable cutoff (e.g., $p \leq 0.05$, 0.01, 0.001, or even $\leq 0.0001$ or less) for statistical significance compared to an appropriate control is important to allow selection of genes that are characteristic of the biological state of interest. This is preferable to using a fold change value, which does not take into account the noise around the measurements. For example, p-values may be chosen as the statistical measure and a cutoff value of $p \leq 0.05$ may be chosen. The t-statistic was used in this example to select the probe sets in the signatures because it provides an indication of the directionality of the gene expression changes (i.e. up- or down-regulated) as well as statistical significance.

Sorting the Probe Sets

All the probe sets are sorted into sets of up-regulated and down-regulated sets using the statistical measure. In this example, a t-test was used to compute p-values, the values (positive and negative) of the t-statistic are used to sort the list since p-values are always positive. The sorted t-statistics will place the sets with the most significant p-values at the top and bottom of the list with the less-significant p-values being placed towards the middle.

Creation of the Gene Expression Signature

Using the filtered and sorted list created, a suitable number of probe sets from the top and bottom are selected to create a gene expression signature that preferably has approximately the same number of sets chosen from the top as chosen from the bottom. For example, the gene expression signature created may have at least 10, 50, 100, 200, or 300 and/or less than 800, 600, or about 400 genes corresponding to a probe set on the chip. The number of probe sets approximately corresponds to the number of genes, but a single gene may be represented by more than one probe set. It is understood that the phrase "number of genes" as used herein, corresponds generally with the phrase "number of probe sets."

U.S. Publication No. 2012/0283112 titled "Systems and Methods For Identifying Cosmetic Agents For Skin Care Compositions" filed by Binder, et al., on Feb. 22, 2012 and U.S. Publication No. 2013/0261007 titled "Systems, Models and Methods for Identifying and Evaluating Skin-Active Agents Effective for Treating Conditions and Disorders of Skin Pigmentation," filed by Hakozaki, et al., on Mar. 27, 2012 disclose suitable nonlimiting examples of methods of generating a gene expression profile.

Tables 9 through 20 below show gene expression signatures associated with Type I, Type II or Type III periorbital dyschromia, as compared to the gene expression signature for No Dyschromia. The gene expression data was obtained by extracting RNA from lower eyelid biopsy samples obtained according to the biopsy method. Only genes that showed up-regulation or down-regulation with a p-value of 0.05 or less and fold change of 1.1 or more are shown. Table 9 shows the top 100 up-regulated genes expressed in the epidermis of subjects identified as having Type I periorbital dyschromia. Table 10 shows the top 100 down-regulated genes expressed in the epidermis of subjects identified as having Type I periorbital dyschromia. Table 11 shows the top 100 up-regulated genes expressed in the dermis of subjects identified as having Type I periorbital dyschromia. Table 12 shows the top 100 down-regulated genes expressed in the dermis of subjects identified as having Type I periorbital dyschromia. Table 13 shows the top 100 up-regulated genes expressed in the epidermis of subjects identified as having Type II periorbital dyschromia. Table 14 shows the top 100 down-regulated genes expressed in the dermis of subjects identified as having Type II periorbital dyschromia. Table 15 shows the top 71 up-regulated genes expressed in the dermis of subjects identified as having Type II periorbital dyschromia. Table 16 shows the top 100 down-regulated genes expressed in the dermis of subjects identified as having Type II periorbital dyschromia. Table 17 shows the top 100 up-regulated genes expressed in the epidermis of subjects identified as having Type III periorbital dyschromia. Table 18 shows the top 100 down-regulated genes expressed in the epidermis of subjects identified as having Type III periorbital dyschromia. Table 19 shows the top 100 up-regulated genes expressed in the dermis of subjects identified as having Type III periorbital dyschromia. Table 20 show the top 100 down-regulated genes expressed in the dermis of subjects identified as having Type III periorbital dyschromia.

TABLE 9

Type I Epidermis; Up-regulated

| GeneTitan_ID | Gene | Title | Public ID | p |
|---|---|---|---|---|
| 11719428_a_at | BTBD7 | BTB (POZ) domain containing 7 | AI580162 | 0.000259 |
| 11724297_a_at | BMP7 | bone morphogenetic protein 7 | NM_001719.2 | 0.000396 |
| 11715192_s_at | C7orf46 | chromosome 7 open reading frame 46 | g188219621 | 0.000446 |
| 11724759_s_at | CALM1 | calmodulin 1 (phosphorylase kinase, delta) | NM_006888.3 | 0.000486 |
| 11735610_a_at | RPS6KA5 | ribosomal protein S6 kinase, 90 kDa, polypeptide 5 | AF074393.1 | 0.000746 |
| 11758022_s_at | TNNI2 | troponin I type 2 (skeletal, fast) | AA728828 | 0.00151 |
| 11721260_a_at | WDR47 | WD repeat domain 47 | NM_001142550.1 | 0.001528 |
| 11727979_a_at | MAN2B2 | mannosidase, alpha, class 2B, member 2 | BC094773.1 | 0.002024 |
| 11753967_a_at | SLC6A2 | solute carrier family 6 (neurotransmitter transporter, noradrenalin), member 2 | AK301811.1 | 0.002393 |
| 11722090_a_at | EFNA4 | ephrin-A4 | NM_005227.2 | 0.002687 |
| 11758092_s_at | EFNA5 | ephrin-A5 | BE464799 | 0.002776 |
| 11717146_at | PTPN1 | protein tyrosine phosphatase, non-receptor type 1 | NM_002827.2 | 0.002876 |
| 11716283_at | PAPD7 | PAP associated domain containing 7 | NM_006999.3 | 0.003497 |
| 11746140_a_at | ARHGEF26 | Rho guanine nucleotide exchange factor (GEF) 26 | AF415176.1 | 0.003751 |
| 11724038_a_at | PTGS2 | prostaglandin-endoperoxide synthase 2 (prostaglandin G/H synthase and cyclooxygenase) | BC013734.1 | 0.003867 |
| 11723156_a_at | LSP1 | lymphocyte-specific protein 1 | NM_001013254.1 | 0.004011 |
| 11729840_s_at | ZCCHC2 | zinc finger, CCHC domain containing 2 | NM_017742.4 | 0.004086 |
| 11754302_a_at | ATP2A2 | ATPase, Ca++ transporting, cardiac muscle, slow twitch 2 | BM676899 | 0.004156 |
| 11754447_a_at | RPS6KA5 | ribosomal protein S6 kinase, 90 kDa, polypeptide 5 | BM968829 | 0.00436 |
| 11739724_a_at | ATP2B2 | ATPase, Ca++ transporting, plasma membrane 2 | AL138283 | 0.004438 |
| 11723075_a_at | BCL9L | B-cell CLL/lymphoma 9-like | AY296059.1 | 0.00493 |
| 11717385_a_at | MT1G | metallothionein 1G | NM_005950.1 | 0.005447 |
| 11758557_s_at | ZFP36L1 | zinc finger protein 36, C3H type-like 1 | AI758505 | 0.005544 |
| 11724628_a_at | MAT1A | methionine adenosyltransferase I, alpha | NM_000429.2 | 0.005576 |
| 11744955_a_at | ANXA1 | annexin A1 | AK296808.1 | 0.005629 |
| 11718966_at | NUFIP2 | nuclear fragile X mental retardation protein interacting protein 2 | BU533767 | 0.006124 |
| 11744953_a_at | ANXA1 | annexin A1 | BC034157.1 | 0.007553 |
| 11717387_x_at | MT1G | metallothionein 1G | NM_005950.1 | 0.007682 |
| 11727642_a_at | TRERF1 | transcriptional regulating factor 1 | AF111801.1 | 0.0078 |
| 11745806_a_at | AMMECR1L | AMME chromosomal region gene 1-like | AK095871.1 | 0.008163 |
| 11717514_a_at | ANXA1 | annexin A1 | NM_000700.1 | 0.008725 |
| 11744954_x_at | ANXA1 | annexin A1 | BC034157.1 | 0.009223 |
| 11743864_a_at | ATP2B1 | ATPase, Ca++ transporting, plasma membrane 1 | S49852.1 | 0.009249 |
| 11717927_at | FOXK2 | forkhead box K2 | NM_004514.3 | 0.009268 |
| 11717386_s_at | MT1G | metallothionein 1G | NM_005950.1 | 0.009421 |
| 11730080_x_at | IL28RA | interleukin 28 receptor, alpha (interferon, lambda receptor) | NM_170743.2 | 0.009429 |
| 11763297_x_at | CCDC76 | coiled-coil domain containing 76 | BQ614335 | 0.010042 |
| 11726119_at | RPGR | retinitis pigmentosa GTPase regulator | AK291832.1 | 0.01012 |

TABLE 9-continued

| Type I Epidermis; Up-regulated | | | | |
|---|---|---|---|---|
| GeneTitan_ID | Gene | Title | Public ID | p |
| 11739805_a_at | RASAL2 | RAS protein activator like 2 | AK075169.1 | 0.010243 |
| 11715190_s_at | C7orf46 | chromosome 7 open reading frame 46 | g188219617 | 0.010448 |
| 11726351_at | EFNA5 | ephrin-A5 | CB240929 | 0.010459 |
| 11738035_s_at | RTN4 | reticulon 4 | AK302741.1 | 0.010618 |
| 11724104_s_at | SGK3 | serum/glucocorticoid regulated kinase family, member 3 | NM_001033578.1 | 0.010735 |
| 11729396_a_at | NEK1 | NIMA (never in mitosis gene a)-related kinase 1 | Z25431.1 | 0.010781 |
| 11723592_at | LRRC8C | leucine rich repeat containing 8 family, member C | NM_032270.4 | 0.011015 |
| 11757982_s_at | KIF21A | kinesin family member 21A | N39407 | 0.011191 |
| 11731899_s_at | PPAT | phosphoribosyl pyrophosphate amidotransferase | D13757.1 | 0.01137 |
| 11726633_s_at | TRIM8 | tripartite motif-containing 8 | BC021925.1 | 0.011932 |
| 11725675_a_at | RORA | RAR-related orphan receptor A | AA034012 | 0.012081 |
| 11745021_a_at | MYC | v-myc myelocytomatosis viral oncogene homolog (avian) | K02276.1 | 0.012276 |
| 11758246_s_at | ARL4D | ADP-ribosylation factor-like 4D | BM719529 | 0.012438 |
| 11726634_a_at | MYST3 | MYST histone acetyltransferase (monocytic leukemia) 3 | NM_001099412.1 | 0.012468 |
| 11735421_a_at | NKD2 | naked cuticle homolog 2 (*Drosophila*) | AF358137.1 | 0.013343 |
| 11723821_a_at | SMURF2 | SMAD specific E3 ubiquitin protein ligase 2 | AY014180.1 | 0.013348 |
| 11733165_s_at | YIPF5 | Yip1 domain family, member 5 | NM_001024947.2 | 0.013814 |
| 11723169_s_at | FOXN2 | forkhead box N2 | NM_002158.3 | 0.014398 |
| 11728958_x_at | E2F8 | E2F transcription factor 8 | NM_024680.2 | 0.014717 |
| 11762525_s_at | | | AF339086.1 | 0.015079 |
| 11731645_a_at | CAMKK2 | calcium/calmodulin-dependent protein kinase kinase 2, beta | BC026060.2 | 0.016269 |
| 11730893_a_at | UBA6 | ubiquitin-like modifier activating enzyme 6 | EF623993.1 | 0.016784 |
| 11730360_at | CCDC126 | coiled-coil domain containing 126 | NM_138771.3 | 0.016798 |
| 11736426_s_at | CLIP4 | CAP-GLY domain containing linker protein family, member 4 | BM994685 | 0.017149 |
| 11725820_s_at | PAQR3 | progestin and adipoQ receptor family member III | NM_001040202.1 | 0.01721 |
| 11743411_a_at | RBM25 | RNA binding motif protein 25 | BG251218 | 0.017641 |
| 11718873_a_at | ATP2A2 | ATPase, Ca++ transporting, cardiac muscle, slow twitch 2 | NM_170665.3 | 0.018009 |
| 11739797_a_at | RFX2 | regulatory factor X, 2 (influences HLA class II expression) | NM_134433.2 | 0.018119 |
| 11739408_at | MLL3 | myeloid/lymphoid or mixed-lineage leukemia 3 | DN917896 | 0.018481 |
| 11734164_a_at | ARHGEF26 | Rho guanine nucleotide exchange factor (GEF) 26 | NM_015595.3 | 0.018897 |
| 11721039_a_at | SOLH | small optic lobes homolog (*Drosophila*) | NM_005632.2 | 0.019352 |
| 11721053_s_at | KLHDC5 | kelch domain containing 5 | NM_020782.1 | 0.01948 |
| 11753735_x_at | TMSB4X | thymosin beta 4, X-linked | BC101792.1 | 0.019698 |
| 11748149_a_at | FNBP1 | formin binding protein 1 | AK293743.1 | 0.019714 |
| 11728706_x_at | EMP2 | epithelial membrane protein 2 | DB374012 | 0.020127 |
| 11717989_a_at | SUN1 | Sad1 and UNC84 domain containing 1 | NM_001130965.1 | 0.020293 |
| 11722448_at | KCNMB4 | potassium large conductance calcium-activated channel, subfamily M, beta member 4 | AF160967.1 | 0.020548 |
| 11727512_at | UBN2 | ubinuclein 2 | CA775887 | 0.020981 |
| 11759962_at | TPRKB | TP53RK binding protein | AY643713.1 | 0.021007 |
| 11728603_a_at | CLDN23 | claudin 23 | NM_194284.2 | 0.0211 |
| 11743497_at | BMP2 | bone morphogenetic protein 2 | BX101090 | 0.021788 |
| 11718874_s_at | ATP2A2 | ATPase, Ca++ transporting, cardiac muscle, slow twitch 2 | NM_170665.3 | 0.0218 |
| 11721216_s_at | TMEM106B | transmembrane protein 106B | AA789109 | 0.021968 |
| 11718006_a_at | MYLIP | myosin regulatory light chain interacting protein | BC002860.2 | 0.02198 |
| 11719104_s_at | CPNE3 | copine III | BC066597.1 | 0.022194 |
| 11723130_a_at | ARHGEF7 | Rho guanine nucleotide exchange factor (GEF) 7 | NM_003899.3 | 0.022803 |
| 11757700_a_at | NDFIP2 | Nedd4 family interacting protein 2 | AA521251 | 0.022979 |
| 11718081_a_at | ATP2B4 | ATPase, Ca++ transporting, plasma membrane 4 | NM_001001396.1 | 0.023666 |
| 11748034_a_at | CMAH | cytidine monophosphate-N-acetylneuraminic acid hydroxylase (CMP-N-acetylneuraminate monooxygenase) pseudogene | D86324.1 | 0.02381 |
| 11740148_x_at | ZNF429 | zinc finger protein 429 | NM_001001415.2 | 0.023983 |

TABLE 9-continued

| | | Type I Epidermis; Up-regulated | | |
|---|---|---|---|---|
| GeneTitan_ID | Gene | Title | Public ID | p |
| 11716408_a_at | MET | met proto-oncogene (hepatocyte growth factor receptor) | NM_001127500.1 | 0.024171 |
| 11720082_at | CBX6 | chromobox homolog 6 | NM_014292.3 | 0.024178 |
| 11733076_x_at | PPP1R12A | protein phosphatase 1, regulatory (inhibitor) subunit 12A | AK314193.1 | 0.024224 |
| 11743280_a_at | WNK1 | WNK lysine deficient protein kinase 1 | BC013629.2 | 0.024246 |
| 11719028_a_at | PSD3 | pleckstrin and Sec7 domain containing 3 | DB314358 | 0.024644 |
| 11757869_s_at | AKAP13 | A kinase (PRKA) anchor protein 13 | BE504033 | 0.024753 |
| 11722290_a_at | ZBTB43 | zinc finger and BTB domain containing 43 | AI745225 | 0.024875 |
| 11743865_s_at | ATP2B1 | ATPase, Ca++ transporting, plasma membrane 1 | AI337321 | 0.025057 |
| 11734994_s_at | SKI | v-ski sarcoma viral oncogene homolog (avian) | NM_003036.3 | 0.025378 |
| 11731857_x_at | MT1H | metallothionein 1H | NM_005951.2 | 0.026268 |
| 11758247_x_at | ARL4D | ADP-ribosylation factor-like 4D | BM719529 | 0.026757 |
| 11731787_x_at | ERC1 | ELKS/RAB6-interacting/CAST family member 1 | NM_178037.1 | 0.026811 |

TABLE 10

| | | Type I Epidermis; Down-regulated | | |
|---|---|---|---|---|
| GeneTitan_ID | Gene | Title | Public ID | p |
| 11763233_x_at | TRAC | T cell receptor alpha constant | EU427374.1 | 0.000086 |
| 11750712_a_at | SEMA4A | sema domain, immunoglobulin domain (Ig), transmembrane domain (TM) and short cytoplasmic domain, (semaphorin) 4A | AK296693.1 | 0.000205 |
| 11743350_a_at | C15orf48 | chromosome 15 open reading frame 48 | CA309087 | 0.000277 |
| 11723817_at | ARHGAP29 | Rho GTPase activating protein 29 | BU620659 | 0.000376 |
| 11723854_at | SAMD9 | sterile alpha motif domain containing 9 | NM_017654.2 | 0.000398 |
| 11754862_a_at | RARRES2 | retinoic acid receptor responder (tazarotene induced) 2 | AK092804.1 | 0.000534 |
| 11729515_a_at | SLC26A9 | solute carrier family 26, member 9 | NM_052934.3 | 0.001204 |
| 11748896_s_at | CCRL1 | chemokine (C-C motif) receptor-like 1 | AK304461.1 | 0.001209 |
| 11761960_x_at | TRAV20 | T cell receptor alpha variable 20 | AY532913.1 | 0.001367 |
| 11741285_a_at | CCRL1 | chemokine (C-C motif) receptor-like 1 | BC069438.1 | 0.00144 |
| 11754482_a_at | PSMB1 | proteasome (prosome, macropain) subunit, beta type, 1 | BQ006450 | 0.001693 |
| 11754184_a_at | ALDH1A3 | aldehyde dehydrogenase 1 family, member A3 | BX538027.1 | 0.001883 |
| 11726829_at | TYW1B | tRNA-yW synthesizing protein 1 homolog B (S. cerevisiae) | NM_001145440.1 | 0.001956 |
| 11725368_at | LRG1 | leucine-rich alpha-2-glycoprotein 1 | NM_052972.2 | 0.001997 |
| 11723561_x_at | C11orf75 | chromosome 11 open reading frame 75 | NM_020179.2 | 0.002048 |
| 11734507_s_at | MECOM | MDS1 and EVI1 complex locus | AK292865.1 | 0.002142 |
| 11716805_s_at | PLEKHA2 | pleckstrin homology domain containing, family A (phosphoinositide binding specific) member 2 | NM_021623.1 | 0.002256 |
| 11754057_x_at | CRABP2 | cellular retinoic acid binding protein 2 | BT019827.1 | 0.00239 |
| 11737108_a_at | CCRL1 | chemokine (C-C motif) receptor-like 1 | NM_178445.1 | 0.002438 |
| 11720080_at | NTRK2 | neurotrophic tyrosine kinase, receptor, type 2 | NM_001007097.1 | 0.002467 |
| 11715767_s_at | ACAA2 | acetyl-CoA acyltransferase 2 | NM_006111.2 | 0.002477 |
| 11715670_a_at | IFITM1 | interferon induced transmembrane protein 1 (9-27) | NM_003641.3 | 0.002619 |
| 11735937_a_at | CD48 | CD48 molecule | NM_001778.2 | 0.002662 |
| 11746503_a_at | EHF | ets homologous factor | AF203977.1 | 0.00321 |

TABLE 10-continued

| | | Type I Epidermis; Down-regulated | | |
|---|---|---|---|---|
| GeneTitan_ID | Gene | Title | Public ID | p |
| 11736806_at | GABRA4 | gamma-aminobutyric acid (GABA) A receptor, alpha 4 | NM_000809.2 | 0.003627 |
| 11720157_at | GDA | guanine deaminase | AK295716.1 | 0.003854 |
| 11720132_a_at | SPIRE1 | spire homolog 1 (Drosophila) | BC125206.1 | 0.003917 |
| 11725832_s_at | OTUB2 | OTU domain, ubiquitin aldehyde binding 2 | NM_023112.3 | 0.004105 |
| 11717763_a_at | MGLL | monoglyceride lipase | BC006230.2 | 0.004157 |
| 11756683_a_at | CD1E | CD1e molecule | AK311643.1 | 0.004158 |
| 11728008_x_at | FUT3 | fucosyltransferase 3 (galactoside 3(4)-L-fucosyltransferase, Lewis blood group) | NM_000149.3 | 0.004308 |
| 11750244_a_at | MGLL | monoglyceride lipase | AK304844.1 | 0.004332 |
| 11724346_a_at | IFIH1 | interferon induced with helicase C domain 1 | NM_022168.2 | 0.004365 |
| 11750245_x_at | MGLL | monoglyceride lipase | AK304844.1 | 0.004459 |
| 11758377_s_at | TLR1 | toll-like receptor 1 | BU623316 | 0.004771 |
| 11740897_a_at | TREX2 | three prime repair exonuclease 2 | NM_080701.3 | 0.004847 |
| 11718077_s_at | MAPKAPK3 | mitogen-activated protein kinase-activated protein kinase 3 | NM_004635.3 | 0.004908 |
| 11763697_s_at | SNHG9 | small nucleolar RNA host gene 9 (non-protein coding) | AW958849 | 0.004956 |
| 11719591_s_at | GLTP | glycolipid transfer protein | NM_016433.3 | 0.005188 |
| 11715671_x_at | IFITM1 | interferon induced transmembrane protein 1 (9-27) | NM_003641.3 | 0.005216 |
| 11725641_at | EFHD2 | EF-hand domain family, member D2 | CB240768 | 0.005381 |
| 11727633_at | SLC16A10 | solute carrier family 16, member 10 (aromatic amino acid transporter) | BC066985.1 | 0.005429 |
| 11717764_x_at | MGLL | monoglyceride lipase | BC006230.2 | 0.005967 |
| 11750324_a_at | GAS7 | growth arrest-specific 7 | AK293755.1 | 0.006052 |
| 11735833_a_at | KIAA1199 | KIAA1199 | NM_018689.1 | 0.006555 |
| 11757367_s_at | HSPA7 | heat shock 70 kDa protein 7 (HSP70B) | BM677874 | 0.006575 |
| 11741263_s_at | LTBP1 | latent transforming growth factor beta binding protein 1 | M34057.1 | 0.006584 |
| 11723235_a_at | IFI44L | interferon-induced protein 44-like | AB000115.1 | 0.006657 |
| 11729692_a_at | SERPINB3 | serpin peptidase inhibitor, clade B (ovalbumin), member 3 | EU852041.1 | 0.006806 |
| 11727385_a_at | PCCA | propionyl CoA carboxylase, alpha polypeptide | NM_000282.2 | 0.006811 |
| 11729742_x_at | IFI27L2 | interferon, alpha-inducible protein 27-like 2 | NM_032036.2 | 0.006823 |
| 11731973_at | SCNN1G | sodium channel, nonvoltage-gated 1, gamma | NM_001039.3 | 0.00716 |
| 11743404_at | ZMAT2 | zinc finger, matrin-type 2 | BM450158 | 0.007256 |
| 11736058_s_at | C10orf32 | chromosome 10 open reading frame 32 | NM_001136200.1 | 0.007371 |
| 11715239_x_at | IFITM3 | interferon induced transmembrane protein 3 (1-8U) | g148612841 | 0.007374 |
| 11726154_at | CA6 | carbonic anhydrase VI | NM_001215.2 | 0.007409 |
| 11718850_a_at | SRPK1 | SRSF protein kinase 1 | AK299591.1 | 0.007419 |
| 11729693_at | SERPINB3 | serpin peptidase inhibitor, clade B (ovalbumin), member 3 | EU852041.1 | 0.007514 |
| 11755950_a_at | | coiled-coil domain containing 71 | AK098658.1 | 0.007621 |
| 11740349_at | RNASE7 | ribonuclease, RNase A family, 7 | BC112334.1 | 0.007692 |
| 11757300_s_at | ELOVL5 | ELOVL family member 5, elongation of long chain fatty acids (FEN1/Elo2, SUR4/Elo3-like, yeast) | AL576414 | 0.007702 |
| 11725310_at | CRISP3 | cysteine-rich secretory protein 3 | NM_006061.1 | 0.007915 |
| 11723490_at | GCLM | glutamate-cysteine ligase, | BC041809.1 | 0.008288 |
| 11757595_x_at | CRABP2 | cellular retinoic acid binding protein 2 | BU631189 | 0.008352 |
| 11752101_s_at | EIF2S1 | eukaryotic translation initiation factor 2, subunit 1 alpha, 35 kDa | BC002513.2 | 0.008373 |
| 11737496_a_at | CD200R1 | CD200 receptor 1 | NM_170780.2 | 0.008378 |
| 11749745_a_at | SRP68 | signal recognition particle 68 kDa | AK301100.1 | 0.008462 |
| 11718142_a_at | TTC27 | tetratripeptide repeat domain 27 | NM_017735.3 | 0.00876 |
| 11737432_a_at | PAPL | iron/zinc purple acid phosphatase-like-protein | BC136722.1 | 0.008796 |
| 11753762_x_at | KLK6 | kallikrein-related peptidase 6 | AY457039.1 | 0.008902 |
| 11725875_at | WDR66 | WD repeat domain 66 | NM_144668.4 | 0.008916 |

TABLE 10-continued

Type I Epidermis; Down-regulated

| GeneTitan_ID | Gene | Title | Public ID | p |
|---|---|---|---|---|
| 11729694_s_at | SERPINB4 | serpin peptidase inhibitor, clade B (ovalbumin), member 4 | EU852041.1 | 0.009199 |
| 11763184_at | IDE | insulin-degrading enzyme | BQ006777 | 0.009364 |
| 11737743_a_at | ARSF | arylsulfatase F | NM_004042.3 | 0.009395 |
| 11724785_x_at | MRPS18C | mitochondrial ribosomal protein S18C | BC005186.1 | 0.009553 |
| 11723899_a_at | DHRS9 | dehydrgenase/reductase (SDR family) member 9 | NM_005771.4 | 0.009689 |
| 11743805_s_at | MRPL42 | mitochondrial ribosomal protein L42 | DB379276 | 0.009847 |
| 11758083_s_at | HPGD | hydroxyprostaglandin dehydrogenase 15-(NAD) | AI743714 | 0.009851 |
| 11727995_a_at | SPINK5 | serine peptidase inhibitor Kazal type 5 | DQ149928.1 | 0.010277 |
| 11727208_x_at | DDHD1 | DDHD domain containing 1 | NM_030637.1 | 0.010297 |
| 11737431_x_at | PAPL | iron/zinc purple acid phosphatase-like protein | NM_001004318.2 | 0.010375 |
| 11720510_a_at | APOBEC3G | apolopoprotein B mRNA editing enzyme, catalytic polypeptide-like 3G | NM_021822.2 | 0.010471 |
| 11719503_a_at | DHX36 | DEAH (Asp-Glu-Ala-His) box polypeptide 36 | NM_020865.2 | 0.010702 |
| 11753152_x_at | CFLAR | CASP8 and FADD-like apoptosis regulator | AK297387.1 | 0.010705 |
| 11726289_at | GRAMD3 | GRAM domain containing 3 | BC008590.1 | 0.010722 |
| 11722661_at | NFE2L3 | nuclear factor (erythroid-derived 2)-like 3 | NM_004289.6 | 0.010893 |
| 11716743_s_at | TJP2 | tight junction protein 2 (zona occludens 2) | NM_004817.2 | 0.011228 |
| 11726894_a_at | IRAK3 | interleukin-1 receptor-associated kinase 3 | BG929347 | 0.011364 |
| 11753202_s_at | SERPINB4 | serpin peptidase inhibitor, clade B (ovalbumin), member 4 | AB046400.1 | 0.011604 |
| 11739292_at | EHF | ets homologous factor | NM_012153.3 | 0.012013 |
| 11748253_a_at | SLC5A1 | solute carrier family 5 (sodium/glucose cotransporter), member 1 | AK297665.1 | 0.01209 |
| 11723953_a_at | CLINT1 | clathrin interactor 1 | NM_014666.2 | 0.01254 |
| 11736117_a_at | ZFAND5 | zinc finger, AN1-type domain 5 | AF062346.1 | 0.012593 |
| 11724795_at | ZG16B | zymogen granule protein 16 homolog B (rat) | NM_145252.2 | 0.013029 |
| 11717765_a_at | MGLL | monoglyceride lipase | NM_007283.5 | 0.01317 |
| 11744194_a_at | ABCC3 | ATP-binding cassette, sub-family C (CFTR/MRP), member 3 | CB055248 | 0.013406 |
| 11746088_a_at | IFI44 | interferon-induced protein 44 | DB350079 | 0.013466 |
| 11733533_at | CYP4F22 | cytochrome P450, family 4, subfamily F, polypeptide 22 | NM_173483.3 | 0.013708 |
| 11746581_a_at | PCCA | propionyl CoA carboxylase, alpha polypeptide | AK298318.1 | 0.013745 |
| 11717981_a_at | ACP5 | acid phosphatase 5, tartrate resistant | NM_001611.3 | 0.014935 |

TABLE 11

Type I Dermis; Up-regulated

| GeneTitan_ID | Gene | Title | Public ID | p |
|---|---|---|---|---|
| 11733167_at | LRRN4CL | LRRN4 C-terminal like | BC053902.1 | 0.000112 |
| 11720616_a_at | DNM1 | dynamin 1 | NM_001005336.1 | 0.000113 |
| 11758194_s_at | DPP4 | dipeptidyl-peptidase 4 | AI768728 | 0.000125 |
| 11759481_at | COPB1 | Coatomer protein complex, subunit beta 1 | AU143964 | 0.000148 |
| 11718627_at | TRAK1 | trafficking protein, kinesin binding 1 | CA415544 | 0.000173 |
| 11739544_a_at | C19orf12 | chromosome 19 open reading frame 12 | BX328123 | 0.000234 |
| 11743191_a_at | NTM | neurotrimin | AI343272 | 0.000278 |
| 11731649_x_at | NTM | neurotrimin | AY358331.1 | 0.000343 |
| 11723111_at | EMILIN2 | elastin microfibril interfacer 2 | NM_032048.2 | 0.000384 |
| 11719422_s_at | ABCC1 | ATP-binding cassette, sub-family C (CFTR/MRP), member 1 | NM_004996.3 | 0.000385 |

TABLE 11-continued

| | Type I Dermis; Up-regulated | | | |
|---|---|---|---|---|
| GeneTitan_ID | Gene | Title | Public ID | p |
| 11739527_a_at | SECTM1 | secreted and transmembrane 1 | CR614987.1 | 0.000402 |
| 11758810_at | COL14A1 | collagen, type XIV, alpha 1 | NM_021110.1 | 0.000451 |
| 11724441_x_at | PTGIS | prostaglandin I2 (prostacyclin) synthase | NM_000961.3 | 0.000458 |
| 11747944_a_at | PPFIA2 | protein tyrosine phosphatase, receptor type, f polypeptide (PTPRF), interacting protein (liprin), alpha 2 | AK296380.1 | 0.000483 |
| 11728451_a_at | PCOLCE2 | procollagen C-endopeptidase enhancer 2 | NM_013363.2 | 0.000493 |
| 11736086_a_at | HHIP | hedgehog interacting protein | NM_022475.1 | 0.000511 |
| 11758252_s_at | HSD3B7 | hydroxy-delta-5-steroid dehydrogenase, 3 beta- and steroid delta-isomerase 7 | CB115219 | 0.000562 |
| 11756706_a_at | DPP4 | dipeptidyl-peptidase 4 | AK314798.1 | 0.000563 |
| 11720690_a_at | C2orf18 | chromosome 2 open reading frame 18 | NM_017877.3 | 0.000604 |
| 11724619_at | RSPO3 | R-spondin 3 homolog (Xenopus laevis) | NM_032784.3 | 0.000676 |
| 11743447_a_at | BICD2 | bicaudal D homolog 2 (Drosophila) | AW409827 | 0.000721 |
| 11725773_a_at | TBC1D24 | TBC1 domain family, member 24 | NM_020705.1 | 0.000726 |
| 11715704_x_at | ITGA5 | integrin, alpha 5 (fibronectin receptor, alpha polypeptide) | NM_002205.2 | 0.000766 |
| 11756007_a_at | HHIP | hedgehog interacting protein | AK024645.1 | 0.000889 |
| 11741377_a_at | MMP2 | matrix metallopeptidase 2 (gelatinase A, 72 kDa gelatinase, 72 kDa type IV collagenase) | NM_001127891.1 | 0.000928 |
| 11734550_x_at | TGFBI | transforming growth factor, beta-induced, 68 kDa | NM_000358.2 | 0.000963 |
| 11730405_at | MEX3B | mex-3 homolog B (C. elegans) | BC111545.1 | 0.000968 |
| 11731648_a_at | NTM | neurotrimin | AY358331.1 | 0.000985 |
| 11740103_a_at | MAFG | v-maf musculoaponeurotic fibrosarcoma oncogene homolog G (avian) | BX427058 | 0.001077 |
| 11727783_s_at | TPM4 | tropomyosin 4 | NM_003290.2 | 0.001163 |
| 11718269_x_at | ANGPTL2 | angiopoietin-like 2 | AY358274.1 | 0.001231 |
| 11725897_at | TUBB1 | tubulin, beta 1 | BC033679.1 | 0.001234 |
| 11717803_a_at | NTN4 | netrin 4 | NM_021229.3 | 0.001243 |
| 11754476_x_at | DNM1 | dynamin 1 | BQ183716 | 0.00125 |
| 11746893_a_at | MPP1 | membrane protein, palmitoylated 1, 55 kDa | AK304538.1 | 0.001254 |
| 11753088_a_at | MCTP1 | multiple C2 domains, transmembrane 1 | AK297325.1 | 0.001305 |
| 11717568_s_at | NQO1 | NAD(P)H dehydrogenase, quinone 1 | NM_000903.2 | 0.001408 |
| 11720051_at | SPOCK1 | sparc/osteonectin, cwcv and kazal-like domains proteoglycan (testican) 1 | NM_004598.3 | 0.001423 |
| 11757921_s_at | COL14A1 | collagen, type XIV, alpha 1 | AI248460 | 0.001424 |
| 11725923_s_at | ASAP2 | ArfGAP with SH3 domain, ankyrin repeat and PH domain 2 | NM_001135191.1 | 0.001457 |
| 11723225_a_at | CLDN11 | claudin 11 | BC013577.1 | 0.001495 |
| 11754368_a_at | FBN1 | fibrillin 1 | AB208840.1 | 0.001626 |
| 11758062_s_at | STK32B | serine/threonine kinase 32B | AI401203 | 0.001735 |
| 11740358_a_at | LILRB5 | leukocyte immunoglobulin-like receptor, subfamily B (with TM and ITIM domains), member 5 | NM_001081443.1 | 0.001775 |
| 11746200_s_at | EHD2 | EH-domain containing 2 | AK097126.1 | 0.001844 |
| 11747945_x_at | PPFIA2 | protein tyrosine phosphatase, receptor type, f polypeptide (PTPRF), interacting protein (liprin), alpha 2 | AK296380.1 | 0.002036 |
| 11720811_a_at | PAMR1 | peptidase domain containing associated with muscle regeneration 1 | NM_015430.2 | 0.002139 |
| 11731716_at | CCBP2 | chemokine binding protein 2 | NM_001296.4 | 0.002156 |
| 11754706_a_at | HHIP | hedgehog interacting protein | AK098525.1 | 0.002166 |
| 11722940_a_at | SRGAP2 | SLIT-ROBO Rho GTPase activating protein 2 | NM_001042758.1 | 0.00222 |
| 11724848_a_at | DIXDC1 | DIX domain containing 1 | DB358954 | 0.002285 |
| 11718842_a_at | C16orf62 | chromosome 16 open reading frame 62 | BC058845.1 | 0.002303 |

TABLE 11-continued

Type I Dermis; Up-regulated

| GeneTitan_ID | Gene | Title | Public ID | p |
|---|---|---|---|---|
| 11734549_s_at | TGFBI | transforming growth factor, beta-induced, 68 kDa | NM_000358.2 | 0.002382 |
| 11734548_a_at | TGFBI | transforming growth factor, beta-induced, 68 kDa | NM_000358.2 | 0.002425 |
| 11731650_a_at | NTM | neurotrimin | NM_001048209.1 | 0.002477 |
| 11738845_x_at | NTM | neurotrimin | NM_001144059.1 | 0.002642 |
| 11726905_a_at | ARHGAP20 | Rho GTPase activating protein 20 | NM_020809.2 | 0.002644 |
| 11724735_a_at | PDPN | podoplanin | BC014668.1 | 0.002735 |
| 11755796_a_at | ADAM9 | ADAM metallopeptidase domain 9 | BC143924.1 | 0.002822 |
| 11726017_a_at | C17orf63 | chromosome 17 open reading frame 63 | AU253346 | 0.002907 |
| 11741286_a_at | CCRL1 | chemokine (C-C motif) receptor-like 1 | AF110640.1 | 0.002908 |
| 11743910_at | FAM69A | family with sequence similarity 69, member A | BQ015316 | 0.002927 |
| 11756911_a_at | C1QTNF3 | C1q and tumor necrosis factor related protein 3 | BX640995.1 | 0.002969 |
| 11746361_a_at | C7orf58 | chromosome 7 open reading frame 58 | BC030538.2 | 0.002971 |
| 11715703_s_at | ITGA5 | integrin, alpha 5 (fibronectin receptor, alpha polypeptide) | NM_002205.2 | 0.002995 |
| 11735913_s_at | TNXB | tenascin XB | BC125114.1 | 0.003064 |
| 11730236_s_at | MYADM | myeloid-associated differentiation marker | AY358582.1 | 0.003084 |
| 11718267_a_at | ANGPTL2 | angiopoietin-like 2 | NM_012098.2 | 0.003114 |
| 11723217_x_at | SFXN3 | sideroflexin 3 | NM_030971.3 | 0.003152 |
| 11720286_a_at | TRAK1 | trafficking protein, kinesin binding 1 | BC015922.1 | 0.003236 |
| 11717133_a_at | MAFG | v-maf musculoaponeurotic fibrosarcoma oncogene homolog G (avian) | BF340448 | 0.003272 |
| 11717340_at | PTGFRN | prostaglandin F2 receptor negative regulator | NM_020440.2 | 0.003311 |
| 11729541_a_at | CAMKK2 | calcium/calmodulin-dependent protein kinase kinase 2, beta | AB081337.1 | 0.003359 |
| 11718268_a_at | ANGPTL2 | angiopoietin-like 2 | AY358274.1 | 0.003373 |
| 11717413_a_at | WIPI1 | WD repeat domain, phosphoinositide interacting 1 | NM_017983.5 | 0.003406 |
| 11716226_a_at | LIMA1 | LIM domain and actin binding 1 | BC136763.1 | 0.003456 |
| 11740588_at | BDKRB2 | bradykinin receptor B2 | NM_000623.3 | 0.003464 |
| 11741128_a_at | CAPN2 | calpain 2, (m/II) large subunit | NM_001146068.1 | 0.003473 |
| 11717891_a_at | ECM1 | extracellular matrix protein 1 | BC023505.2 | 0.003509 |
| 11730385_at | GREM2 | gremlin 2 | BG150451 | 0.003541 |
| 11756245_s_at | ANXA5 | annexin A5 | CR607543.1 | 0.003586 |
| 11721499_x_at | CTSA | cathepsin A | NM_001127695.1 | 0.003681 |
| 11717757_s_at | RALA | v-ral simian leukemia viral oncogene homolog A (ras related) | AA548928 | 0.003773 |
| 11723075_a_at | BCL9L | B-cell CLL/lymphoma 9-like | AY296059.1 | 0.003835 |
| 11748650_a_at | ADAM33 | ADAM metallopeptidase domain 33 | BC125113.1 | 0.003846 |
| 11758676_s_at | RHOQ | ras homolog gene family, member Q | R23125 | 0.003853 |
| 11724260_a_at | TRIO | triple functional domain (PTPRF interacting) | AF091395.1 | 0.004049 |
| 11724541_s_at | VWF | von Willebrand factor | NM_000552.3 | 0.004078 |
| 11716549_s_at | ISLR | immunoglobulin superfamily containing leucine-rich repeat | NM_005545.3 | 0.0042 |
| 11724228_at | RBMS1 | RNA binding motif, single stranded interacting protein 1 | BC080620.1 | 0.004204 |
| 11752423_a_at | F13A1 | coagulation factor XIII, A1 polypeptide | AK304335.1 | 0.004293 |
| 11757340_s_at | RHOQ | ras homolog gene family, member Q | BM677515 | 0.004317 |
| 11750650_a_at | PAMR1 | peptidase domain containing associated with muscle regeneration 1 | AK297092.1 | 0.004367 |
| 11735263_s_at | SCN2A | sodium channel, voltage-gated, type II, alpha subunit | NM_001040142.1 | 0.004453 |
| 11731682_at | CD70 | CD70 molecule | NM_001252.3 | 0.004492 |
| 11737108_a_at | CCRL1 | chemokine (C-C motif) receptor-like 1 | NM_178445.1 | 0.004501 |

TABLE 11-continued

| Type I Dermis; Up-regulated | | | | |
|---|---|---|---|---|
| GeneTitan_ID | Gene | Title | Public ID | p |
| 11743251_s_at | MMP2 | matrix metallopeptidase 2 (gelatinase A, 72 kDa gelatinase, 72 kDa type IV collagenase) | BX357054 | 0.004507 |
| 11727782_a_at | TPM4 | tropomyosin 4 | NM_003290.2 | 0.004515 |
| 11755955_a_at | FAP | fibroblast activation protein, alpha | AL832166.1 | 0.004528 |
| 11725868_at | SSC5D | scavenger receptor cysteine-rich glycoprotein | NM_001144950.1 | 0.004768 |

TABLE 12

| Type I Dermis; Down-regulated | | | | |
|---|---|---|---|---|
| GeneTitan_ID | Gene | Title | Public ID | p |
| 11718273_a_at | EIF3L | eukaryotic translation initiation factor 3, subunit L | NM_016091.2 | 0.000001 |
| 11729152_a_at | EIF3M | eukaryotic translation initiation factor 3, subunit M | NM_006360.3 | 0.000006 |
| 11755203_x_at | RPL21 | ribosomal protein L21 | BX647669.1 | 0.000006 |
| 11757356_x_at | RPL30 | ribosomal protein L30 | BM855760 | 0.000008 |
| 11717236_x_at | RPS7 | ribosomal protein S7 | NM_001011.3 | 0.000009 |
| 11745362_x_at | RPS11 | ribosomal protein S11 | BC100025.1 | 0.000009 |
| 11757363_x_at | RPS15A | ribosomal protein S15a | DB313157 | 0.000009 |
| 200062_PM_s_at | RPL30 | ribosomal protein L30 | L05095.1 | 0.000009 |
| 11716092_x_at | CKS1B | CDC28 protein kinase regulatory subunit 1B | NM_001826.2 | 0.00001 |
| 11743094_at | SPRR4 | small proline-rich protein 4 | BC069445.1 | 0.000011 |
| 11757421_x_at | RPL31 | ribosomal protein L31 | CD687230 | 0.000011 |
| 11718274_s_at | EIF3L | eukaryotic translation initiation factor 3, subunit L | NM_016091.2 | 0.000012 |
| 11715376_a_at | RPS11 | ribosomal protein S11 | NM_001015.3 | 0.000015 |
| 11757773_x_at | NCRNA00275 | non-protein coding RNA 275 | BF185165 | 0.000015 |
| 11753659_x_at | RPL30 | ribosomal protein L30 | BC095426.1 | 0.000016 |
| 11753694_x_at | RPS15A | ribosomal protein S15a | AB062400.1 | 0.000017 |
| 11755956_x_at | POLE3 | polymerase (DNA directed), epsilon 3 (p17 subunit) | AF070640.1 | 0.000017 |
| 200063_PM_s_at | NPM1 | nucleophosmin (nucleolar phosphoprotein B23, numatrin) | BC002398.1 | 0.000017 |
| 11740643_a_at | CYP4F8 | cytochrome P450, family 4, subfamily F, polypeptide 8 | AF133298.1 | 0.00002 |
| 11757305_x_at | RPSAP58 | ribosomal protein SA pseudogene 58 | BI762726 | 0.000021 |
| 11715958_s_at | RPL7 | ribosomal protein L7 | NM_000971.3 | 0.000023 |
| 11719783_at | RPS23 | ribosomal protein S23 | D14530.1 | 0.000027 |
| 11745154_a_at | NCL | nucleolin | BC006516.2 | 0.000027 |
| 11720183_s_at | EEF1B2 | eukaryotic translation elongation factor 1 beta 2 | NM_001959.3 | 0.000029 |
| 11753691_x_at | RPL24 | ribosomal protein L24 | CR456729.1 | 0.000031 |
| 200013_PM_at | RPL24 | ribosomal protein L24 | NM_000986.1 | 0.000034 |
| 11718275_x_at | EIF3L | eukaryotic translation initiation factor 3, subunit L | NM_016091.2 | 0.000037 |
| 11744326_s_at | RPL37 | ribosomal protein L37 | BC079477.1 | 0.000037 |
| 11757264_s_at | RPS3 | ribosomal protein S3 | BU588459 | 0.000038 |
| 200010_PM_at | RPL11 | ribosomal protein L11 | NM_000975.3 | 0.000039 |
| 11757027_x_at | RPL31 | ribosomal protein L31 | CR600452.1 | 0.000042 |
| 200018_PM_at | RPS13 | ribosomal protein S13 | NM_001017.1 | 0.000046 |
| 11757375_x_at | RPS15 | ribosomal protein S15 | AI625563 | 0.000047 |
| 11754031_s_at | CKS1B | CDC28 protein kinase regulatory subunit 1B | BT007196.1 | 0.000051 |
| 11715733_a_at | NIPSNAP1 | nipsnap homolog 1 (C. elegans) | NM_003634.2 | 0.000054 |
| 11740644_x_at | CYP4F8 | cytochrome P450, family 4, subfamily F, polypeptide 8 | AF133298.1 | 0.000061 |
| 11736188_a_at | ORMDL3 | ORM1-like 3 (S. cerevisiae) | NM_139280.1 | 0.000071 |
| 11730527_a_at | DAPK2 | death-associated protein kinase 2 peroxisomal membrane | AF052941.1 | 0.000088 |

TABLE 12-continued

Type I Dermis; Down-regulated

| GeneTitan_ID | Gene | Title | Public ID | p |
|---|---|---|---|---|
| 11723312_a_at | PXMP2 | protein 2, 22kDa | NM_018663.1 | 0.000092 |
| 11734833_s_at | TAF9B | TAF9B RNA polymerase II, TATA box binding protein (TBP)-associated factor, 31kDa | NM_015975.4 | 0.000093 |
| 11732205_x_at | NAP1L1 | nucleosome assembly protein 1-like 1 | BX413854 | 0.000099 |
| 11752912_x_at | EIF3M | eukaryotic translation initiation factor 3, subunit M | AK292139.1 | 0.000099 |
| 11756437_x_at | RPS18 | ribosomal protein S18 | BQ057441 | 0.0001 |
| 11729011_at | CDH22 | cadherin 22, type 2 | NM_021248.1 | 0.000107 |
| 11734329_at | TNN | tenascin N | NM_022093.1 | 0.000107 |
| 11749558_a_at | CYP4F8 | cytochrome P450, family 4, subfamily F, polypeptide 8 | AK300530.1 | 0.000119 |
| 200029_PM_at | RPL19 | ribosomal protein L19 | NM_000981.1 | 0.000121 |
| 11757386_x_at | NPM1 | nucleophosmin (nucleolar phosphoprotein B23, numatrin) | AL563600 | 0.000122 |
| 11733774_a_at | RPL37 | ribosomal protein L37 | NM_000997.4 | 0.000123 |
| 11729427_a_at | GLI1 | GLI family zinc finger 1 | NM_005269.2 | 0.000126 |
| 11754066_x_at | NPM1 | nucleophosmin (nucleolar phosphoprotein B23, numatrin) | BT007011.1 | 0.000128 |
| 11715626_a_at | RPL11 | ribosomal protein L11 | NM_000975.2 | 0.00013 |
| 11757489_x_at | RPL22 | ribosomal protein L22 | AW268528 | 0.00013 |
| 11757355_x_at | RPL41 | ribosomal protein L41 | BU958994 | 0.000138 |
| 11752726_x_at | GNB2L1 | guanine nucleotide binding protein (G protein), beta polypeptide 2-like 1 | AY159316.1 | 0.000144 |
| 11728288_a_at | KRT15 | keratin 15 | NM_002275.3 | 0.000153 |
| 11756783_x_at | TF | transferrin | BC045772.1 | 0.000155 |
| 11757331_x_at | RPL13A | ribosomal protein L13a | BF688481 | 0.000157 |
| 11744365_a_at | NCRNA00275 | non-protein coding RNA 275 | AY513722.1 | 0.000159 |
| 11739727_x_at | NAP1L1 | nucleosome assembly protein 1-like 1 | BE965760 | 0.00016 |
| 200074_PM_s_at | RPL14 | ribosomal protein L14 | U16738.1 | 0.000161 |
| 200089_PM_s_at | RPL4 | ribosomal protein L4 | AI953886 | 0.000162 |
| 11734331_a_at | TNN | tenascin N | BC136619.1 | 0.000163 |
| 11757906_x_at | RPL10 | ribosomal protein L10 | AL558950 | 0.000167 |
| 11715645_s_at | C22orf28 | chromosome 22 open reading frame 28 | NM_014306.4 | 0.00018 |
| 11756875_x_at | COMMD6 | COMM domain containing 6 | CR603325.1 | 0.000184 |
| 11722318_a_at | EFNB3 | ephrin-B3 | NM_001406.3 | 0.000198 |
| 11756878_a_at | FBL | fibrillarin | CR593763.1 | 0.000198 |
| 11736721_x_at | RPL32 | ribosomal protein L32 | NM_001007073.1 | 0.000199 |
| 11720184_x_at | EEF1B2 | eukaryotic translation elongation factor 1 beta 2 | NM_001959.3 | 0.0002 |
| 11749786_x_at | HNRNPF | heterogeneous nuclear ribonucleoprotein F | AK296696.1 | 0.000201 |
| 11717058_x_at | RPL5 | ribosomal protein L5 | NM_000969.3 | 0.00021 |
| 11752911_a_at | EIF3M | eukaryotic translation initiation factor 3, subunit M | AK292139.1 | 0.000211 |
| 11730790_x_at | NPM1 | nucleophosmin (nucleolar phosphoprotein B23, numatrin) | AK290652.1 | 0.000213 |
| 11753680_x_at | RPL21 | ribosomal protein L21 | CR457032.1 | 0.000213 |
| 200022_PM_at | RPL18 | ribosomal protein L18 | NM_000979.3 | 0.000213 |
| 200014_PM_s_at | HNRNPC | heterogeneous nuclear ribonucleoprotein C (C1/C2) | NM_004500.1 | 0.000215 |
| 11742667_x_at | RPS28 | ribosomal protein S28 | NM_001031.4 | 0.000242 |
| 200082_PM_s_at | RPS7 | ribosomal protein S7 | AI805587 | 0.00025 |
| 11728380_x_at | NACA2 | nascent polypeptide-associated complex alpha subunit 2 | NM_199290.2 | 0.000252 |
| 11756140_s_at | RPL4 | ribosomal protein L4 | BX447218 | 0.000254 |
| 11716304_a_at | ABHD14B | abhydrolase domain containing 14B | NM_032750.2 | 0.000267 |
| 11758357_x_at | RPL9 | ribosomal protein L9 | BF172613 | 0.000272 |
| 11715280_s_at | KRT17 | keratin 17 | g197383031 | 0.000274 |
| 11739813_a_at | FZD1 | frizzled homolog 1 (Drosophila) | BF675672 | 0.000295 |
| 11721885_s_at | CDC42 | cell division cycle 42 (GTP binding protein, 25kDa) | NM_001039802.1 | 0.000307 |

TABLE 12-continued

| | Type I Dermis; Down-regulated | | | |
|---|---|---|---|---|
| GeneTitan_ID | Gene | Title | Public ID | p |
| 11720954_s_at | RPL30 | ribosomal protein L30 | NM_000989.2 | 0.000309 |
| 11743688_at | GLI2 | GLI family zinc finger 2 | AB209354.1 | 0.000312 |
| 11720599_s_at | SUB1 | SUB1 homolog (S. cerevisiae) | NM_006713.3 | 0.000315 |
| 11725875_at | WDR66 | WD repeat domain 66 | NM_144668.4 | 0.000318 |
| 11733496_x_at | COMMD6 | COMM domain containing 6 | AA535445 | 0.000323 |
| 11727795_x_at | EIF3E | eukaryotic translation initiation factor 3, subunit E | NM_001568.2 | 0.000327 |
| 11756215_x_at | UBA52 | ubiquitin A-52 residue ribosomal protein fusion product 1 | BU619323 | 0.000331 |
| 11757059_x_at | RPL36A | ribosomal protein L36a | CR617894.1 | 0.000331 |
| 200012_PM_x_at | RPL21 | ribosomal protein L21 | NM_000982.1 | 0.000335 |
| 11718344_a_at | CNOT7 | CCR4-NOT transcription complex, subunit 7 | NM_013354.5 | 0.00035 |
| 11717235_s_at | RPS7 | ribosomal protein S7 | NM_001011.3 | 0.000352 |
| 11757113_a_at | SNHG1 | small nucleolar RNA host gene 1 (non-protein coding) | 6E836747 | 0.000365 |
| 11743679_a_at | PTCH1 | patched 1 | DB299015 | 0.000374 |
| 11744366_a_at | NCRNA00275 | non-protein coding RNA 275 | CR936805.1 | 0.000378 |

TABLE 13

| | Type II Epidermis; Up-regulated | | | |
|---|---|---|---|---|
| GeneTitan_ID | Gene | Title | Public ID | p |
| 11729461_a_at | CTNS | cystinosis, nephropathic | NM_001031681.2 | 0.000105 |
| 11737824_a_at | STX16 | syntaxin 16 | NM_001134773.1 | 0.000753 |
| 11731828_at | GPC2 | glypican 2 | NM_152742.1 | 0.000819 |
| 11757259_x_at | SCARNA9L | small Cajal body-specific RNA 9-like (retrotransposed) | NR_023358.1 | 0.000852 |
| 11728498_a_at | SVIL | supervillin | NM_003174.3 | 0.001387 |
| 11733298_a_at | VIPR1 | vasoactive intestinal peptide receptor 1 | NM_004624.3 | 0.00166 |
| 11754972_s_at | BAZ2A | bromodomain adjacent to zinc finger domain, 2A | AK127775.1 | 0.001742 |
| 11732899_s_at | SULT1AI | sulfotransferase family, cytosolic, 1A, phenol-preferring, member 1 | NM_177528.1 | 0.001887 |
| 11716708_a_at | DDR1 | discoidin domain receptor tyrosine kinase 1 | NM_013993.2 | 0.001925 |
| 11757623_s_at | RNF5 | ring finger protein 5 | AA923467 | 0.00209 |
| 11715799_s_at | BAT2L1 | HLA-B associated transcript 2-like 1 | NM_013318.3 | 0.002325 |
| 11756190_a_at | CLK3 | CDC-like kinase 3 | CD743118 | 0.002384 |
| 11726634_a_at | MYST3 | MYST histone acetyltransferase (monocytic leukemia) 3 | NM_001099412.1 | 0.002824 |
| 11752331_s_at | SULT1A4 | sulfotransferase family, cytosolic, 1A, phenol-preferring, member 4 | BC111011.1 | 0.002837 |
| 11731093_s_at | BRD1 | bromodomain containing 1 | NM_014577.1 | 0.002905 |
| 11744831_a_at | RPAIN | RPA interacting protein | AY775316.1 | 0.002976 |
| 11744173_x_at | DNAJC4 | DnaJ (Hsp40) homolog, subfamily C, member 4 | BQ267791 | 0.00329 |
| 11723546_s_at | PLD1 | phospholipase D1, phosphatidylcholine-specific | BF434088 | 0.003418 |
| 11732589_a_at | ZNF467 | zinc finger protein 467 | NM_207336.1 | 0.004153 |
| 11721165_a_at | KHNYN | KH and NYN domain containing | NM_015299.2 | 0.00435 |
| 11730324_s_at | SLC38A9 | solute carrier family 38, member 9 | NM_173514.2 | 0.004534 |
| 11739669_at | SS18L1 | synovial sarcoma translocation gene on chromosome 18-like 1 | AB014593.1 | 0.004553 |
| 11758140_s_at | CPSF6 | cleavage and polyadenylation specific factor 6, 68kDa | BU689332 | 0.004569 |

TABLE 13-continued

| | Type II Epidermis; Up-regulated | | | |
|---|---|---|---|---|
| GeneTitan_ID | Gene | Title | Public ID | p |
| 11721912_at | MDM4 | Mdm4 p53 binding protein homolog (mouse) | NM_002393.3 | 0.004611 |
| 11744830_x_at | NPIPL3 | nuclear pore complex interacting protein-like 3 | AK303166.1 | 0.004653 |
| 11729100_a_at | TTC18 | tetratricopeptide repeat domain 18 | NM_145170.3 | 0.004727 |
| 11757896_s_at | C1orf63 | chromosome 1 open reading frame 63 | R81538 | 0.004766 |
| 11715976_a_at | VGLL4 | vestigial like 4 (Drosophila) | NM_001128219.1 | 0.004868 |
| 11729196_a_at | STX16 | syntaxin 16 | 6E782754 | 0.004954 |
| 11758055_x_at | RGPD8 | RANBP2-like and GRIP domain containing 8 | BQ005433 | 0.005005 |
| 11721624_s_at | WSB1 | WD repeat and SOCS box-containing 1 | NM_015626.8 | 0.005017 |
| 11720589_s_at | PHF21A | PHD finger protein 21A | BU733437 | 0.005058 |
| 11720895_at | SOS1 | son of seven less homolog 1 (Drosophila) | BM970418 | 0.005891 |
| 11761133_at | KDM5C | lysine (K)-specific demethylase 5C | EF613277.1 | 0.006011 |
| 11726189_x_at | HCFC1R1 | host cell factor C1 regulator 1 (XPO1 dependent) | NM_017885.2 | 0.006166 |
| 11721598_a_at | EFS | embryonal Fyn-associated substrate | NM_032459.1 | 0.006547 |
| 11745431_a_at | SVIL | supervillin | BC092440.1 | 0.006666 |
| 11740447_x_at | BTN3A1 | butyrophilin, subfamily 3, member A1 | NM_194441.2 | 0.006686 |
| 11726515_a_at | CLK4 | CDC-like kinase 4 | AF294429.1 | 0.006691 |
| 11746529_x_at | TNFRSF14 | tumor necrosis factor receptor superfamily, member 14 (herpesvirus entry mediator) | BC029848.1 | 0.006897 |
| 11759308_s_at | MAGI1 | membrane associated guanylate kinase, WW and PDZ domain containing 1 | AL050184.1 | 0.006929 |
| 11749473_a_at | MEF2D | myocyte enhancer factor 2D | BC040949.1 | 0.007372 |
| 11719128_a_at | LMF2 | lipase maturation factor 2 | NM_033200.1 | 0.007569 |
| 11762365_x_at | KIAA0415 | KIAA0415 | AB007875.1 | 0.007605 |
| 11716129_at | IGF2R | insulin-like growth factor 2 receptor | NM_000876.2 | 0.007692 |
| 11717989_a_at | SUN1 | Sad1 and UNC84 domain containing 1 | NM_001130965.1 | 0.007807 |
| 11755196_a_at | CORO6 | coronin 6 | AK092430.1 | 0.007848 |
| 11755758_s_at | NLRC5 | NLR family, CARD domain containing 5 | AK090439.1 | 0.00788 |
| 11716283_at | PAPD7 | PAP associated domain containing 7 | NM_006999.3 | 0.008191 |
| 11730449_a_at | DHRS12 | dehydrogenase/reductase (SDR family) member 12 | NM_024705.1 | 0.008218 |
| 11718728_a_at | ZNF655 | zinc finger protein 655 | NM_001083956.1 | 0.008286 |
| 11718820_at | TSC1 | tuberous sclerosis 1 | NM_000368.3 | 0.008558 |
| 11729483_a_at | KLF8 | Kruppel-like factor 8 | NM_007250.4 | 0.008607 |
| 11754192_s_at | SRSF11 | serine/arginine-rich splicing factor 11 | CR614713.1 | 0.009136 |
| 11758557_s_at | ZFP36L1 | zinc finger protein 36, C3H type-like 1 | AI758505 | 0.009209 |
| 11723598_x_at | MAP2K7 | mitogen-activated protein kinase kinase 7 | NM_145185.2 | 0.009355 |
| 11754541_a_at | CCDC45 | coiled-coil domain containing 45 | AW167096 | 0.00982 |
| 11757630_s_at | HERPUD2 | HERPUD family member 2 | AA709265 | 0.010052 |
| 11718536_s_at | NKTR | natural killer-tumor recognition sequence | NM_005385.3 | 0.010291 |
| 11755674_s_at | RALGAPA1 | Ral GTPase activating protein, alpha subunit 1 (catalytic) | DQ786317.1 | 0.010335 |
| 11757591_s_at | PAN3 | PAN3 poly(A) specific ribonuclease subunit homolog (S. cerevisiae) | DB314869 | 0.010593 |
| 11724312_a_at | SH3BP2 | SH3-domain binding protein 2 | NM_001145855.1 | 0.010664 |
| 11757197_s_at | NCRNA00201 | non-protein coding RNA 201 | NR_026778.1 | 0.010882 |

TABLE 13-continued

| Type II Epidermis; Up-regulated | | | | |
|---|---|---|---|---|
| GeneTitan_ID | Gene | Title | Public ID | p |
| 11759150_at | CNOT4 | CCR4-NOT transcription complex, subunit 4 | BC035590.1 | 0.011523 |
| 11718939_s_at | TNFAIP3 | tumor necrosis factor, alpha-induced protein 3 | NM_006290.2 | 0.011563 |
| 11738035_s_at | RTN4 | reticulon 4 | AK302741.1 | 0.011615 |
| 11719084_a_at | SMARCC2 | SWI/SNF related, matrix associated, actin dependent regulator of chromatin, subfamily c, member 2 | BF663402 | 0.011872 |
| 11736501_x_at | SS18 | synovial sarcoma translocation, chromosome 18 | NM_005637.2 | 0.011911 |
| 11755811_a_at | ZNF266 | zinc finger protein 266 | AL833503.1 | 0.012172 |
| 11720362_at | PHIP | pleckstrin homology domain interacting protein | CR600369.1 | 0.012352 |
| 11724758_s_at | GPBP1L1 | GC-rich promoter binding protein 1-like 1 | NM_021639.4 | 0.012429 |
| 11754821_s_at | SLC38AI | solute carrier family 38, member 1 | AI476037 | 0.012431 |
| 11758907_at | ZNF827 | zinc finger protein 827 | AA031947 | 0.012473 |
| 11736498_a_at | TNRC6B | trinucleotide repeat containing 6B | NM_015088.2 | 0.012866 |
| 11716010_s_at | DYNC1LI2 | dynein, cytoplasmic 1, light intermediate chain 2 | NM_006141.2 | 0.01317 |
| 11745723_a_at | MALAT1 | metastasis associated lung adenocarcinoma transcript 1 (non-protein coding) | BX538238.1 | 0.013758 |
| 11758584_s_at | STYX | serine/threonine/tyrosine interacting protein | N34305 | 0.013878 |
| 11757558_s_at | LONRF1 | LON peptidase N-terminal domain and ring finger 1 | BF680438 | 0.014197 |
| 11750922_x_at | AMT | aminomethyltransferase | AK296177.1 | 0.0143 |
| 11718558_s_at | MKRN1 | makorin ring finger protein 1 | NM_001145125.1 | 0.014465 |
| 11723112_a_at | CCDC84 | coiled-coil domain containing 84 | NM_198489.1 | 0.014471 |
| 11757808_s_at | RERE | arginine-glutamic acid dipeptide (RE) repeats | BM706668 | 0.014565 |
| 11763191_at | PRICKLE3 | prickle homolog 3 (Drosophila) | AK303308.1 | 0.014697 |
| 11757821_s_at | LDB1 | LIM domain binding 1 | AW271288 | 0.014809 |
| 11755194_s_at | CCN L2 | cyclin L2 | AK000685.1 | 0.014941 |
| 11720122_at | GIGYF1 | GRB10 interacting GYF protein 1 | NM_022574.4 | 0.014956 |
| 11763351_at | LOC286052 | hypothetical protein LOC286052 | CK819455 | 0.014973 |
| 11722752_a_at | C14orf43 | chromosome 14 open reading frame 43 | NM_194278.3 | 0.015053 |
| 11757958_s_at | POGZ | pogo transposable element with ZNF domain | AI374931 | 0.015063 |
| 11734056_at | PTGR2 | prostaglandin reductase 2 | NM_152444.2 | 0.015377 |
| 11722715_at | STK35 | serine/threonine kinase 35 | NM_080836.2 | 0.015673 |
| 11722134_a_at | TNFRSF25 | tumor necrosis factor receptor superfamily, member 25 | NM_148965.1 | 0.015688 |
| 11715192_s_at | C7orf46 | chromosome 7 open reading frame 46 | g188219621 | 0.015694 |
| 11720795_s_at | NUPL1 | nucleoporin like 1 | NM_014089.3 | 0.016154 |
| 11729510_a_at | WDR33 | WD repeat domain 33 | NM_001006623.1 | 0.016469 |
| 11724066_s_at | HCFC1R1 | host cell factor C1 regulator 1 (XPO1 dependent) | NM_001002018.1 | 0.016491 |
| 11718534_at | NKTR | natural killer-tumor recognition sequence | AI361805 | 0.016611 |
| 11741625_a_at | SLC22A23 | solute carrier family 22, member 23 | NM_021945.5 | 0.016631 |
| 11722305_at | ARHGAP23 | Rho GTPase activating protein 23 | NM_020876.1 | 0.01665 |
| 11764248_s_at | LDLRAD3 | low density lipoprotein receptor class A domain containing 3 | AW043782 | 0.016656 |

TABLE 14

| | Type II Epidermis; Down-regulated | | | |
|---|---|---|---|---|
| GeneTitan_ID | Gene | Title | Public ID | p |
| 11719408_a_at | HIPK2 | homeodomain interacting protein kinase 2 | BM679184 | 0.000155 |
| 11739028_s_at | CLTC | clathrin, heavy chain (Hc) | BX395378 | 0.00019 |
| 11747337_x_at | EIF3I | eukaryotic translation initiation factor 3, subunit I | U36764.1 | 0.000378 |
| 11749845_a_at | TBC1D22A | TBC1 domain family, member 22A | AK301445.1 | 0.000577 |
| 11723960_at | SCFD2 | sec1 family domain containing 2 | BC032453.1 | 0.000699 |
| 11717105_a_at | PSMB5 | proteasome (prosome, macropain) subunit, beta type, 5 | NM_001144932.1 | 0.00071 |
| 11716545_x_at | PSMC1 | proteasome (prosome, macropain) 26S subunit, ATPase, 1 | NM_002802.2 | 0.00077 |
| 11730754_s_at | AGPAT5 | 1-acylglycerol-3-phosphate O-acyltransferase 5 (lysophosphatidic acid acyltransferase, epsilon) | CB306609 | 0.00077 |
| 11750994_a_at | SYAP1 | synapse associated protein 1 | AK295322.1 | 0.000788 |
| 11754977_x_at | CTSB | cathepsin B | CR614817.1 | 0.000808 |
| 200096_PM_s_at | ATP6V0E1 | ATPase, H+ transporting, lysosomal 9kDa, V0 subunit e1 | AI862255 | 0.000889 |
| 11738899_a_at | SERPINB12 | serpin peptidase inhibitor, clade B (ovalbumin), member 12 | NM_080474.1 | 0.000913 |
| 11747533_a_at | GRSF1 | G-rich RNA sequence binding factor 1 | AK298883.1 | 0.000973 |
| 11733918_a_at | PSMD14 | proteasome (prosome, macropain) 26S subunit, non-ATPase, 14 | BC066336.1 | 0.001091 |
| 11753572_a_at | TMEM85 | transmembrane protein 85 | AY336092.1 | 0.001121 |
| 11738988_a_at | GANAB | glucosidase, alpha; neutral AB | AK302752.1 | 0.001195 |
| 11751303_s_at | GORASP2 | golgi reassembly stacking protein 2, 55kDa | AK293640.1 | 0.001298 |
| 11719482_a_at | MRPL21 | mitochondrial ribosomal protein L21 | NM_181515.1 | 0.001366 |
| 11715943_x_at | PSMB1 | proteasome (prosome, macropain) subunit, beta type, 1 | NM_002793.3 | 0.001475 |
| 11749935_s_at | TPM3 | tropomyosin 3 | AK298678.1 | 0.001523 |
| 11736759_s_at | SDHC | succinate dehydrogenase complex, subunit C, integral membrane protein, 15kDa | AB211234.1 | 0.001635 |
| 11731397_a_at | YWHAB | tyrosine 3-monooxygenase/tryptophan 5-monooxygenase activation protein, beta polypeptide | AI866370 | 0.001646 |
| 11751557_s_at | MED27 | mediator complex subunit 27 | AK298436.1 | 0.001692 |
| 11747146_s_at | TMBIM6 | transmembrane BAX inhibitor motif containing 6 | AK304577.1 | 0.001727 |
| 11716972_s_at | NSF | N-ethylmaleimide-sensitive factor | NM_006178.2 | 0.001747 |
| 11754009_a_at | PSMB5 | proteasome (prosome, macropain) subunit, beta type, 5 | BT006777.1 | 0.001747 |
| 11717459_a_at | MRPL39 | mitochondrial ribosomal protein L39 | NM_017446.3 | 0.001824 |
| 11742273_a_at | MRPL33 | mitochondrial ribosomal protein L33 | AF420602.1 | 0.001825 |
| 11739599_a_at | ZNF398 | zinc finger protein 398 | BU736496 | 0.001891 |
| 11747534_a_at | RSU1 | Ras suppressor protein 1 | BC008691.1 | 0.002033 |
| 11747507_x_at | NAP1L4 | nucleosome assembly protein 1-like 4 | AK316548.1 | 0.002069 |
| 11747506_a_at | NAP1L4 | nucleosome assembly protein 1-like 4 | AK316548.1 | 0.002092 |
| 11748665_a_at | PICALM | phosphatidylinositol binding clathrin assembly protein | AK300275.1 | 0.002111 |
| 11718035_at | PPIL1 | peptidylprolyl isomerase (cyclophilin)-like 1 | AF151882.1 | 0.002124 |
| 11751336_x_at | MKRN1 | makorin ring finger protein 1 | AK297361.1 | 0.002138 |
| | | activating signal cointegrator 1 complex | | |

TABLE 14-continued

| | Type II Epidermis; Down-regulated | | | |
|---|---|---|---|---|
| GeneTitan_ID | Gene | Title | Public ID | p |
| 11720264_at | ASCC3 | subunit 3 | NM_006828.2 | 0.002301 |
| 11725037_a_at | 5EC23IP | 5EC23 interacting protein | AK000698.1 | 0.002534 |
| 11715772_x_at | MRPL13 | mitochondrial ribosomal protein L13 | NM_014078.4 | 0.002536 |
| 11716173_a_at | P4HB | prolyl 4-hydroxylase, beta polypeptide | AK296206.1 | 0.002544 |
| 11717106_x_at | PSMB5 | proteasome (prosome, macropain) subunit, beta type, 5 | NM_001144932.1 | 0.002579 |
| 200059_PM_s_at | RHOA | ras homolog gene family, member A | BC001360.1 | 0.002604 |
| 11746655_a_at | ACAA1 | acetyl-CoA acyltransferase 1 | AK303251.1 | 0.002689 |
| 11739201_a_at | ATP5G3 | ATP synthase, H+ transporting, mitochondrial Fo complex, subunit C3 (subunit 9) | 6E736890 | 0.002714 |
| 11728637_a_at | ATP5AI | ATP synthase, H+ transporting, mitochondrial F1 complex, alpha subunit 1, cardiac muscle | NM_001001937.1 | 0.002718 |
| 11756013_a_at | BCL2L10 | BCL2-like 10 (apoptosis facilitator) | BC143227.1 | 0.002726 |
| 11754271_a_at | PSMB4 | proteasome (prosome, macropain) subunit, beta type, 4 | BM849884 | 0.002734 |
| 11731415_a_at | PSMD6 | proteasome (prosome, macropain) 26S subunit, non-ATPase, 6 | NM_014814.1 | 0.002807 |
| 11715840_s_at | SDHC | succinate dehydrogenase complex, subunit C, integral membrane protein, 15kDa | BC020808.1 | 0.002866 |
| 11755266_x_at | SUCLA2 | succinate-CoA ligase, ADP-forming, beta subunit | AK001458.1 | 0.003146 |
| 11750876_a_at | SCFD1 | sec1 family domain containing 1 | AK301406.1 | 0.003266 |
| 11752770_a_at | SMARCE1 | SWI/SNF related, matrix associated, actin dependent regulator of chromatin, subfamily e, member 1 | AK294666.1 | 0.003311 |
| 11758800_x_at | SERBP1 | SERPINE1 mRNA binding protein 1 | AF151813.1 | 0.003464 |
| 11751835_a_at | LTV1 | LTV1 homolog (S. cerevisiae) | AY326463.1 | 0.003472 |
| 11758319_x_at | UBC | ubiquitin C | BF672950 | 0.003583 |
| 11729168_x_at | DCTD | dCMP deaminase | BC001286.1 | 0.003633 |
| 11717159_a_at | NDUFB3 | NADH dehydrogenase (ubiquinone) 1 beta subcomplex, 3, 12kDa | NM_002491.2 | 0.003697 |
| 11744181_a_at | FARS2 | phenylalanyl-tRNA synthetase 2, mitochondrial | BG192794 | 0.003735 |
| 11751412_x_at | ARL1 | ADP-ribosylation factor-like 1 | AK301701.1 | 0.003805 |
| 11734682_a_at | PSMA7 | proteasome (prosome, macropain) subunit, alpha type, 7 | NM_002792.2 | 0.003878 |
| 11750059_a_at | MLX | MAX-like protein X | AK296114.1 | 0.003884 |
| 11715718_a_at | ZNHIT1 | zinc finger, HIT-type containing 1 | NM_006349.2 | 0.003894 |
| 11751360_x_at | REX02 | REX2, RNA exonuclease 2 homolog (S. cerevisiae) | BC107887.1 | 0.003907 |
| 11747349_s_at | PSAT1 | phosphoserine aminotransferase 1 | BT006840.1 | 0.003982 |
| 11763975_a_at | MRPS11 | mitochondrial ribosomal protein S11 | DB346141 | 0.004073 |
| 11716381_x_at | BRP44 | brain protein 44 | NM_015415.2 | 0.00408 |
| 11751523_a_at | TMED5 | transmembrane emp24 protein transport domain containing 5 | AK293308.1 | 0.004086 |
| 11753974_s_at | SNRPG | small nuclear ribonucleoprotein polypeptide G | CR456918.1 | 0.004159 |
| 11732216_s_at | PEF1 | penta-EF-hand domain containing 1 | CR542139.1 | 0.004221 |
| 11718978_x_at | CAPN2 | calpain 2, (m/II) large subunit | BC021303.2 | 0.004238 |
| | | ATPase, H+ transporting, lysosomal 38kDa, V0 subunit | | |

TABLE 14-continued

| | Type II Epidermis; Down-regulated | | | |
|---|---|---|---|---|
| GeneTitan_ID | Gene | Title | Public ID | p |
| 11763422_a_at | ATP6V0D1 | d1 | BX397389 | 0.004241 |
| 11754060_a_at | DAD1 | defender against cell death | CR542204.1 | 0.004283 |
| 11743905_a_at | SPCS1 | signal peptidase complex subunit 1 homolog (S. cerevisiae) | 6E782150 | 0.004361 |
| 11715732_at | PSMB3 | proteasome (prosome, macropain) subunit, beta type, 3 | NM_002795.2 | 0.004369 |
| 11751505_a_at | YIPF1 | Yip1 domain family, member 1 | AK300240.1 | 0.004409 |
| 11742925_a_at | C11orf59 | chromosome 11 open reading frame 59 | CR457247.1 | 0.004503 |
| 11715417_s_at | SKP1 | S-phase kinase-associated protein 1 | BC020798.1 | 0.004548 |
| 11750438_x_at | PGAM1 | phosphoglycerate mutase 1 (brain) | AK296619.1 | 0.004563 |
| 11752939_x_at | PGK1 | phosphoglycerate kinase 1 | AK298855.1 | 0.004575 |
| 11723478_s_at | CDC123 | cell division cycle 123 homolog (S. cerevisiae) | NM_006023.2 | 0.004585 |
| 11743034_x_at | RDH11 | retinol dehydrogenase 11 (all-trans/9-cis/11-cis) | AK289427.1 | 0.004593 |
| 11754086_x_at | VAPA | VAMP (vesicle-associated membrane protein)-associated protein A, 33kDa | BT019618.1 | 0.004657 |
| 11749303_s_at | HNRNPD | heterogeneous nuclear ribonucleoprotein D (AU-rich element RNA binding protein 1, 37kDa) | AK300149.1 | 0.004671 |
| 11753142_a_at | PSMD11 | proteasome (prosome, macropain) 26S subunit, non-ATPase, 11 | AK300342.1 | 0.004673 |
| 11747719_a_at | KIAA0391 | KIAA0391 | AK304066.1 | 0.004719 |
| 11748974_s_at | CWF19L1 | CWF19-like 1, cell cycle control (S. pombe) | AK295303.1 | 0.004746 |
| 11751133_a_at | ATP6V1B2 | ATPase, H+ transporting, lysosomal 56/58kDa, V1 subunit B2 | AK298819.1 | 0.004759 |
| 11715552_a_at | IMMT | inner membrane protein, mitochondrial | NM_006839.2 | 0.004766 |
| 11747365_a_at | QARS | glutaminyl-tRNA synthetase | AK302867.1 | 0.004855 |
| 11758248_s_at | SDHD | succinate dehydrogenase complex, subunit D, integral membrane protein | BF696015 | 0.004909 |
| 11753592_x_at | EEF1G | eukaryotic translation elongation factor 1 gamma | AK299876.1 | 0.004961 |
| 11715369_s_at | NDUFA4 | NADH dehydrogenase (ubiquinone) 1 alpha subcomplex, 4, 9kDa | BC105295.1 | 0.005125 |
| 11715499_x_at | CBX3 | chromobox homolog 3 | U26312.1 | 0.005141 |
| 11715874_s_at | ATP5H | ATP synthase, H+ transporting, mitochondrial Fo complex, subunit d | NM_006356.2 | 0.005143 |
| 11758311_s_at | SDHD | succinate dehydrogenase complex, subunit D, integral membrane protein | BF697775 | 0.005199 |
| 11715883_x_at | DAP3 | death associated protein 3 | NM_004632.2 | 0.005251 |
| 11754030_a_at | PABPC4 | poly(A) binding protein, cytoplasmic 4 (inducible form) | BC118568.1 | 0.00537 |
| 11749682_s_at | EXOC5 | exocyst complex component 5 | AK303531.1 | 0.005371 |
| 11718142_a_at | TTC27 | tetratricopeptide repeat domain 27 | NM_017735.3 | 0.005424 |
| 11754067_a_at | TXNDC9 | thioredoxin domain containing 9 | CR456935.1 | 0.005482 |
| 11716509_a_at | AKR1A1 | aldo-keto reductase family 1, member A1 (aldehyde reductase) | NM_006066.2 | 0.005483 |

TABLE 15

Type II Dermis; Up-regulated

| GeneTitan_ID | Gene | Title | Public ID | p |
|---|---|---|---|---|
| 11715351_at | COL1AI | collagen, type I, alpha 1 | NM_000088.3 | 0.000139 |
| 11715352_x_at | COL1AI | collagen, type I, alpha 1 | NM_000088.3 | 0.000375 |
| 11734105_a_at | PNMAL2 | PNMA-like 2 | AB033009.1 | 0.001583 |
| 11763844_s_at | UBXN6 | UBX domain protein 6 | CR590857.1 | 0.001819 |
| 11756896_a_at | COL6A6 | collagen, type VI, alpha 6 | AL713792.1 | 0.002188 |
| 11715284_x_at | C15orf40 | chromosome 15 open reading frame 40 | g237858663 | 0.003648 |
| 11715852_at | PDGFRB | platelet-derived growth factor receptor, beta polypeptide | NM_002609.3 | 0.005919 |
| 11715888_s_at | PIP4K2B | phosphatidylinositol-5-phosphate 4-kinase, type II, beta | NM_003559.4 | 0.006199 |
| 11724481_a_at | C5orf13 | chromosome 5 open reading frame 13 | NM_004772.2 | 0.006404 |
| 11758388_s_at | LHX8 | LIM homeobox 8 | DB302169 | 0.006562 |
| 11727836_a_at | GPR78 | G protein-coupled receptor 78 | NM_001014447.1 | 0.007388 |
| 11729827_at | FAM110B | family with sequence similarity 110, member B | BCO24294.1 | 0.009523 |
| 11744562_x_at | FAM176B | family with sequence similarity 176, member B | BC071697.1 | 0.009813 |
| 11725867_s_at | EBF3 | early B-cell factor 3 | NM_001005463.1 | 0.009883 |
| 11749069_a_at | PAQR4 | progestin and adipoQ receptor family member IV | AK295348.1 | 0.010054 |
| 11723068_at | CRHBP | corticotropin releasing hormone binding protein | NM_001882.3 | 0.011101 |
| 11723174_a_at | FNDC1 | fibronectin type III domain containing 1 | NM_032532.2 | 0.011173 |
| 11717274_s_at | COL5AI | collagen, type V, alpha 1 | BQ007762 | 0.012177 |
| 11729541_a_at | CAMKK2 | calcium/calmodulin-dependent protein kinase kinase 2, beta | AB081337.1 | 0.012395 |
| 11724848_a_at | DIXDC1 | DIX domain containing 1 | DB358954 | 0.013451 |
| 11726830_at | ANTXR1 | anthrax toxin receptor 1 | NM_018153.3 | 0.013945 |
| 11727296_s_at | TGFB3 | transforming growth factor, beta 3 | NM_003239.2 | 0.014199 |
| 11759905_a_at | EXD3 | exonuclease 3'-5' domain containing 3 | BC110879.1 | 0.01495 |
| 11721372_at | TCF7L1 | transcription factor 7-like 1 (T-cell specific, HMG-box) | NM_031283.1 | 0.01515 |
| 11755955_a_at | alpha | fibroblast activation protein, alpha FAP | AL832166.1 | 0.015704 |
| 11725989_x_at | MMP14 | matrix metallopeptidase 14 (membrane-inserted) | NM_004995.2 | 0.019095 |
| 11717272_at | COL5AI | collagen, type V, alpha 1 | AB371583.1 | 0.020092 |
| 11739544_a_at | C19orf12 | chromosome 19 open reading frame 12 | BX328123 | 0.021 |
| 11727867_a_at | CLEC3B | C-type lectin domain family 3, member B | NM_003278.2 | 0.024069 |
| 11731645_a_at | CAMKK2 | calcium/calmodulin-dependent protein kinase kinase 2, beta | BCO26060.2 | 0.024228 |
| 11729101_a_at | AKR1C2 | aldo-keto reductase family 1, member C2 (dihydrodiol dehydrogenase 2; bile acid binding protein; 3-alpha hydroxysteroid dehydrogenase, type III) | NM_205845.1 | 0.024814 |
| 11726474_a_at | HES4 | hairy and enhancer of split 4 (Drosophila) | NM_021170.3 | 0.025047 |
| 11725224_a_at | ZNF193 | zinc finger protein 193 | NM_006299.3 | 0.026826 |
| 11715350_a_at | COL1AI | collagen, type I, alpha 1 | BC036531.2 | 0.026857 |
| 11741377_a_at | MMP2 | matrix metallopeptidase 2 (gelatinase A, 72kDa gelatinase, 72kDa type IV collagenase) | NM_001127891.1 | 0.02687 |
| 11722292_a_at | NYNRIN | NYN domain and retroviral integrase containing | NM_025081.2 | 0.027121 |
| 11730404_at | MEX3B | mex-3 homolog B (C. elegans) | NM_032246.3 | 0.027161 |
| 11759126_a_at | THRA | thyroid hormone receptor, alpha (erythroblastic leukemia viral (v-erb-a) oncogene homolog, avian) | CB054873 | 0.02738 |
| 11744348_x_at | COL6A2 | collagen, type VI, alpha 2 | BC002484.2 | 0.027551 |

TABLE 15-continued

Type II Dermis; Up-regulated

| GeneTitan_ID | Gene | Title | Public ID | p |
|---|---|---|---|---|
| 11720845_a_at | CD248 | CD248 molecule, endosialin | NM_020404.2 | 0.02836 |
| 11720372_at | TESC | tescalcin | NM_017899.2 | 0.028677 |
| 11752890_a_at | SNTA1 | syntrophin, alpha 1 (dystroph in-associated protein A1, 59kDa, acidic component) | AK301800.1 | 0.029777 |
| 11717273_at | COL5A1 | collagen, type V, alpha 1 | BQ007762 | 0.030174 |
| 11754184_a_at | ALDH1A3 | aldehyde dehydrogenase 1 family, member A3 | BX538027.1 | 0.030605 |
| 11727155_a_at | TRIOBP | TRIO and F-actin binding protein | NM_007032.5 | 0.030721 |
| 11727031_a_at | SQSTM1 | sequestosome 1 | NM_003900.4 | 0.031363 |
| 11720846_at | CD248 | CD248 molecule, endosialin | NM_020404.2 | 0.031411 |
| 11761938_a_at | TRIO | triple functional domain (PTPRF interacting) | AB115332.1 | 0.032433 |
| 11718096_a_at | MEF2A | myocyte enhancer factor 2A | BC013437.2 | 0.03254 |
| 11734906_a_at | NOVA1 | neuro-oncological ventral antigen 1 | NM_002515.2 | 0.032886 |
| 11724619_at | RSPO3 | R-spondin 3 homolog (Xenopus laevis) | NM_032784.3 | 0.033442 |
| 11726188_at | SHISA3 | shisa homolog 3 (Xenopus laevis) | NM_001080505.1 | 0.033466 |
| 11729644_a_at | GPX8 | glutathione peroxidase 8 (putative) | AK074216.1 | 0.033979 |
| 11756359_s_at | ADRA2C | adrenergic, alpha-2C-, receptor | CR590957.1 | 0.034296 |
| 11747064_x_at | ANXA11 | annexin A11 | AK301047.1 | 0.034459 |
| 11732785_a_at | C16orf45 | chromosome 16 open reading frame 45 | NM_001142469.1 | 0.035589 |
| 11727030_s_at | MAP1A | microtubule-associated protein 1A | NM_002373.5 | 0.036125 |
| 11748738_a_at | SEMA3E | sema domain, immunoglobulin domain (Ig), short basic domain, secreted, (semaphorin) 3E | AK303925.1 | 0.036605 |
| 11721995_a_at | LRRC32 | leucine rich repeat containing 32 | NM_001128922.1 | 0.038953 |
| 11726189_x_at | HCFC1R1 | host cell factor C1 regulator 1 (XPO1 dependent) | NM_017885.2 | 0.039807 |
| 11754792_a_at | RGMA | RGM domain family, member A | AK125204.1 | 0.040435 |
| 11717123_a_at | PPP1R12B | protein phosphatase 1, regulatory (inhibitor) subunit 12B | NM_032105.1 | 0.043242 |
| 11724260_a_at | TRIO | triple functional domain (PTPRF interacting) | AF091395.1 | 0.044219 |
| 11759962_at | TPRKB | TP53RK binding protein | AY643713.1 | 0.045288 |
| 11733167_at | LRRN4CL | LRRN4 C-terminal like | BC053902.1 | 0.045766 |
| 11721703_s_at | TNRC18 | trinucleotide repeat containing 18 | NM_001080495.2 | 0.045935 |
| 11725568_a_at | ATP8A1 | ATPase, aminophospholipid transporter (APLT), class I, type 8A, member 1 | NM_001105529.1 | 0.046173 |
| 11741562_a_at | MME | membrane metallo-endopeptidase | NM_007287.2 | 0.046616 |
| 11745820_s_at | PLAGL1 | pleiomorphic adenoma gene-like 1 | BQ026948 | 0.046856 |
| 11743696_at | CLEC14A | C-type lectin domain family 14, member A | CA412481 | 0.047788 |
| 11720277_a_at | OLFML2A | olfactomedin-like 2A | NM_182487.2 | 0.049248 |

TABLE 16

Type II Dermis; Down-regulated

| GeneTitan_ID | Gene | Title | Public ID | p |
|---|---|---|---|---|
| 11749128_x_at | MAP7 | microtubule-associated protein 7 | AK299355.1 | 0.000033 |
| 11720184_x_at | EEF1B2 | eukaryotic translation elongation factor 1 beta 2 | NM_001959.3 | 0.000101 |
| | | sulfotransferase family 1E, estrogen-preferring, member | | |

TABLE 16-continued

| | Type II Dermis; Down-regulated | | | |
|---|---|---|---|---|
| GeneTitan_ID | Gene | Title | Public ID | p |
| 11724155_at | SULT1E1 | 1 | U08098.1 | 0.000109 |
| 200062_PM_s_at | RPL30 | ribosomal protein L30 | L05095.1 | 0.000123 |
| 11742734_s_at | WDR3 | WD repeat domain 3 | AK292438.1 | 0.000139 |
| 11732205_x_at | NAP1L1 | nucleosome assembly protein 1-like 1 | BX413854 | 0.000141 |
| 11743604_s_at | RRM1 | ribonucleotide reductase M1 | 6E618815 | 0.000164 |
| 11723197_at | HNRNPA3 | heterogeneous nuclear ribonucleoprotein A3 | BX434302 | 0.000178 |
| 11732684_a_at | ABCA12 | ATP-binding cassette, sub-family A (ABC1), member 12 | AF418105.1 | 0.000237 |
| 11739308_s_at | DLG1 | discs, large homolog 1 (Drosophila) | BM681931 | 0.000254 |
| 11725875_at | WDR66 | WD repeat domain 66 | NM_144668.4 | 0.000271 |
| 200082_PM_s_at | RPS7 | ribosomal protein S7 | AI805587 | 0.00036 |
| 200081_PM_s_at | RPS6 | ribosomal protein S6 | 6E741754 | 0.000371 |
| 200063_PM_s_at | NPM1 | nucleophosmin (nucleolar phosphoprotein 623, numatrin) | BC002398.1 | 0.000404 |
| 11757356_x_at | RPL30 | ribosomal protein L30 | BM855760 | 0.000405 |
| 11719783_at | RPS23 | ribosomal protein S23 | D14530.1 | 0.000416 |
| 11724156_at | SULT1E1 | sulfotransferase family 1E, estrogen-preferring, member 1 | NM_005420.2 | 0.000461 |
| 11720183_s_at | EEF1G2 | eukaryotic translation elongation factor 1 beta 2 | NM_001959.3 | 0.000477 |
| 11745154_a_at | NCL | nucleolin | BC006516.2 | 0.000485 |
| 11715958_s_at | RPL7 | ribosomal protein L7 | NM_000971.3 | 0.000491 |
| 11749558_a_at | CYP4F8 | cytochrome P450, family 4, subfamily F, polypeptide 8 | AK300530.1 | 0.000497 |
| 11755203_x_at | RPL21 | ribosomal protein L21 | BX647669.1 | 0.000511 |
| 11728022_a_at | TMEM45A | transmembrane protein 45A | NM_018004.1 | 0.000533 |
| 11718273_a_at | EIF3L | eukaryotic translation initiation factor 3, subunit L | NM_016091.2 | 0.000658 |
| 11757399_s_at | PRKDC | protein kinase, DNA-activated, catalytic polypeptide | AV760328 | 0.000698 |
| 11736055_at | C10orf32 | chromosome 10 open reading frame 32 | BG696280 | 0.000732 |
| 11749267_a_at | SRD5A1 | steroid-5-alpha-reductase, alpha polypeptide 1 (3-oxo-5 alpha-steroid delta 4-dehydrogenase alpha 1) | AK315996.1 | 0.000744 |
| 11716946_s_at | TM9SF3 | transmembrane 9 superfamily member 3 | AF269150.1 | 0.000758 |
| 11726461_a_at | PDCD2 | programmed cell death 2 | NM_144781.1 | 0.000759 |
| 11763318_s_at | CSNK1A1 | casein kinase 1, alpha 1 | BC040473.1 | 0.000792 |
| 11727794_s_at | EIF3E | eukaryotic translation initiation factor 3, subunit E | NM_001568.2 | 0.000802 |
| 11731690_a_at | PIK3C2G | phosphoinositide-3-kinase, class 2, gamma polypeptide | NM_004570.4 | 0.000846 |
| 11748052_x_at | EI24 | etoposide induced 2.4 mRNA | AK316539.1 | 0.000851 |
| 11743094_at | SPRR4 | small proline-rich protein 4 | BC069445.1 | 0.000998 |
| 11717236_x_at | RPS7 | ribosomal protein S7 | NM_001011.3 | 0.001062 |
| 11718719_at | KIAA1797 | KIAA1797 | NM_017794.3 | 0.001102 |
| 11752908_a_at | TCEA1 | transcription elongation factor A (SII), 1 | AK297729.1 | 0.001141 |
| 11753659_x_at | RPL30 | ribosomal protein L30 | BC095426.1 | 0.001161 |
| 11717058_x_at | RPL5 | ribosomal protein L5 | NM_000969.3 | 0.001214 |
| 11736057_s_at | C10orf32 | chromosome 10 open reading frame 32 | BU685637 | 0.00123 |
| 11742991_a_at | PSAT1 | phosphoserine aminotransferase 1 | AK295222.1 | 0.001244 |
| 11758357_x_at | RPL9 | ribosomal protein L9 | BF172613 | 0.00126 |
| 200010_PM_at | RPL11 | ribosomal protein L11 | NM_000975.1 | 0.001282 |
| 11749776_a_at | TFAP2C | transcription factor AP-2 gamma (activating enhancer binding protein 2 gamma) | AK301572.1 | 0.001283 |
| 11727995_a_at | SPINK5 | serine peptidase inhibitor, Kazal type 5 | DQ149928.1 | 0.001284 |
| 11722185_at | C14orf147 | chromosome 14 open reading frame 147 | NM_138288.3 | 0.001309 |
| 11750883_a_at | EIF2A | eukaryotic translation initiation factor 2A, 65kDa | AF109358.1 | 0.001327 |
| 200017_PM_at | RPS27A | ribosomal protein S27a | NM_002954.1 | 0.001414 |
| | | cytochrome P450, family 4, | | |

TABLE 16-continued

| | Type II Dermis; Down-regulated | | | |
|---|---|---|---|---|
| GeneTitan_ID | Gene | Title | Public ID | p |
| 11749559_x_at | CYP4F8 | cytochrome P450, family 4, subfamily F, polypeptide 8 | AK300530.1 | 0.001416 |
| 11722308_a_at | TP63 | tumor protein p63 | NM_003722.4 | 0.001433 |
| 11754066_x_at | NPM1 | nucleophosmin (nucleolar phosphoprotein B23, numatrin) | BT007011.1 | 0.001448 |
| 11743603_a_at | RRM1 | ribonucleotide reductase M1 | 6E618815 | 0.001462 |
| 11754963_a_at | SPINK5 | serine peptidase inhibitor, Kazal type 5 | AK301660.1 | 0.001558 |
| 11747333_a_at | HSD1764 | hydroxysteroid (17-beta) dehydrogenase 4 | AK295440.1 | 0.001571 |
| 11757386_x_at | NPM1 | nucleophosmin (nucleolar phosphoprotein B23, numatrin) | AL563600 | 0.00169 |
| 11751437_a_at | CYP4F8 | cytochrome P450, family 4, subfamily F, polypeptide 8 | AK300539.1 | 0.001708 |
| 11726258_at | RNF141 | ring finger protein 141 | BX503543 | 0.001716 |
| 11720766_a_at | METTL9 | methyltransferase like 9 | AK074529.1 | 0.001743 |
| 11743729_at | CCDC47 | coiled-coil domain containing 47 | AL575693 | 0.001771 |
| 11749786_x_at | HNRNPF | heterogeneous nuclear ribonucleoprotein F | AK296696.1 | 0.001879 |
| 11729152_a_at | EIF3M | eukaryotic translation initiation factor 3, subunit M | NM_006360.3 | 0.001895 |
| 11737634_a_at | UGT2A1 | UDP glucuronosyltransferase 2 family, polypeptide A1 | NM_006798.2 | 0.001986 |
| 11748044_a_at | SCEL | sciellin | BCO20726.1 | 0.002038 |
| 11752912_x_at | EIF3M | eukaryotic translation initiation factor 3, subunit M | AK292139.1 | 0.002066 |
| 11736309_a_at | CSNK1A1 | casein kinase 1, alpha 1 | L37042.1 | 0.002093 |
| 11727421_a_at | CANX | calnexin | C6243867 | 0.002106 |
| 11727425_s_at | CANX | cal nexin | M94859.1 | 0.002182 |
| 11757305_x_at | RPSAP58 | ribosomal protein SA pseudogene 58 | 61762726 | 0.002211 |
| 200087_PM_s_at | TMED2 | transmembrane emp24 domain trafficking protein 2 | AK024976.1 | 0.002219 |
| 11718030_at | RAB11A | RAB11A, member RAS oncogene family | NM_004663.3 | 0.002258 |
| 11742887_a_at | BAG5 | BCL2-associated athanogene 5 | 6Q008934 | 0.00227 |
| 11746199_a_at | METTL9 | methyltransferase like 9 | AA524199 | 0.002298 |
| 11756182_s_at | PSAT1 | phosphoserine aminotransferase 1 | AAI73918 | 0.002312 |
| 11727658_s_at | KLK10 | kallikrein-related peptidase 10 | AF024605.1 | 0.002335 |
| 11732204_a_at | NAP1L1 | nucleosome assembly protein 1-like 1 | BX413854 | 0.002341 |
| 11744334_x_at | RPS17 | ribosomal protein S17 | BC071928.1 | 0.002403 |
| 11748536_a_at | DIMT1L | DIM1 dimethyladenosine transferase 1-like (S. cerevisiae) | BC002841.2 | 0.002406 |
| 11745155_s_at | NCL | nucleolin | BC006516.2 | 0.002458 |
| 11730790_x_at | NPM1 | nucleophosmin (nucleolar phosphoprotein B23, numatrin) | AK290652.1 | 0.002509 |
| 11740643_a_at | CYP4F8 | cytochrome P450, family 4, subfamily F, polypeptide 8 | AF133298.1 | 0.002616 |
| 11755057_s_at | ATP2C1 | ATPase, Ca++ transporting, type 2C, member 1 | AB037768.1 | 0.002687 |
| 11742992_s_at | PSAT1 | phosphoserine aminotransferase 1 | AK295222.1 | 0.002716 |
| 11757424_x_at | RPL37 | ribosomal protein L37 | F34903 | 0.002789 |
| 11723312_a_at | PXMP2 | peroxisomal membrane protein 2, 22kDa | NM_018663.1 | 0.002819 |
| 11756137_x_at | BTF3 | basic transcription factor 3 | CA772090 | 0.002824 |
| 11754054_x_at | RPL3 | ribosomal protein L3 | L22453.1 | 0.002905 |
| 11750667_a_at | RRM1 | ribonucleotide reductase M1 | AK297988.1 | 0.00292 |
| 11751326_a_at | RAB11A | RAB11A, member RAS oncogene family | AK300008.1 | 0.002998 |
| 11749040_a_at | PGM2 | phosphoglucomutase 2 | AK297752.1 | 0.003008 |
| 11715376_a_at | RPS11 | ribosomal protein S11 | NM_001015.3 | 0.003035 |
| 11715849_a_at | DDX47 | DEAD (Asp-Glu-Ala-Asp) box polypeptide 47 | NM_016355.3 | 0.003047 |
| 11726829_at | TYW1B | tRNA-yW synthesizing protein 1 homolog B (S. cerevisiae) | NM_001145440.1 | 0.003195 |
| | | chromosome 14 open reading | | |

TABLE 16-continued

| | Type II Dermis; Down-regulated | | | |
|---|---|---|---|---|
| GeneTitan_ID | Gene | Title | Public ID | p |
| 11756267_x_at | C14orf166 | frame 166 | BX349547 | 0.003217 |
| 11756437_x_at | RPS18 | ribosomal protein S18 | BQ057441 | 0.003368 |
| 11715648_x_at | ADIPOR1 | adiponectin receptor 1 | AY424279.1 | 0.003389 |
| 11747662_x_at | PTGES3 | prostaglandin E synthase 3 (cytosolic) | AK298147.1 | 0.003391 |
| 11749546_a_at | 5LC39A6 | solute carrier family 39 (zinc transporter), member 6 | AK301539.1 | 0.003463 |
| 11745720_s_at | PDIA6 | protein disulfide isomerase family A, member 6 | D49489.1 | 0.00351 |
| 200074_PM_s_at | RPL14 | ribosomal protein L14 | U16738.1 | 0.003587 |
| 11746023_a_at | PGD | phosphogluconate dehydrogenase | AK304423.1 | 0.003624 |

TABLE 17

| | Type III Epidermis; Up-regulated | | | |
|---|---|---|---|---|
| GeneTitan_ID | Gene | Title | Public ID | p |
| 11725675_a_at | RORA | RAR-related orphan receptor A | AA034012 | 0.00064 |
| 11732366_a_at | SCAPER | S-phase cyclin A-associated protein in the ER | BC015212.1 | 0.001096 |
| 11739639_at | CDK12 | cyclin-dependent kinase 12 | AW968504 | 0.001477 |
| 11745215_a_at | KBTBD4 | kelch repeat and BTB (POZ) domain containing 4 | CR457270.1 | 0.001496 |
| 11730873_a_at | RASSF5 | Ras association (RalGDS/AF-6) domain family member 5 | NM_182665.2 | 0.001694 |
| 11718966_at | NUFIP2 | nuclear fragile X mental retardation protein interacting protein 2 | BU533767 | 0.001959 |
| 11718513_x_at | TSPAN14 | tetraspanin 14 | NM_030927.2 | 0.002425 |
| 11744585_a_at | ATRN | attractin | AK302730.1 | 0.003547 |
| 11755420_a_at | KDM4B | lysine (K)-specific demethylase 4B | AK126854.1 | 0.003701 |
| 11720895_at | SOS1 | son of sevenless homolog 1 (Drosophila) | BM970418 | 0.003776 |
| 11734873_a_at | SCAPER | S-phase cyclin A-associated protein in the ER | NM_020843.2 | 0.00429 |
| 11759897_x_at | OFD1 | oral-facial-digital syndrome 1 | BC042830.1 | 0.004666 |
| 11754251_a_at | USP36 | ubiquitin specific peptidase 36 | AK022913.1 | 0.005023 |
| 11736059_a_at | KIF5B | kinesin family member 5B | BC065267.1 | 0.005318 |
| 11754824_a_at | HSPC159 | galectin-related protein | DB323149 | 0.005358 |
| 11757991_s_at | ANKRD12 | ankyrin repeat domain 12 | AA399583 | 0.006238 |
| 11744468_at | SYNCRIP | synaptotagmin binding, cytoplasmic RNA interacting protein | AK056188.1 | 0.007087 |
| 11754992_a_at | CHD1 | chromodomain helicase DNA binding protein 1 | BE535223 | 0.007613 |
| 11716283_at | PAPD7 | PAP associated domain containing 7 | NM_006999.3 | 0.00802 |
| 11722973_s_at | FOXK1 | forkhead box K1 | NM_001037165.1 | 0.008695 |
| 11748149_a_at | FNBP1 | formin binding protein 1 | AK293743.1 | 0.009063 |
| 11722125_a_at | C3orf19 | chromosome 3 open reading frame 19 | AL526467 | 0.009976 |
| 11720007_a_at | STEAP4 | STEAP family member 4 | NM_024636.2 | 0.011197 |
| 11731506_a_at | RAD23B | RAD23 homolog B (S. cerevisiae) | NM_002874.3 | 0.011526 |
| 11724759_s_at | CALM1 | calmodulin 1 (phosphorylase kinase, delta) | NM_006888.3 | 0.011622 |
| 11718161_at | KLF13 | Kruppel-like factor 13 | AF132599.1 | 0.012064 |
| 11726305_at | C10orf84 | chromosome 10 open reading frame 84 | BC023577.2 | 0.012188 |
| 11723962_at | KIAAI143 | KIAAI143 | BC008468.1 | 0.012597 |
| 11740956_x_at | PLEKHN1 | pleckstrin homology domain containing, family N member 1 | NM_032129.1 | 0.013256 |
| 11722305_at | ARHGAP23 | Rho GTPase activating protein 23 | NM_020876.1 | 0.01353 |
| 11726022_a_at | FAM177AI | family with sequence similarity 177, member AI | BC029559.1 | 0.01364 |
| 11754010_x_at | GOLGA2 | golgin A2 | BT007248.1 | 0.013918 |
| 11729523_a_at | NLRC5 | NLR family, CARD domain containing 5 | NM_032206.3 | 0.014235 |

TABLE 17-continued

Type III Epidermis; Up-regulated

| GeneTitan_ID | Gene | Title | Public ID | p |
|---|---|---|---|---|
| 11723113_a_at | CENPC1 | centromere protein C 1 | BC041117.1 | 0.0145 |
| 11754616_a_at | UPF1 | UPF1 regulator of nonsense transcripts homolog (yeast) | AI690963 | 0.014647 |
| 11722291_s_at | ZBTB43 | zinc finger and BTB domain containing 43 | AI745225 | 0.014686 |
| 11739805_a_at | RASAL2 | RAS protein activator like 2 | AK075169.1 | 0.014761 |
| 11723502_at | PRLR | prolactin receptor | AI435838 | 0.014945 |
| 11726244_a_at | RORA | RAR-related orphan receptor A | U04898.1 | 0.01551 |
| 11736104_a_at | ZNF750 | zinc finger protein 750 | BC109037.1 | 0.015749 |
| 11723184_x_at | CNOT6L | CCR4-NOTt ranscription complex, subunit 6-like | BQ025327 | 0.015988 |
| 11755058_a_at | BAZ1A | bromodomain adjacent to zinc finger domain, 1A | BC020636.1 | 0.016704 |
| 11759600_at | SFRS18 | Splicing factor, arginine/serine-rich 18 | AK027751.1 | 0.016758 |
| 11744829_s_at | HLA-E | major histocompatibility complex, class I, E | AK296822.1 | 0.016828 |
| 11719447_s_at | GBP2 | guanylate binding protein 2, interferon-inducible | BC073163.1 | 0.016832 |
| 11720541_at | HSPC159 | galectin-related protein | NM_014181.2 | 0.017088 |
| 11719028_a_at | PSD3 | pleckstrin and Sec7 domain containing 3 | DB314358 | 0.017377 |
| 11754462_a_at | RSPRY1 | ring finger and SPRY domain containing 1 | AU253443 | 0.017904 |
| 11725676_a_at | RORA | RAR-related orphan receptor A | NM_002943.3 | 0.018226 |
| 11722290_a_at | ZBTB43 | zinc finger and BTB domain containing 43 | AI745225 | 0.018329 |
| 11723821_a_at | SMURF2 | SMAD specific E3 ubiquitin protein ligase 2 | AY014180.1 | 0.018461 |
| 11720111_at | SNTB2 | syntrophin, beta 2 (dystrophin-associated protein AI, 59kDa, basic component 2) | BC036429.1 | 0.018669 |
| 11736432_x_at | PPP4R2 | protein phosphatase 4, regulatory subunit 2 | BC128136.1 | 0.01869 |
| 11744000_a_at | NFKBIA | nuclear factor of kappa light polypeptide gene enhancer in B-cells inhibitor, alpha | BX367826 | 0.018695 |
| 11759512_x_at | CWC25 | CWC25 spliceosome-associated protein homolog (S. cerevisiae) | CR748127 | 0.018768 |
| 11716095_s_at | KLF6 | Kruppel-like factor 6 | CD366698 | 0.019227 |
| 11754447_a_at | RPS6KA5 | ribosomal protein S6 kinase, 90kDa, polypeptide 5 | BM968829 | 0.019584 |
| 11719085_a_at | SMARCC2 | SWI/SNF related, matrix associated, actin dependent regulator of chromatin, subfamily c, member 2 | AL544435 | 0.01997 |
| 11727506_x_at | RAB21 | RAB21, member RAS oncogene family | BC021901.1 | 0.020551 |
| 11720276_s_at | TREX1 | three prime repair exonuclease 1 | NM_016381.3 | 0.020671 |
| 11724549_a_at | RSBN1 | round spermatid basic protein 1 | AK292552.1 | 0.020675 |
| 11731645_a_at | CAMKK2 | calcium/calmodulin-dependent protein kinase kinase 2, beta | BC026060.2 | 0.020762 |
| 11737413_at | MICALCL | MICAL C-terminal like | NM_032867.2_ | 0.020903 |
| 11715938_x_at | KHDRBS1 | KH domain containing, RNA binding, signal transduction associated 1 | BC000717.1 | 0.021833 |
| 11747192_x_at | NFIC | nuclear factor I/C (CCAAT-binding transcription factor) | AK289885.1 | 0.022039 |
| 11729396_a_at | NEK1 | NIMA (never in mitosis gene a)-related kinase 1 | Z25431.1 | 0.022138 |
| 11727064_a_at | ANKRD11 | ankyrin repeat domain 11 | BU674634 | 0.022386 |
| 11752626_a_at | PBX1 | pre-B-cell leukemia homeobox 1 | AK299673.1 | 0.022397 |
| 11721119_a_at | ANKHD1-EIF4EBP3 | ANKHD1-EIF4EBP3 readthrough | AF217646.1 | 0.022562 |
| 11743648_a_at | DCAF6 | DDB1 and CUL4 associated factor 6 | BF672818 | 0.022893 |
| 11740362_a_at | FOXN3 | forkhead box N3 | U68723.1 | 0.023025 |
| 11718869_x_at | PALMD | palmdelphin | CF552454 | 0.023068 |
| 11727604_a_at | EPB41L4A | erythrocyte membrane protein band 4.1 like 4A | NM_022140.3 | 0.023101 |
| 11726633_s_at | TRIM8 | tripartite motif-containing 8 | BCO21925.1 | 0.023187 |
| 11732370_a_at | CUX1 | cut-like homeobox 1 | NM_181552.2 | 0.023258 |
| 11726113_a_at | FAM46B | family with sequence similarity 46, member B | NM_052943.3 | 0.023515 |
| 11729100_a_at | TTC18 | tetratricopeptide repeat domain 18 | NM_145170.3 | 0.023862 |

TABLE 17-continued

Type III Epidermis; Up-regulated

| GeneTitan_ID | Gene | Title | Public ID | p |
|---|---|---|---|---|
| 11729259_a_at | ZNF644 | zinc finger protein 644 | BQ014639 | 0.023971 |
| 11745806_a_at | AMMECR1L | AMME chromosomal region gene 1-like | AK095871.1 | 0.024186 |
| 11717894_s_at | PTP4AI | protein tyrosine phosphatase type IVA, member 1 | BC023975.2 | 0.024306 |
| 11728765_a_at | PVRL4 | poliovirus receptor-related 4 | BC010423.1 | 0.024371 |
| 11740747_a_at | DNMT3A | DNA (cytosine-5-)-methyltransferase 3 alpha | AF480163.1 | 0.024617 |
| 11718868_a_at | PALMD | palmdelphin | CF552454 | 0.025394 |
| 11758133_s_at | COL4A3BP | collagen, type IV, alpha 3 (Goodpasture antigen) binding protein | BE046819 | 0.026883 |
| 11749969_a_at | TSPAN5 | tetraspanin 5 | AK295385.1 | 0.027108 |
| 11733899_a_at | TROVE2 | TROVE domain family, member 2 | BX445026 | 0.027171 |
| 11747743_x_at | MTF2 | metal response element binding transcription factor 2 | AK302776.1 | 0.027946 |
| 11746790_a_at | BECN1 | beclin 1, autophagy related | AK298619.1 | 0.027999 |
| 11731573_a_at | FRMD4B | FERM domain containing 4B | AU147415 | 0.028099 |
| 11724271_a_at | HLF | hepatic leukemia factor | EL952952 | 0.028251 |
| 11728683_x_at | KRR1 | KRR1, small subunit (SSU) processome component, homolog (yeast) | U55766.1 | 0.02827 |
| 11758327_s_at | BAZ1A | bromodomain adjacent to zinc finger domain, 1A | BF852255 | 0.02853 |
| 11743300_a_at | SRP72 | signal recognition particle 72kDa | AK225430.1 | 0.028582 |
| 11719103_at | CPNE3 | copine III | CB250550 | 0.028667 |
| 11755895_a_at | FAM129A | family with sequence similarity 129, member A | AK095547.1 | 0.029014 |
| 11721326_at | C3orf14 | chromosome 3 open reading frame 14 | AF236158.1 | 0.029423 |
| 11738035_s_at | RTN4 | reticulon 4 | AK302741.1 | 0.029458 |
| 11746122_s_at | ZC3H11A | zinc finger CCCH-type containing 11A | DA094705 | 0.029486 |
| 11724085_at | DAPL1 | death associated protein-like 1 | NM_001017920.2 | 0.030615 |
| 11735181_a_at | DLX2 | distal-less homeobox 2 | NM_004405.3 | 0.030619 |

TABLE 18

Type III Epidermis; Down-regulated

| GeneTitan_ID | Gene | Title | Public ID | p |
|---|---|---|---|---|
| 11743060_s_at | COMMD10 | COMM domain containing 10 | AL572695 | 0.000211 |
| 11720515_s_at | C9orf150 | chromosome 9 open reading frame 150 | NM_203403.1 | 0.000414 |
| 11716897_x_at | PPIE | peptidylprolyl isomerase E (cyclophilin E) | NM_006112.2 | 0.000535 |
| 11725787_a_at | C4orf43 | chromosome 4 open reading frame 43 | NM_018352.2 | 0.000571 |
| 11729680_a_at | KHK | ketohexokinase (fructokinase) | CR456801.1 | 0.000981 |
| 11745494_x_at | ERCC8 | excision repair cross-complementing rodent repair deficiency, complementation group 8 | U28413.1 | 0.001042 |
| 11745948_a_at | CHEK1 | CHK1 checkpoint homolog (*S. pombe*) | AK299783.1 | 0.0011 |
| 11758965_at | ATG4C | ATG4 autophagy related 4 homolog C (*S. cerevisiae*) | AK027773.1 | 0.001439 |
| 11724079_s_at | E2F2 | E2F transcription factor 2 | NM_004091.2 | 0.001667 |
| 11718280_s_at | TRIAP1 | TP53 regulated inhibitor of apoptosis 1 | NM_016399.2 | 0.001683 |
| 11720459_s_at | CAPRIN1 | cell cycle associated protein 1 | BQ002768 | 0.001735 |
| 11720615_a_at | TUBG2 | tubulin, gamma 2 | NM_016437.2 | 0.00174 |
| 11757673_x_at | RPL39 | ribosomal protein L39 | BX435916 | 0.001879 |
| 11720398_a_at | NBN | nibrin | BC146797.1 | 0.002186 |
| 11734661_a_at | CLSTN3 | calsyntenin 3 | NM_014718.3 | 0.0022 |
| 11726529_s_at | BRCC3 | BRCA1/BRCA2-containing complex, subunit 3 | NM_024332.2 | 0.002236 |
| 11758291_s_at | MRPS10 | mitochondrial ribosomal protein S10 | BF701142 | 0.002439 |
| 11726660_a_at | GPN3 | GPN-loop GTPase 3 | AY359078.1 | 0.002577 |
| 11734619_x_at | ALOX15B | arachidonate 15-lipoxygenase, type B | NM_001141.2 | 0.002749 |

TABLE 18-continued

| | Type III Epidermis; Down-regulated | | | |
|---|---|---|---|---|
| GeneTitan_ID | Gene | Title | Public ID | p |
| 11719482_a_at | MRPL21 | mitochondrial ribosomal protein L21 | NM_181515.1 | 0.002874 |
| 11716896_a_at | PPIE | peptidylprolyl isomerase E (cyclophilin E) | NM_006112.2 | 0.002936 |
| 11757498_s_at | TMEM106C | transmembrane protein 106C | AI278554 | 0.003263 |
| 11722842_s_at | ENAH | enabled homolog (Drosophila) | BC095481.1 | 0.003561 |
| 11722415_a_at | HBS1L | HBS1-like (S. cerevisiae) | BC040849.1 | 0.003563 |
| 11742050_a_at | API5 | apoptosis inhibitor 5 | AK294724.1 | 0.003612 |
| 11719499_at | MAOB | monoamine oxidase B | NM_000898.4 | 0.003642 |
| 11717099_at | HIST1H2BK | histone cluster 1, H2bk | NM_080593.1 | 0.003648 |
| 11744666_at | FAN1 | FANCD2/FANCI-associated nuclease 1 | BC047882.1 | 0.003687 |
| 11756910_x_at | FANCD2 | Fanconi anemia, complementation group D2 | AL832427.1 | 0.00395 |
| 11758535_s_at | GPAM | glycerol-3-phosphate acyltransferase, mitochondrial | AI074401 | 0.003969 |
| 11719920_at | FXC1 | fracture callus 1 homolog (rat) | BC011014.1 | 0.004197 |
| 11719571_a_at | RCHY1 | ring finger and CHY zinc finger domain containing 1 | BC047393.1 | 0.004345 |
| 11763339_a_at | SIVA1 | SIVA1, apoptosis-inducing factor | AK128704.1 | 0.004492 |
| 11740706_a_at | NFRKB | nuclear factor related to kappaB binding protein | NM_006165.3 | 0.004845 |
| 11730410_a_at | PXMP4 | peroxisomal membrane protein 4, 24 kDa | NM_007238.4 | 0.005105 |
| 11739973_s_at | NUAK1 | NUAK family, SNF1-like kinase, 1 | BU686994 | 0.005564 |
| 11757687_x_at | DAD1 | defender against cell death 1 | BU535881 | 0.005572 |
| 11721430_a_at | SYBU | syntabulin (syntaxin-interacting) | NM_001099744.1 | 0.005683 |
| 11722555_sat | HADH | hydroxyacyl-CoA dehydrogenase | CR591982.1 | 0.005987 |
| 11736367_a_at | MCM10 | minichromosome maintenance complex component 10 | NM_182751.1 | 0.006448 |
| 11739660_x_at | PPCS | phosphopantothenoylcysteine synthetase | NM_001077447.1 | 0.0065 |
| 11757604_a_at | SAMM50 | sorting and assembly machinery component 50 homolog (S. cerevisiae) | BQ186212 | 0.006505 |
| 11722398_s_at | RWDD4 | RWD domain containing 4 | NM_152682.2 | 0.00654 |
| 11733866_a_at | RARS2 | arginyl-tRNA synthetase 2, mitochondrial | NM_020320.3 | 0.006608 |
| 11722351_at | SRSF8 | serine/arginine-rich splicing factor 8 | NM_032102.2 | 0.006693 |
| 11726320_at | ERO1L | ERO1-like (S. cerevisiae) | NM_014584.1 | 0.006774 |
| 11744384_x_at | USMG5 | up-regulated during skeletal muscle growth 5 homolog (mouse) | BC072683.1 | 0.006853 |
| 11733975_a_at | DDHD2 | DDHD domain containing 2 | BU631346 | 0.007241 |
| 11727533_a_at | FEZ2 | fasciculation and elongation protein zeta 2 (zygin II) | NM_001042548.1 | 0.007345 |
| 11723462_a_at | PHKB | phosphorylase kinase, beta | NM_001031835.2 | 0.007666 |
| 11718475_s_at | IDH1 | isocitrate dehydrogenase 1 (NADP+), soluble | NM_005896.2 | 0.007717 |
| 11744822_a_at | NDUFB2 | NADH dehydrogenase (ubiquinone) 1 beta subcomplex, 2, 8 kDa | BC063026.1 | 0.007876 |
| 11757589_a_at | NDUFA12 | NADH dehydrogenase (ubiquinone) 1 alpha subcomplex, 12 | BU537124 | 0.008475 |
| 11726186_x_at | C12orf48 | chromosome 12 open reading frame 48 | NM_017915.2 | 0.008601 |
| 11739972_at | NUAK1 | NUAK family, SNF1-like kinase, 1 | BU686994 | 0.008782 |
| 11755294_x_at | NEB | nebulin | BC063136.1 | 0.008985 |
| 11740962_a_at | UBA5 | ubiquitin-like modifier activating enzyme 5 | NM_198329.2 | 0.009092 |
| 11753867_a_at | NDUFA1 | NADH dehydrogenase (ubiquinone) 1 alpha subcomplex, 1, 7.5 kDa | AB451304.1 | 0.009324 |
| 11757665_x_at | NDUFS5 | NADH dehydrogenase (ubiquinone) Fe-S protein 5, 15 kDa (NADH-coenzyme Q reductase) | AA977996 | 0.009487 |
| 11757684_a_at | TPD52L2 | tumor protein D52-like 2 | AI806821 | 0.009563 |

TABLE 18-continued

Type III Epidermis; Down-regulated

| GeneTitan_ID | Gene | Title | Public ID | p |
|---|---|---|---|---|
| 11731068_s_at | FIGNL1 | fidgetin-like 1 | NM_022116.3 | 0.009587 |
| 11743064_at | CDC6 | cell division cycle 6 homolog (S. cerevisiae) | CR598029.1 | 0.009677 |
| 11746036_s_at | CBR1 | carbonyl reductase 1 | AK311219.1 | 0.009851 |
| 11729763_a_at | LSM10 | LSM10, U7 small nuclear RNA associated | NM_032881.1 | 0.010114 |
| 11719268_at | TNNC1 | troponin C type 1 (slow) | NM_003280.2 | 0.010462 |
| 11758199_s_at | RAD23B | RAD23 homolog B (S. cerevisiae) | BG571600 | 0.010584 |
| 11723291_a_at | NDUFA1 | NADH dehydrogenase (ubiquinone) 1 alpha subcomplex, 1, 7.5 kDa | NM_004541.3 | 0.010596 |
| 11715771_a_at | MRPL13 | mitochondrial ribosomal protein L13 | NM_014078.4 | 0.010834 |
| 11746174_s_at | IDH1 | isocitrate dehydrogenase 1 (NADP+), soluble | BC012846.1 | 0.011295 |
| 11724432_x_at | TRAPPC2 | trafficking protein particle complex 2 | NM_001011658.2 | 0.01144 |
| 11746489_x_at | GPAA1 | glycosylphosphatidylinositol anchor attachment protein 1 homolog (yeast) | BC006383.2 | 0.011462 |
| 11724120_a_at | TRIM59 | tripartite motif-containing 59 | NM_173084.2 | 0.01188 |
| 11764061_s_at | NDUFB3 | NADH dehydrogenase (ubiquinone) 1 beta subcomplex, 3, 12 kDa | AA887183 | 0.012144 |
| 11758083_s_at | HPGD | hydroxyprostaglandin dehydrogenase 15-(NAD) | AI743714 | 0.012171 |
| 11729715_a_at | CBR1 | carbonyl reductase 1 | NM_001757.2 | 0.012312 |
| 11734864_x_at | SARNP | SAP domain containing ribonucleoprotein | NM_033082.3 | 0.012428 |
| 11717314_a_at | HAUS1 | HAUS augmin-like complex, subunit 1 | NM_138443.3 | 0.012462 |
| 11751523_a_at | TMED5 | transmembrane emp24 protein transport domain containing 5 | AK293308.1 | 0.012569 |
| 11754800_s_at | GFM1 | G elongation factor, mitochondrial 1 | AK092293.1 | 0.012699 |
| 11746042_s_at | TRA2B | transformer 2 beta homolog (Drosophila) | AK098191.1 | 0.01285 |
| 11736741_a_at | MKI67 | antigen identified by monoclonal antibody Ki-67 | NM_001145966.1 | 0.012861 |
| 11729333_at | PADI1 | peptidyl arginine deiminase, type I | NM_013358.2 | 0.013091 |
| 11751291_a_at | SFXN4 | sideroflexin 4 | AY269785.1 | 0.013333 |
| 11717991_a_at | SIDT2 | SID1 transmembrane family, member 2 | NM_001040455.1 | 0.013344 |
| 11748896_s_at | CCRL1 | chemokine (C-C motif) receptor-like 1 | AK304461.1 | 0.013521 |
| 11716395_a_at | GPR56 | G protein-coupled receptor 56 | NM_001145774.1 | 0.013559 |
| 11729716_s_at | CBR1 | carbonyl reductase 1 | NM_001757.2 | 0.01399 |
| 11716063_at | TNC | tenascin C | NM_002160.2 | 0.014267 |
| 11758011_x_at | EEF1A1 | eukaryotic translation elongation factor 1 alpha 1 | BI495952 | 0.014362 |
| 11720317_a_at | DAD1 | defender against cell death 1 | NM_001344.2 | 0.014754 |
| 11720186_s_at | MAD2L1 | MAD2 mitotic arrest deficient-like 1 (yeast) | NM_002358.3 | 0.014969 |
| 11725960_s_at | CALM3 | calmodulin 3 (phosphorylase kinase, delta) | NM_005184.2 | 0.015262 |
| 11730753_at | AGPAT5 | 1-acylglycerol-3-phosphate O-acyltransferase 5 (lysophosphatidic acid acyltransferase, epsilon) | NM_018361.3 | 0.015361 |
| 11735839_at | STX19 | syntaxin 19 | NM_001001850.1 | 0.015426 |
| 11746655_a_at | ACAA1 | acetyl-CoA acyltransferase 1 | AK303251.1 | 0.015895 |
| 11744002_s_at | MTHFD2 | methylenetetrahydrofolate dehydrogenase (NADP+ dependent) 2, methenyltetrahydrofolate cyclohydrolase | BG026531 | 0.015966 |
| 11721296_a_at | NDUFB1 | NADH dehydrogenase (ubiquinone) 1 beta subcomplex, 1, 7 kDa | NM_004545.3 | 0.016187 |

TABLE 18-continued

| Type III Epidermis; Down-regulated | | | | |
|---|---|---|---|---|
| GeneTitan_ID | Gene | Title | Public ID | p |
| 11725125_a_at | NEB | nebulin | NM_004543.3 | 0.016335 |
| 11716624_s_at | XPO1 | exportin 1 (CRM1 homolog, yeast) | NM_003400.3 | 0.016341 |
| 11759922_a_at | PARD3 | par-3 partitioning defective 3 homolog (C. elegans) | BC071566.1 | 0.016372 |

TABLE 19

| Type III Dermis; Up-regulated | | | | |
|---|---|---|---|---|
| GeneTitan_ID | Gene | Title | Public ID | p |
| 11733167_at | LRRN4CL | LRRN4 C-terminal like | BC053902.1 | 0.000101 |
| 11716549_s_at | ISLR | immunoglobulin superfamily containing leucine-rich repeat | NM_005545.3 | 0.00021 |
| 11743191_a_at | NTM | neurotrimin | AI343272 | 0.000486 |
| 11725753_a_at | GRIA3 | glutamate receptor, ionotrophic, AMPA 3 | U10301.1 | 0.000741 |
| 11741377_a_at | MMP2 | matrix metallopeptidase 2 (gelatinase A, 72 kDa gelatinase, 72 kDa type IV collagenase) | NM_001127891.1 | 0.001476 |
| 11717765_a_at | MGLL | monoglyceride lipase | NM_007283.5 | 0.001622 |
| 11721372_at | TCF7L1 | transcription factor 7-like 1 (T-cell specific, HMG-box) | NM_031283.1 | 0.001646 |
| 11722839_at | LYAR | Ly1 antibody reactive homolog (mouse) | AW958593 | 0.001955 |
| 11762135_at_ | PTPRK | protein tyrosine phosphatase, receptor type, K | BC063596.1 | 0.002158 |
| 11721467_s_at | CD276 | CD276 molecule | NM_001024736.1 | 0.002325 |
| 11761134_at | MYST3 | MYST histone acetyltransferase (monocytic leukemia) 3 | BC142959.1 | 0.003233 |
| 11720440_at | OLFML2B | olfactomedin-like 2B | NM_015441.1 | 0.003454 |
| 11745431_a_at | SVIL | supervillin | BC092440.1 | 0.003484 |
| 11739746_s_at | SVIL | supervillin | CD366976 | 0.003636 |
| 11757808_s_at | RERE | arginine-glutamic acid dipeptide (RE) repeats | BM706668 | 0.003739 |
| 11725937_a_at | LGALS3 | lectin, galactoside-binding, soluble, 3 | BC053667.1 | 0.003825 |
| 11720274_x_at | ALKBH6 | alkB, alkylation repair homolog 6 (E. coli) | NM_032878.3 | 0.003968 |
| 11755955_a_at | FAP | fibroblast activation protein, alpha | AL832166.1 | 0.003989 |
| 11724619_at | RSPO3 | R-spondin 3 homolog (Xenopus laevis) | NM_032784.3 | 0.004121 |
| 11729170_x_at | DUSP10 | dual specificity phosphatase 10 | AF179212.1 | 0.004193 |
| 11752038_a_at | AQPEP | laeverin | BC068560.1 | 0.004865 |
| 11720846_at | CD248 | CD248 molecule, endosialin | NM_020404.2 | 0.005206 |
| 11731143_a_at | GPR133 | G protein-coupled receptor 133 | NM_198827.3 | 0.005394 |
| 11728451_a_at | PCOLCE2 | procollagen C-endopeptidase enhancer 2 | NM_013363.2 | 0.005523 |
| 11731682_at | CD70 | CD70 molecule | NM_001252.3 | 0.005777 |
| 11716226_a_at | LIMA1 | LIM domain and actin binding 1 | BC136763.1 | 0.006288 |
| 11750244_a_at | MGLL | monoglyceride lipase | AK304844.1 | 0.00649 |
| 11762370_x_at | BNC1 | basonuclin 1 | L03427.1 | 0.006531 |
| 11729101_a_at | AKR1C2 | aldo-keto reductase family 1, member C2 (dihyd rod iol dehydrogenase 2; bile acid binding protein; 3-alpha hydroxysteroid dehydrogenase, type III) | NM_205845.1 | 0.006587 |
| 11731649_x_at | NTM | neurotrimin | AY358331.1 | 0.006934 |
| 11716238_at | ARHGAP1 | Rho GTPase activating protein 1 | NM_004308.2 | 0.006953 |
| 11728498_a_at | SVIL | supervillin | NM_003174.3 | 0.00696 |
| 11725517_x_at | ABCG1 | ATP-binding cassette, sub-family G (WHITE), member 1 | NM_207627.1 | 0.007347 |
| 11728605_s_at | LIMS1 | LIM and senescent cell antigen-like domains 1 | NM_033514.2 | 0.007353 |
| 11752843_x_at | SQSTM1 | sequestosome 1 | AK304877.1 | 0.007432 |
| 11757557_s_at | CADM1 | cell adhesion molecule 1 | H23245 | 0.007475 |
| 11718269_x_at | ANGPTL2 | angiopoietin-like 2 | AY358274.1 | 0.007782 |
| 11747944_a_at | PPFIA2 | protein tyrosine phosphatase, receptor type, f polypeptide (PTPRF), interacting protein (liprin), alpha 2 | AK296380.1 | 0.008378 |

TABLE 19-continued

| | Type III Dermis; Up-regulated | | | |
|---|---|---|---|---|
| GeneTitan_ID | Gene | Title | Public ID | p |
| 11761149_a_at | C5orf45 | chromosome 5 open reading frame 45 | AK293901.1 | 0.008409 |
| 11737357_a_at | CNGA3 | cyclic nucleotide gated channel alpha 3 | NM_001298.2 | 0.008783 |
| 11743250_a_at | MMP2 | matrix metallopeptidase 2 (gelatinase A, 72 kDa gelatinase, 72 kDa type IV collagenase) | BX357054 | 0.009096 |
| 11725515_a_at | ABCG1 | ATP-binding cassette, sub-family G (WHITE), member 1 | NM_207627.1 | 0.009131 |
| 11759362_x_at | PHKG1 | phosphorylase kinase, gamma 1 (muscle) | BC051327.1 | 0.009194 |
| 11717802_s_at | ATF5 | activating transcription factor 5 | BE300055 | 0.009354 |
| 11723070_a_at | CYTL1 | cytokine-like 1 | NM_018659.2 | 0.009527 |
| 11731650_a_at | NTM | neurotrimin | NM_001048209.1 | 0.009599 |
| 11720845_a_at | CD248 | CD248 molecule, endosialin | NM_020404.2 | 0.009838 |
| 11716322_s_at | PRKCDBP | protein kinase C, delta binding protein | NM_145040.2 | 0.009887 |
| 11718658_s_at | CD34 | CD34 molecule | NM_001773.2 | 0.010659 |
| 11747945_x_at | PPFIA2 | protein tyrosine phosphatase, receptor type, f polypeptide (PTPRF), interacting protein (liprin), alpha 2 | AK296380.1 | 0.010696 |
| 11717764_x_at | MGLL | monoglyceride lipase | BC006230.2 | 0.010744 |
| 11743251_s_at | MMP2 | matrix metallopeptidase 2 (gelatinase A, 72 kDa gelatinase, 72 kDa type IV collagenase) | BX357054 | 0.010854 |
| 11731303_a_at | DUSP10 | dual specificity phosphatase 10 | BC020608.1 | 0.010964 |
| 11719737_a_at | FAM134B | family with sequence similarity 134, member B | BC053326.1 | 0.011265 |
| 11758143_s_at | DUSP8 | dual specificity phosphatase 8 | BE350906 | 0.011421 |
| 11724441_x_at | PTGIS | prostaglandin I2 (prostacyclin) synthase | NM_000961.3 | 0.011582 |
| 11737583_s_at | SGCD | sarcoglycan, delta (35 kDa dystrophin-associated glycoprotein) | NM_001128209.1 | 0.01169 |
| 11729541_a_at | CAMKK2 | calcium/calmodulin-dependent protein kinase kinase 2, beta | AB081337.1 | 0.011881 |
| 11737108_a_at | CCRL1 | chemokine (C-C motif) receptor-like 1 | NM_178445.1 | 0.012 |
| 11721507_at | DVL3 | dishevelled, dsh homolog 3 (Drosophila) | NM_004423.3 | 0.012974 |
| 11750245_x_at | MGLL | monoglyceride lipase | AK304844.1 | 0.013107 |
| 11737946_a_at | XPNPEP2 | X-prolyl aminopeptidase (aminopeptidase P) 2, membrane-bound | BC143901.1 | 0.01347 |
| 11727155_a_at | TRIOBP | TRIO and F-actin binding protein | NM_007032.5 | 0.013526 |
| 11720441_x_at | OLFML2B | olfactomedin-like 2B | NM015441.1 | 0.01374 |
| 11727773_at | LARP6 | La ribonucleoprotein domain family, member 6 | NM_197958.1 | 0.013995 |
| 11728499_x_at | SVIL | supervillin | NM_003174.3 | 0.01402 |
| 11745659_s_at | POM121 | POM121 membrane glycoprotein | BC130587.1 | 0.014097 |
| 11752562_x_at | CDH13 | cadherin 13, H-cadherin (heart) | AK294277.1 | 0.014197 |
| 11720617_at | TRIM9 | tripartite motif-containing 9 | NM_015163.5 | 0.014562 |
| 11757548_s_at | ADAMTSL1 | ADAMTS-like 1 | DB329733 | 0.014859 |
| 11753179_s_at | FAM134B | family with sequence similarity 134, member B | BC030517.1 | 0.014991 |
| 11729285_a_at | NFU1 | NFU1 iron-sulfur cluster scaffold homolog (S. cerevisiae) | NM_001002755.1 | 0.01519 |
| 11741286_a_at | CCRL1 | chemokine (C-C motif) receptor-like 1 | AF110640.1 | 0.015787 |
| 11732315_a_at | SGCD | sarcoglycan, delta (35 kDa dystrophin-associated glycoprotein) | AF010236.1 | 0.015795 |
| 11715852_at | PDGFRB | platelet-derived growth factor receptor, beta polypeptide | NM_002609.3 | 0.016136 |
| 11730404_at | MEX3B | mex-3 homolog B (C. elegans) | NM_032246.3 | 0.0163 |
| 11751986_at | MMP19 | matrix metallopeptidase 19 | U38320.1 | 0.016486 |
| 11731122_a_at | VASH2 | vasohibin 2 | BC051856.1 | 0.016505 |
| 11732785_a_at | C16orf45 | chromosome 16 open reading frame 45 | NM_001142469.1 | 0.017241 |
| 11757765_s_at | SGCD | sarcoglycan, delta (35 kDa dystroph in-associated glycoprotein) | AA401248 | 0.017347 |
| 11743143_at | COX11 | COX11 cytochrome c oxidase assembly homolog (yeast) | AK293851.1 | 0.017504 |

TABLE 19-continued

Type III Dermis; Up-regulated

| GeneTitan_ID | Gene | Title | Public ID | p |
|---|---|---|---|---|
| 11724142_s_at | RAB11FIP2 | RAB11 family interacting protein 2 (class I) | DB356544 | 0.017868 |
| 11723075_a_at | BCL9L | B-cell CLL/lymphoma 9-like | AY296059.1 | 0.017989 |
| 11747704_a_at | CLDN11 | claudin 11 | AK294087.1 | 0.017998 |
| 11716376_at | SERPINA5 | serpin peptidase inhibitor, clade A (alpha-1 antiproteinase, antitrypsin), member 5 | NM_000624.4 | 0.018046 |
| 11756879_a_at | STARD9 | StAR-related lipid transfer (START) domain containing 9 | CR936665.1 | 0.018874 |
| 11733166_at | LRRN4CL | LRRN4 C-terminal like | NM_203422.1 | 0.018933 |
| 11720163_at | VEGFC | vascular endothelial growth factor C | NM_005429.2 | 0.018951 |
| 11754821_s_at | SLC38A1 | solute carrier family 38, member 1 | AI476037 | 0.019062 |
| 11720082_at | CBX6 | chromobox homolog 6 | NM_014292.3 | 0.020169 |
| 11762231_x_at | BBS1 | Bardet-Biedl syndrome 1 | AK294962.1 | 0.020213 |
| 11732462_at | ADAMTSL1 | ADAMTS-like 1 | AK123028.1 | 0.020317 |
| 11761563_x_at | HEATR1 | HEAT repeat containing 1 | BC062442.1 | 0.0204 |
| 11727714_at | KCNJ12 | potassium inwardly-rectifying channel, subfamily J, member 12 | NM_021012.4 | 0.020553 |
| 11727780_a_at | SCARA5 | scavenger receptor class A, member 5 (putative) | NM_173833.4 | 0.020636 |
| 11749436_a_at | NFIC | nuclear factor I/C (CCAAT-binding transcription factor) | AK297825.1 | 0.020877 |
| 11731209_s_at | C15orf59 | chromosome 15 open reading frame 59 | NM_001039614.1 | 0.021422 |
| 11727125_a_at | PVRL3 | poliovirus receptor-related 3 | BE544927 | 0.021561 |
| 11744741_at | LOH3CR2A | loss of heterozygosity, 3, chromosomal region 2, gene A | AF086709.2 | 0.021592 |
| 11717891_a_at | ECM1 | extracellular matrix protein 1 | BC023505.2 | 0.021868 |

TABLE 20

Type III Dermis; Down-regulated

| GeneTitan_ID | Gene | Title | Public ID | p |
|---|---|---|---|---|
| 11727158_a_at | STRBP | spermatid perinuclear RNA binding protein | NM_018387.3 | 0.000131 |
| 11756850_x_at | CCT8 | chaperonin containing TCP1, subunit 8 (theta) | CR612497.1 | 0.000172 |
| 11754000_x_at | CD58 | CD58 molecule | CR456939.1 | 0.000222 |
| 11737761_a_at | HSD17B4 | hydroxysteroid (17-beta) dehydrogenase 4 | NM_000414.2 | 0.000267 |
| 11754276_a_at | RAD23B | RAD23 homolog B (S. cerevisiae) | BG501496 | 0.000343 |
| 11743094_at | SPRR4 | small proline-rich protein 4 | BC069445.1 | 0.000362 |
| 11724156_at | SULT1E1 | sulfotransferase family 1E, estrogen-preferring, member 1 | NM_005420.2 | 0.000395 |
| 11749267_a_at | SRD5A1 | steroid-5-alpha-reductase, alpha polypeptide 1 (3-oxo-5 alpha-steroid delta 4-dehydrogenase alpha 1) | AK315996.1 | 0.000399 |
| 11720183_s_at | EEF1B2 | eukaryotic translation elongation factor 1 beta 2 | NM_001959.3 | 0.000428 |
| 11737053_s_at | HSPD1 | heat shock 60 kDa protein 1 (chaperonin) | NM_002156.4 | 0.000467 |
| 11740377_a_at | PXMP4 | peroxisomal membrane protein 4, 24 kDa | AK297018.1 | 0.000581 |
| 11726318_s_at | EEF1G | eukaryotic translation elongation factor 1 gamma | NM_001404.4 | 0.000583 |
| 11720184_x_at | EEF1B2 | eukaryotic translation elongation factor 1 beta 2 | NM_001959.3 | 0.000595 |
| 11746149_x_at | BCHE | butyrylcholinesterase | M16474.1 | 0.000611 |
| 11737762_x_at | HSD17B4 | hydroxysteroid (17-beta) dehydrogenase 4 | NM_000414.2 | 0.000646 |
| 11739725_a_at | TC2N | tandem C2 domains, nuclear | NM_001128595.1 | 0.000648 |

TABLE 20-continued

| Type III Dermis; Down-regulated | | | | |
|---|---|---|---|---|
| GeneTitan_ID | Gene | Title | Public ID | p |
| 11754918_s_at | HMGCS1 | 3-hydroxy-3-methylglutaryl-CoA synthase 1 (soluble) | AK095492.1 | 0.000648 |
| 11741799_a_at | BCOR | BCL6 corepressor | AF317391.1 | 0.000649 |
| 11736831_a_at | SEC23B | Sec23 homolog B (S. cerevisiae) | NM_032986.3 | 0.000656 |
| 11744777_s_at | DPY30 | dpy-30 homolog (C. elegans) | BC015970.1 | 0.000676 |
| 11754418_s_at | G3BP1 | GTPase activating protein (SH3 domain) binding protein 1 | AK130003.1 | 0.000682 |
| 11723250_a_at | EML2 | echinoderm microtubule associated protein like 2 | NM_012155.1 | 0.00072 |
| 11752369_a_at | IMPDH2 | IMP (inosine 5'-monophosphate) dehydrogenase 2 | AK293397.1 | 0.000726 |
| 11729643_s_at | TPD52 | tumor protein D52 | CB219128 | 0.000732 |
| 11755057_s_at | ATP2C1 | ATPase, Ca++ transporting, type 2C, member 1 | AB037768.1 | 0.000739 |
| 11716946_s_at | TM9SF3 | transmembrane 9 superfamily member 3 | AF269150.1 | 0.000773 |
| 11756300_a_at | ANP326 | acidic (leucine-rich) nuclear phosphoprotein 32 family, member B | BX432546 | 0.000781 |
| 11716134_a_at | MTOR | mechanistic target of rapamycin (serine/threonine kinase) | NM_004958.3 | 0.000785 |
| 11755203_x_at | RPL21 | ribosomal protein L21 | BX647669.1 | 0.000869 |
| 11730938_x_at | PYCR1 | pyrroline-5-carboxylate reductase 1 | NM_153824.1 | 0.000877 |
| 11750545_a_at | CNOT7 | CCR4-NOT transcription complex, subunit 7 | BC007315.2 | 0.000884 |
| 11727826_a_at | C2orf56 | chromosome 2 open reading frame 56 | BC004548.2 | 0.00093 |
| 11718344_a_at | CNOT7 | CCR4-NOT transcription complex, subunit 7 | NM_013354.5 | 0.000947 |
| 11756600_a_at | TPD52 | tumor protein D52 | AK308983.1 | 0.000999 |
| 11734619_x_at | ALOX156 | arachidonate 15-lipoxygenase, type B | NM_001141.2 | 0.001036 |
| 11715621_at | UFC1 | ubiquitin-fold modifier conjugating enzyme 1 | NM_016406.3 | 0.001145 |
| 11715958_s_at | RPL7 | ribosomal protein L7 | NM_000971.3 | 0.001233 |
| 11748713_a_at | ASPM | asp (abnormal spindle) homolog, microcephaly associated (Drosophila) | AY971957.1 | 0.001256 |
| 11758707_s_at | C5orf25 | chromosome 5 open reading frame 25 | DB526316 | 0.001417 |
| 200081_PM_s_at | RPS6 | ribosomal protein S6 | BE741754 | 0.00144 |
| 11726299_x_at | LGALS8 | lectin, galactoside-binding, soluble, 8 | AF342815.1 | 0.001452 |
| 11756210_a_at | RCL1 | RNA terminal phosphate cyclase-like 1 | AL582781 | 0.001477 |
| 11743604_s_at | RRM1 | ribonucleotide reductase M1 | BE618815 | 0.001487 |
| 11729641_a_at | TPD52 | tumor protein D52 | BG389015 | 0.001493 |
| 11718461_at | SLC39A11 | solute carrier family 39 (metal ion transporter), member 11 | NM_139177.3 | 0.001532 |
| 11725053_x_at | TOP1MT | topoisomerase (DNA) I, mitochondrial | NM_052963.1 | 0.001534 |
| 11758027_s_at | HOOK1 | hook homolog 1 (Drosophila) | CD243255 | 0.001606 |
| 11745205_s_at | TPD52 | tumor protein D52 | BC018117.1 | 0.001623 |
| 11760342_a_at | PPP3CB | protein phosphatase 3, catalytic subunit, beta isozyme | M29550.1 | 0.001681 |
| 11725875_at | WDR66 | WD repeat domain 66 | NM_144668.4 | 0.001791 |
| 11739308_s_at | DLG1 | discs, large homolog 1 (Drosophila) | BM681931 | 0.001815 |
| 11719666_a_at | STMN1 | stathmin 1 | BC082228.1 | 0.001852 |
| 11752283_a_at | ALOX15B | arachidonate 15-lipoxygenase, type B | AK298095.1 | 0.001904 |
| 11723312_a_at | PXMP2 | peroxisomal membrane protein 2, 22 kDa | NM_018663.1 | 0.001916 |
| 11719667_s_at | STMN1 | stathmin 1 | BC082228.1 | 0.001961 |

TABLE 20-continued

Type III Dermis; Down-regulated

| GeneTitan_ID | Gene | Title | Public ID | p |
|---|---|---|---|---|
| 11728791_at | THRSP | thyroid hormone responsive | NM_003251.2 | 0.001966 |
| 11734917_a_at | METTL4 | methyltransferase like 4 | BQ009802 | 0.001983 |
| 11717236_x_at | RPS7 | ribosomal protein S7 | NM_001011.3 | 0.002022 |
| 11754132_x_at | COMT | catechol-0-methyltransferase | BT007125.1 | 0.002101 |
| 11743372_s_at | PTGES3 | prostaglandin E synthase 3 (cytosolic) | CR611609.1 | 0.002174 |
| 11730411_a_at | PXMP4 | peroxisomal membrane protein 4, 24 kDa | BF057649 | 0.002209 |
| 200063_PM_s_at | NPM1 | nucleophosmin (nucleolar phosphoprotein B23, numatrin) | BC002398.1 | 0.002233 |
| 11722642_a_at | DGAT2 | diacylglycerol O-acyltransferase 2 | BC015234.1 | 0.002305 |
| 11752550_x_at | CCT8 | chaperonin containing TCP1, subunit 8 (theta) | AK293705.1 | 0.002336 |
| 11758217_s_at | FAM108C1 | family with sequence similarity 108, member C1 | CB997200 | 0.002358 |
| 11717182_a_at | PDS5A | PDS5, regulator of cohesion maintenance, homolog A (*S. cerevisiae*) | NM_001100399.1 | 0.002387 |
| 11717153_a_at | C20orf3 | chromosome 20 open reading frame 3 | NM_020531.2 | 0.002394 |
| 11742779_a_at | HIBCH | 3-hydroxyisobutyryl-CoA hydrolase | U66669.1 | 0.002431 |
| 11744264_a_at | SEC11C | SEC11 homolog C (*S. cerevisiae*) | AI816180 | 0.002433 |
| 11753788_x_at | CDKN3 | cyclin-dependent kinase inhibitor 3 | AF213040.1 | 0.002434 |
| 11758709_s_at | RDH11 | retinol dehydrogenase 11 (all-trans/9-cis/11-cis) | AI972157 | 0.002449 |
| 11727320_at | IGFL2 | IGF-like family member 2 | NM_001002915.2 | 0.002476 |
| 11730803_a_at | PRPF38B | PRP38 pre-mRNA processing factor 38 (yeast) domain containing B | NM_018061.2 | 0.002515 |
| 11753740_x_at | CYB5A | cytochrome b5 type A (microsomal) | CR456990.1 | 0.002572 |
| 11718246_a_at | KIAA0146 | KIAA0146 | NM_001080394.1 | 0.002609 |
| 11720768_at | METTL9 | methyltransferase like 9 | NM_016025.3 | 0.002613 |
| 11755017_a_at | CHCHD7 | coiled-coil-helix-coiled-coil-helix domain containing 7 | AK098285.1 | 0.002843 |
| 11732128_s_at | CCT4 | chaperonin containing TCP1, subunit 4 (delta) | BC106934.1 | 0.002855 |
| 11744900_x_at | FADS2 | fatty acid desaturase 2 | AF108658.1 | 0.002865 |
| 11715881_a_at | DAP3 | death associated protein 3 | NM_004632.2 | 0.002925 |
| 11756875_x_at | COMMD6 | COMM domain containing 6 | CR603325.1 | 0.002962 |
| 11756783_a_at | TF | transferrin | BC045772.1 | 0.002967 |
| 11723197_at | HNRNPA3 | heterogeneous nuclear ribonucleoprotein A3 | BX434302 | 0.003022 |
| 11729941_at | TMEM56 | transmembrane protein 56 | NM_152487.2 | 0.003035 |
| 11716813_a_at | GATM | glycine amidinotransferase (L-arginine:glycine amidinotransferase) | AK298350.1 | 0.003053 |
| 11721242_s_at | FDFT1 | farnesyl-diphosphate farnesyltransferase 1 | NM_004462.3 | 0.003125 |
| 11749786_x_at | HNRNPF | heterogeneous nuclear ribonucleoprotein F | AK296696.1 | 0.003153 |
| 11723313_s_at | PXMP2 | peroxisomal membrane protein 2, 22 kDa | NM_018663.1 | 0.003162 |
| 11727286_a_at | ZNF323 | zinc finger protein 323 | NM_001135215.1 | 0.003185 |
| 11720813_at | INTS10 | integrator complex subunit 10 | NM_018142.2 | 0.003216 |
| 11749874_a_at | OXCT1 | 3-oxoacid CoA transferase 1 | AK299668.1 | 0.003244 |
| 11757320_x_at | CYB5A | cytochrome b5 type A (microsomal) | AA706740 | 0.003263 |

TABLE 20-continued

Type III Dermis; Down-regulated

| GeneTitan_ID | Gene | Title | Public ID | p |
|---|---|---|---|---|
| 11733591_a_at | C1orf204 | chromosome 1 open reading frame 204 | NM_001134233.1 | 0.003297 |
| 11718135_at | PRPS2 | phosphoribosyl pyrophosphate synthetase 2 | NM_001039091.1 | 0.003316 |
| 11716302_s_at | ACSL1 | acyl-CoA synthetase long-chain family member 1 | NM_001995.2 | 0.003359 |
| 11744392_a_at | PAPOLA | poly(A) polymerase alpha | BC000927.1 | 0.003388 |
| 11741012_a_at | SC4MOL | sterol-C4-methyl oxidase-like | AK292418.1 | 0.00342 |
| 11722800_a_at | SS18 | synovial sarcoma translocation, chromosome 18 | CB241009 | 0.003458 |
| 11755439_x_at | UBAC2 | UBA domain containing 2 | BC053346.1 | 0.003608 |
| 11756674_s_at | STRBP | spermatid perinuclear RNA binding protein | CR596677.1 | 0.003641 |

The gene expression signatures provided in Table 9-20 can be used to classify the type of periorbital dyschromia exhibited by person. For example, a person can be classified as exhibiting Type I periorbital dyschromia when the gene expression signature of a skin tissue sample obtained from the periorbital region of the person corresponds to 15% or more (e.g., more than 25%, 50%, 75%, 80%, 90% or even up to 100%) of the genes from Tables 9 to 12. In other words, a person can be classified as exhibiting Type I periorbital dyschromia if the top 100 upregulated genes in the epidermis comprise 15% or more the genes in Table 9; the top 100 downregulated genes in the epidermis comprise 15% or more of the genes in Table 10; the top 100 upregulated genes in the dermis comprise 15% or more of the genes in Table 11; and/or the top 100 downregulated genes in the dermis comprise 15% or more of the genes in Table 12. Similarly, a person can be classified as exhibiting Type II or Type III periorbital dyschromia when the gene expression signature of the skin tissue sample comprises significantly upregulated and downregulated genes that correspond to 15% or more of the genes in at least one of Tables 13 to 16 or Tables 17 to 20, respectively.

Theme analysis may be used to identify biological or phenotypic themes associated with the gene expression data that correspond to Type I, Type II and Type III periorbital dyschromia. Theme analysis is a statistical analysis-based method for detecting biological patterns in gene expression data. The method uses an ontology of controlled vocabulary terms developed by the Gene Ontology ("GO") Consortium [Ashburner, M. et al. (2000) Gene ontology: tool for the unification of biology. The Gene Ontology Consortium. Nat Genet, 25, 25-29] that describe the biological processes, molecular functions and cellular components associated with gene products. Analysis involves statistical comparison of a regulated list of genes and a larger reference list of all the expressed genes, to determine if genes annotated to specific GO terms are significantly enriched in the regulated list. This analysis may reveal biological patterns when multiple genes associated with a given GO term occur on the regulated list at a frequency greater than expected by chance. Such analysis may be performed using Theme Extractor proprietary software and an algorithm that calculates the p-value of each ontology term. Data may be analyzed for statistical significance, for example, by the Fisher's exact test. Conventional approaches and statistical methods such as, for example, Gene Set Enrichment Analysis described by Subramanian, A., et al., in "Gene set enrichment analysis: a knowledge-based approach for interpreting genome-wide expression profiles," Proc. Natl. Acad Sci U.S.A, 102, 15545-155501 (2005) are suitable for conducting theme analysis herein.

Table 21 shows Gene Ontology Biological Process terms that are significantly enriched in the epidermis of subjects with Type I periorbital dyschromia. The results in Table 21 were generated from differentially expressed genes in those subjects with top ranked genes shown in Tables 13 and 14. Only the most highly significant themes are shown (p-value≤1×10$^{-2}$ to p≥1×10$^{-5}$) and the theme analysis was done separately for the up- and down-regulated genes. The level of indentation in the terms column (i.e., the number of dots preceding the term) generally indicates the level in the GO hierarchy and parent/child relationships between terms.

TABLE 21

| | Type I Epidermis vs N-D | | |
|---|---|---|---|
| Gene Ontology Biological Process Terms | Up | Down | Directional |
| GO:0002764 immune response-regulating signaling pathway | | ** | |
| GO:0002758 innate immune response-activating signal transduction | | *** | |
| GO:0002224 toll-like receptor signaling pathway | | ** | |
| GO:0048468 cell development | ** | | |
| GO:0002376 immune system process | | **** | |
| GO:0002252 immune effector process | | **** | |
| GO:0002253 activation of immune response | | **** | |
| GO:0002218 activation of innate immune response | | *** | |
| GO:0006955 immune response | | **** | |
| GO:0045087 innate immune response | | **** | |
| GO:0071383 cellular response to steroid hormone stimulus | ** | | |
| GO:0006954 inflammatory response | | * | |
| GO:0045047 protein targeting to ER | | **** | |
| GO:0032984 macromolecular complex disassembly | | **** | |
| GO:0016568 chromatin modification | * | | |
| GO:0050776 regulation of immune response | | **** | |
| GO:0006749 glutathione metabolic process | | ** | |
| GO:0019752 carboxylic acid metabolic process | | * | |
| GO:0007154 cell communication | * | | |

TABLE 21-continued

| Gene Ontology Biological Process Terms | Type I Epidermis vs N-D | | |
|---|---|---|---|
| | Up | Down | Directional |
| GO:0016042 lipid catabolic process | | * | |
| GO:0070588 calcium ion transmembrane transport | * | | |

*p-value between $1 \times 10^{-2}$ and $1 \times 10^{-3}$
**p-value between $1 \times 10^{-3}$ and $1 \times 10^{-4}$
***p-value between $1 \times 10^{-4}$ and $1 \times 10^{-5}$
****p-value less than $1 \times 10^{-5}$ Table 21 shows Gene Ontology Biological Process terms that are significantly enriched in the epidermis of subjects with Type II periorbital dyschromia. The results in Table 14 were generated from differentially expressed genes in those subjects with top ranked genes shown in Tables 13 and 14. Only the most highly significant themes are shown (p≤1× $10^{-2}$), and the theme analysis was done separately for the up- and down-regulated genes.

TABLE 22

| Gene Ontology Biological Process | Terms Type II Epidermis vs N-D | | |
|---|---|---|---|
| | Up | Down | Directional |
| GO:0042770 signal transduction in response to DNA damage | | **** | |
| GO:0072331 signal transduction by p53 class mediator | | **** | |
| GO:0007173 epidermal growth factor receptor signaling pathway | | ** | |
| GO:0001942 hair follicle development | | **** | |
| GO:0008544 epidermis development | | **** | |
| GO:0045444 fat cell differentiation | * | | |
| GO:0019882 antigen processing and presentation | | **** | |
| GO:0071453 cellular response to oxygen levels | | | ** |
| GO:0071456 cellular response to hypoxia | | | ** |
| GO:0031960 response to corticosteroid stimulus | * | | |
| GO:0033554 cellular response to stress | | **** | |
| GO:0006281 DNA repair | | ** | |
| GO:0000077 DNA damage checkpoint | | **** | |
| GO:0006950 response to stress | | ** | |
| GO:0009268 response to pH | | ** | |
| GO:0006886 intracellular protein transport | | **** | |
| GO:0006605 protein targeting | | **** | |
| GO:0015031 protein transport | | **** | |
| GO:0046907 intracellular transport | | **** | |
| GO:0048193 Golgi vesicle transport | | ** | |
| GO:0006839 mitochondrial transport | | **** | |
| GO:0015986 ATP synthesis coupled proton transport | | *** | |
| GO:0016568 chromatin modification | ** | | |
| GO:0031326 regulation of cellular biosynthetic process | ** | | |
| GO:0006521 regulation of cellular amino acid metabolic process | | **** | |
| GO:0010565 regulation of cellular ketone metabolic process | | **** | |
| GO:0051171 regulation of nitrogen compound metabolic process | | | |
| GO:0051726 regulation of cell cycle | | ** | |
| GO:0045454 cell redox homeostasis | | ** | |
| GO:0032652 regulation of interleukin-1 production | ** | | |
| GO:0035383 thioester metabolic process | | **** | |
| GO:0006637 acyl-CoA metabolic process | | **** | |
| GO:0006099 tricarboxylic acid cycle | | **** | |
| GO:0006635 fatty acid beta-oxidation | | ** | |

TABLE 22-continued

| Gene Ontology Biological Process | Terms Type II Epidermis vs N-D | | |
|---|---|---|---|
| | Up | Down | Directional |
| GO:0018108 peptidyl-tyrosine phosphorylation | ** | | |
| GO:0006082 organic acid metabolic process | | **** | |
| GO:0006520 cellular amino acid metabolic process | | ** | |
| GO:0043038 amino acid activation | | **** | |
| GO:0006091 generation of precursor metabolites and energy | | **** | |
| GO:0006096 glycolysis | | ** | |
| GO:0006119 oxidative phosphorylation | | **** | |
| GO:0042773 ATP synthesis coupled electron transport | | **** | |
| GO:0045333 cellular respiration | | **** | |
| GO:0007049 cell cycle | | **** | |
| GO:0005975 carbohydrate metabolic process | | *** | |
| GO:0006007 glucose catabolic process | | *** | |
| GO:0016052 carbohydrate catabolic process | | **** | |
| GO:0055114 oxidation-reduction process | | **** | |

Table 23 shows Gene Ontology Biological Process terms that are significantly enriched in the epidermis of subjects with Type III periorbital dyschromia. The results in Table 23 were generated differentially expressed genes in those subjects with top ranked genes shown in Tables 17 and 18. Only the most highly significant themes are shown (p-value $<1 \times 10^{-2}$), and the theme analysis was done separately for the up- and down-regulated genes.

TABLE 23

| Gene Ontology Biological Process Terms | Type III Epidermis vs N-D | | |
|---|---|---|---|
| | Up | Down | Directional |
| GO:0048731 system development | ** | | |
| GO:0048856 anatomical structure development | *** | | |
| GO:0030154 cell differentiation | ** | | |
| GO:0070482 response to oxygen levels | * | | |
| GO:0033365 protein localization to organelle | | ** | |
| GO:0045047 protein targeting to ER | | ** | |
| GO:0006605 protein targeting | | ** | |
| GO:0006612 protein targeting to membrane | | ** | |
| GO:0006839 mitochondrial transport | | ** | |
| GO:0001934 positive regulation of protein phosphorylation | ** | | |
| GO:0051347 positive regulation of transferase activity | ** | | |
| GO:0010627 regulation of intracellular protein kinase cascade | ** | | |
| GO:0080135 regulation of cellular response to stress | * | | |
| GO:0051320 S phase | | *** | |
| GO:0006414 translational elongation | | **** | |
| GO:0006091 generation of precursor metabolites and energy | | *** | |
| GO:0006119 oxidative phosphorylation | | ** | |
| GO:0022900 electron transport chain | | **** | |
| GO:0045333 cellular respiration | | **** | |
| GO:0055114 oxidation-reduction process | | *** | |

Table 24 shows Gene Ontology Biological Process terms that are significantly enriched in the dermis of subjects with Type I periorbital dyschromia. The results in Table 24 were generated from differentially expressed genes in those subjects with top ranked genes shown in Tables 11 and 12. Only the most highly significant themes are shown (p≤$1 \times 10^{-2}$), and the theme analysis was done separately for the up- and down-regulated genes.

TABLE 24

| Gene Ontology Biological Process Terms | Type I Dermis vs N-D | | |
|---|---|---|---|
| | Up | Down | Directional |
| GO:0000165 MAPK cascade | ** | | |
| GO:0048011 nerve growth factor receptor signaling pathway | * | | |
| GO:0007179 transforming growth factor beta receptor signaling pathway | * | | |
| GO:0050877 neurological system process | *** | | |
| GO:0007596 blood coagulation | * | | |
| GO:0050878 regulation of body fluid levels | * | | |
| GO:0001944 vasculature development | **** | | |
| GO:0001568 blood vessel development | **** | | |
| GO:0048514 blood vessel morphogenesis | **** | | |
| GO:0001525 angiogenesis | **** | | |
| GO:0030183 B cell differentiation | | * | |
| GO:0007399 nervous system development | **** | | |
| GO:0022008 neurogenesis | *** | | |
| GO:0048699 generation of neurons | *** | | |
| GO:0030182 neuron differentiation | ** | | |
| GO:0048666 neuron development | ** | | |
| GO:0048870 cell motility | ** | | |
| GO:0043627 response to estrogen stimulus | ** | | |
| GO:0006281 DNA repair | | **** | |
| GO:0001666 response to hypoxia | * | | |
| GO:0006979 response to oxidative stress | * | | |
| GO:0009611 response to wounding | *** | | |
| GO:0070482 response to oxygen levels | ** | | |
| GO:0033365 protein localization to organelle | | **** | |
| GO:0045047 protein targeting to ER | | **** | |
| GO:0006605 protein targeting | | **** | |
| GO:0015031 protein transport | | **** | |
| GO:0046907 intracellular transport | | **** | |
| GO:0034330 cell junction organization | ** | | |
| GO:0030198 extracellular matrix organization | * | | |
| GO:0007010 cytoskeleton organization | * | | |
| GO:0051276 chromosome organization | | *** | |
| GO:0032200 telomere organization | | ** | |
| GO:0006338 chromatin remodeling | | * | |
| GO:0043408 regulation of MAPK cascade | *** | | |
| GO:0051924 regulation of calcium ion transport | * | | |
| GO:0010827 regulation of glucose transport | | | *** |
| GO:0030334 regulation of cell migration | **** | | |
| GO:0010564 regulation of cell cycle process | | ** | |
| GO:0010646 regulation of cell communication | **** | | |
| GO:0022402 cell cycle process | | ** | |
| GO:0022403 cell cycle phase | | *** | |
| GO:0007049 cell cycle | | ** | |
| GO:0000278 mitotic cell cycle | | **** | |
| GO:0007154 cell communication | **** | | |
| GO:0008202 steroid metabolic process | * | | |
| GO:0006694 steroid biosynthetic process | | ** | |
| GO:0016126 sterol biosynthetic process | | **** | |
| GO:0006695 cholesterol biosynthetic process | | **** | |
| GO:0061061 muscle structure development | * | | |

Table 25 shows Gene Ontology Biological Process terms that are significantly enriched in the dermis of subjects with Type II periorbital dyschromia. The results in Table 25 were generated from differentially expressed genes in those subjects with top ranked genes shown in Tables 15 and 16. Only the most highly significant themes are shown ($p < 1 \times 10^{-2}$), and the theme analysis was done separately for the up- and down-regulated genes.

TABLE 25

| Gene Ontology Biological Process Terms | Type II Dermis vs. N-D | | |
|---|---|---|---|
| | Up | Down | Directional |
| GO:0019226 transmission of nerve impulse | * | | |
| GO:0050877 neurological system process | ** | | |
| GO:0007399 nervous system development | ** | | |
| GO:0022008 neurogenesis | **** | | |
| GO:0048699 generation of neurons | *** | | |
| GO:0030182 neuron differentiation | *** | | |
| GO:0048666 neuron development | *** | | |
| GO:0031175 neuron projection development | ** | | |
| GO:0007409 axonogenesis | ** | | |
| GO:0048667 cell morphogenesis involved in neuron differentiation | ** | | |
| GO:0048468 cell development | *** | | |
| GO:0006281 DNA repair | | **** | |
| GO:0033365 protein localization to organelle | | **** | |
| GO:0070972 protein localization to endoplasmic reticulum | | **** | |
| GO:0006605 protein targeting | | **** | |
| GO:0006612 protein targeting to membrane | | **** | |
| GO:0015031 protein transport | | **** | |
| GO:0006810 transport | | **** | |
| GO:0051641 cellular localization | | **** | |
| GO:0016043 cellular component organization | | **** | |
| GO:0022411 cellular component disassembly | | **** | |
| GO:0030198 extracellular matrix organization | * | | |
| GO:0032984 macromolecular complex disassembly | | **** | |
| GO:0043624 cellular protein complex disassembly | | **** | |
| GO:0071156 regulation of cell cycle arrest | | ** | |
| GO:0010646 regulation of cell communication | * | | |
| GO:0051320 S phase | | ** | |
| GO:0044248 cellular catabolic process | | **** | |
| GO:0006457 protein folding | | ** | |
| GO:0007049 cell cycle | | * | |
| GO:0000278 mitotic cell cycle | | ** | |
| GO:0007154 cell communication | * | | |
| GO:0006694 steroid biosynthetic process | | ** | |
| GO:0006695 cholesterol biosynthetic process | | *** | |

Table 26 shows Gene Ontology Biological Process terms that are significantly enriched in the epidermis of subjects with Type III periorbital dyschromia. The results in Table 26 were generated from differentially expressed genes in those subjects with top ranked genes shown in Tables 19 and 20. Only the most highly significant themes are shown ($p \leq 1 \times 10^{-2}$), and the theme analysis was done separately for the up- and down-regulated genes.

TABLE 26

| Gene Ontology Biological Process Terms | Type III Dermis vs. N-D | | |
|---|---|---|---|
| | Up | Down | Directional |
| GO:0007155 cell adhesion | ** | | |
| GO:0019226 transmission of nerve impulse | * | | |
| GO:0051403 stress-activated MAPK cascade | *** | | |
| GO:0007254 JNK cascade | ** | | |
| GO:0000165 MAPK cascade | **** | | |
| GO:0016055 Wnt receptor signaling pathway | * | | |
| GO:0050877 neurological system process | ** | | |
| GO:0001944 vasculature development | *** | | |
| GO:0001568 blood vessel development | ** | | |
| GO:0048514 blood vessel morphogenesis | ** | | |
| GO:0022008 neurogenesis | ** | | |
| GO:0030182 neuron differentiation | ** | | |
| GO:0048666 neuron development | ** | | |
| GO:0061061 muscle structure development | ** | | |
| GO:0042692 muscle cell differentiation | ** | | |
| GO:0048646 anatomical structure formation involved in morphogenesis | **** | | |
| GO:0033554 cellular response to stress | | * | |
| GO:0006281 DNA repair | | **** | |
| GO:0001666 response to hypoxia | ** | | |
| GO:0070482 response to oxygen levels | *** | | |
| GO:0036293 response to decreased oxygen levels | ** | | |
| GO:0034613 cellular protein localization | | **** | |

TABLE 26-continued

Type III Dermis vs. N-D

| Gene Ontology Biological Process Terms | Up | Down | Directional |
|---|---|---|---|
| GO:0033365 protein localization to organelle | | **** | |
| GO:0070972 protein localization to endoplasmic reticulum | | **** | |
| GO:0045047 protein targeting to ER | | **** | |
| GO:0006886 intracellular protein transport | | **** | |
| GO:0006605 protein targeting | | **** | |
| GO:0006612 protein targeting to membrane | | **** | |
| GO:0015031 protein transport | | **** | |
| GO:0006811 ion transport | *** | | |
| GO:0006812 cation transport | ** | | |
| GO:0030001 metal ion transport | ** | | |
| GO:0050000 chromosome localization | | **** | |
| GO:0022411 cellular component disassembly | | **** | |
| GO:0034330 cell junction organization | * | | |
| GO:0034622 cellular macromolecular complex assembly | | **** | |
| GO:0007010 cytoskeleton organization | ** | | |
| GO:0000226 microtubule cytoskeleton organization | | ** | |
| GO:0070925 organelle assembly | | **** | |
| GO:0051276 chromosome organization | | *** | |
| GO:0032200 telomere organization | | *** | |
| GO:0000819 sister chromatid segregation | | **** | |
| GO:0043408 regulation of MAPK cascade | **** | | |
| GO:0010646 regulation of cell communication | **** | | |
| GO:0019725 cellular homeostasis | * | | |
| GO:0022402 cell cycle process | | **** | |
| GO:0035383 thioester metabolic process | | ** | |
| GO:0071616 acyl-CoA biosynthetic process | | ** | |
| GO:0035337 fatty-acyl-CoA metabolic process | | *** | |
| GO:0044248 cellular catabolic process | | **** | |
| GO:0046394 carboxylic acid biosynthetic process | | *** | |
| GO:0044255 cellular lipid metabolic process | | * | |
| GO:0006631 fatty acid metabolic process | | ** | |
| GO:0019752 carboxylic acid metabolic process | | **** | |
| GO:0007049 cell cycle | | **** | |
| GO:0007154 cell communication | *** | | |
| GO:0005975 carbohydrate metabolic process | | ** | |
| GO:0006694 steroid biosynthetic process | | ** | |
| GO:0006695 cholesterol biosynthetic process | | **** | |
| GO:0008610 lipid biosynthetic process | | ** | |
| GO:0055114 oxidation-reduction process | | ** | |

The theme analysis of Type I periorbital dyschromia may be broadly correlated to cellular physiological responses associated with cell stress and cell communication in the epidermis and metabolism, stress and structure in the dermis. In particular, a theme analysis of epidermal gene expression related to Type I periorbital dyschromia revealed, generally, an increase in gene expression associated with calcium ion trans-membrane transport, chromatin modification and cell communication and a decrease in gene expression associated with immune response and toll-like receptor pathway. Dermal gene expression revealed the following general themes: an increase in gene expression associated with response to estrogen stimulus, regulation of body fluid levels, regulation of cell migration, hypoxic stress, oxidative damage, response to wounding, blood vessel development, extracellular matrix organization, cytoskeleton organization, cell junction organization, neuron development and muscle structure development and a decrease in gene expression associated with cholesterol synthesis, regulation of glucose transport and protein transport.

The theme analysis of Type II periorbital dyschromia appears to show a general correlation with the cellular physiological responses associated with metabolism and energy production, cell stress and cell communication in the epidermis and metabolism and structure in the dermis. In particular, a theme analysis of epidermal gene expression related to Type II periorbital dyschromia revealed, generally, an increase in gene expression associated with chromatin modification and a decrease in gene expression associated with glycolysis, ATP synthesis, cell cycle, TCA cycle, response to pH, antigen presentation and processing. Dermal gene expression revealed the following general themes: an increase in gene expression associated with transmission of nerve impulses and neuron development and a decrease in gene expression associated with cholesterol synthesis.

Theme analysis of Type III periorbital dyschromia may be broadly correlated to cellular physiological responses associated with metabolism in the epidermis and metabolism and nutrition, stress and cell communication, and structure in the dermis. In particular, a theme analysis of epidermal gene expression related to Type III periorbital dyschromia revealed, generally, a decrease in gene expression associated with oxidation and reduction process. A theme analysis of dermal gene expression revealed the following general themes: an increase in gene expression associated with ion and metal transport, regulation of the MAPK signaling cascade, regulation of Jun Kinase activity, blood vessels and neuron development and a decrease in gene expression associated with cholesterol synthesis, fatty acid metabolic process, microtubule cytoskeleton organization, organelle assembly, and carbohydrate metabolic process.

Products for treating different types of periorbital dyschromia are described in U.S. Provisional Application No. 61/798,278, filed by Osorio, et al., on Mar. 15, 2013 and titled "Array of Products." Methods of treating different types of periorbital dyschromia are described in U.S. Provisional App. No. 61/798,340, filed by Osorio et al., on Mar. 15, 2013 and titled "Methods of Treating Periorbital Dyschromia."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" Additionally, properties described herein may include one or more ranges of values. It is to be understood that these ranges include every value within the range, even though the individual values in the range may not be expressly disclosed.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of identifying periorbital dyschromia, comprising:
 (a) identifying skin in a periorbital region of a person comprising periorbital dyschromia;
 (b) capturing an image of the identified skin in the periorbital region with an image capture device;

(c) analyzing the image with a computer, wherein at least a portion of the image is color corrected and a measured imaging value is generated from the color corrected portion, and the measured imaging value is normalized relative to an imaging value obtained from a cheek;

(d) identifying the person as exhibiting Type I periorbital dyschromia when the portion of skin is disposed in Zone 1, Zone 2 and Zone 3 of the periorbital region and the measured imaging value corresponds to at least one value from Table 1, identifying the person as exhibiting Type II periorbital dyschromia when the portion of skin is disposed in only in Zone 1 of the periorbital region and the measured imaging value corresponds to at least one value from Table 2, or identifying the person as exhibiting Type III periorbital dyschromia when the portion of skin is disposed in Zone 1 and Zone 2 and the measured imaging value corresponds to at least one value from Table 3; and (e) communicating the type of periorbital dyschromia identified in (d) to the person.

2. The method of claim 1, wherein the measured imaging values includes at least one RGB color imaging value.

3. The method of claim 1, wherein the imaging values are measured using an RGB imaging technique.

* * * * *